(12) United States Patent
Holson et al.

(10) Patent No.: US 9,790,184 B2
(45) Date of Patent: Oct. 17, 2017

(54) INHIBITORS OF HISTONE DEACETYLASE

(71) Applicants: The General Hospital Corporation, Boston, MA (US); The Broad Institute, Inc., Cambridge, MA (US)

(72) Inventors: Edward Holson, Newton, MA (US); Florence Fevrier Wagner, Ashland, MA (US); Stephen J. Haggarty, Gloucester, MA (US); Yan-Ling Zhang, Lexington, MA (US); Morten Lundh, Copenhagen (DK); Bridget Wagner, Medford, MA (US); Michael C. Lewis, Boston, MA (US); Tracey Lynn Petryshen, Arlington, MA (US)

(73) Assignees: The Broad Institute, Inc., Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/417,477

(22) PCT Filed: Jul. 29, 2013

(86) PCT No.: PCT/US2013/052572
§ 371 (c)(1),
(2) Date: Jan. 26, 2015

(87) PCT Pub. No.: WO2014/018979
PCT Pub. Date: Jan. 30, 2014

(65) Prior Publication Data
US 2015/0191427 A1    Jul. 9, 2015

Related U.S. Application Data

(60) Provisional application No. 61/676,496, filed on Jul. 27, 2012.

(51) Int. Cl.
*A61K 31/167*    (2006.01)
*A61K 31/136*    (2006.01)
(Continued)

(52) U.S. Cl.
CPC ............ *C07D 213/38* (2013.01); *A61K 31/13* (2013.01); *A61K 31/155* (2013.01);
(Continued)

(58) Field of Classification Search
CPC .... A61K 2300/00; A61K 31/18; A61K 31/33; A61K 31/34; A61K 31/4105;
(Continued)

(56) References Cited

U.S. PATENT DOCUMENTS 3,689,550 A    9/1972   Schellenbaum et al.
3,850,931 A    11/1974  Kim et al.
(Continued)

FOREIGN PATENT DOCUMENTS

BE    891537    4/1982
DE    670 584 C    1/1939
(Continued)

OTHER PUBLICATIONS

CAS Registry No. 1350126-66-7, entered STN Dec. 7, 2011.*
International Search Report and Written Opinion mailed Oct. 22, 2013 for Application No. PCT/US2013/052572.
International Preliminary Report on Patentability mailed Feb. 5, 2015 for Application No. PCT/US2013/052572.
Diao et al., Assembly of substituted 1H-benzimidazoles and 1,3-dihydrobenzimidazol-2-ones via CuI/L-proline catalyzed coupling of aqueous ammonia with 2-iodoacetanilides and 2-iodophenylcarbamates. J Org Chem. Oct. 16, 2009;74(20):7974-7. doi: 10.1021/jo9017183.
Foster, Deuterium Isotope Effects in the Metabolism of Drugs and Xenobiotics: Implications for Drug Design. Adv Drug Res. 1985;14:1-40.
Supplementary European Search Report dated Apr. 13, 2015 for Application No. EP 12775936.3.
(Continued)

*Primary Examiner* — Michael Barker
*Assistant Examiner* — Amanda L Aguirre
(74) *Attorney, Agent, or Firm* — Wolf, Greenfield & Sacks, P.C.

(57) ABSTRACT

The present invention relates to compounds of formula (I) or a pharmaceutically acceptable salt, hydrate, solvate, or prodrug thereof, wherein $X_1$, $X_2$, $X_3$, $X_4$, $X_5$, $W_1$, $W_2$, $W_3$, and $W_4$ are as described. The present invention relates generally to inhibitors of histone deacetylase and to methods of making and using them. In one aspect, the invention relates to selective HDAC3 inhibitors useful for protecting β-cells and improving insulin resistance. The selective HDAC3 inhibitors are also useful for promoting cognitive function and enhancing learning and memory formation. Compounds of the invention are useful for treating, alleviating, and/or preventing various conditions, including for example, a metabolic disorder such as type 1 or type 2 diabetes, dyslipidemias, lipodystrophies, liver disease associated with metabolic syndrome, polycystic ovarian syndrome, or obesity; inflammatory disease; neurological disorder; a memory or cognitive function disorder/impairment; an extinction learning disorder; fungal disease or infection; viral disease or infection such as HIV; hematological disease; liver disease; lysosomal storage disease; or neoplastic disease in humans or animals.

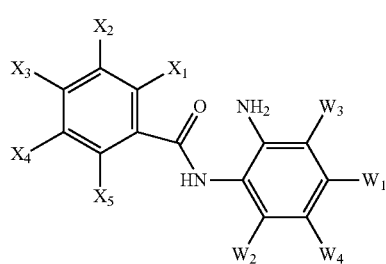

(I)

25 Claims, 21 Drawing Sheets

(51) Int. Cl.
*A61P 3/00* (2006.01)
*A61P 25/16* (2006.01)
*C07C 237/40* (2006.01)
*A61P 35/00* (2006.01)
*A61P 35/02* (2006.01)
*A61P 31/12* (2006.01)
*A61K 45/06* (2006.01)
*A61K 31/506* (2006.01)
*C07D 213/38* (2006.01)
*C07D 239/42* (2006.01)
*C07C 237/42* (2006.01)
*A61K 38/26* (2006.01)
*A61K 31/13* (2006.01)
*A61K 31/155* (2006.01)
*A61K 31/4439* (2006.01)
*A61K 31/445* (2006.01)
*A61K 31/4985* (2006.01)
*A61K 31/55* (2006.01)
*C07C 233/80* (2006.01)
*A61K 31/4406* (2006.01)

(52) U.S. Cl.
CPC .......... *A61K 31/167* (2013.01); *A61K 31/445* (2013.01); *A61K 31/4406* (2013.01); *A61K 31/4439* (2013.01); *A61K 31/4985* (2013.01); *A61K 31/506* (2013.01); *A61K 31/55* (2013.01); *A61K 38/26* (2013.01); *A61K 45/06* (2013.01); *C07C 233/80* (2013.01); *C07C 237/40* (2013.01); *C07C 237/42* (2013.01); *C07D 239/42* (2013.01)

(58) Field of Classification Search
CPC .. A61K 31/4415; A61K 31/13; A61K 31/155; A61K 31/167; A61K 31/4439; A61K 31/445; A61K 31/4985; A61K 31/55; A61K 31/506; A61K 31/343; A61K 31/4406; A61K 38/26; A61K 45/06; A61K 41/00; C07C 2101/02; C07C 233/80; C07C 237/40; C07C 259/10; C07C 2101/08; C07C 2101/14; C07C 233/44; C07C 235/56; C07C 235/64; C07C 237/42; C07C 259/06; C07C 271/22; C07C 271/26; C07C 271/28; C07C 275/24; C07C 323/42; C07C 323/44
USPC ........................................................ 564/184
See application file for complete search history.

(56) References Cited

U.S. PATENT DOCUMENTS

| | | |
|---|---|---|
| 4,404,356 A | 9/1983 | Andrews |
| 5,135,949 A | 8/1992 | von der Saal et al. |
| 5,137,918 A * | 8/1992 | Weiershausen ....... C07C 237/42 514/616 |
| 5,635,503 A | 6/1997 | Poindexter et al. |
| 5,783,522 A | 7/1998 | Schaefer et al. |
| 5,886,044 A | 3/1999 | Widdowson et al. |
| 6,645,990 B2 | 11/2003 | Askew et al. |
| 6,653,309 B1 | 11/2003 | Saunders et al. |
| 6,946,462 B2 | 9/2005 | Haag et al. |
| 7,550,490 B2 | 6/2009 | Lu et al. |
| 8,138,168 B1 | 3/2012 | Jones |
| 8,158,825 B2 | 4/2012 | Grimm et al. |
| 8,211,901 B2 | 7/2012 | Lu et al. |
| 8,450,525 B2 | 5/2013 | Rajagopal et al. |
| 8,598,168 B2 | 12/2013 | Moradei et al. |
| 8,957,066 B2 | 2/2015 | Jacques et al. |
| 9,265,734 B2 | 2/2016 | Rusche et al. |
| 9,365,498 B2 | 6/2016 | Holson et al. |
| 9,447,030 B2 | 9/2016 | Holson et al. |
| 2002/0173507 A1 | 11/2002 | Santora et al. |
| 2002/0193367 A1 | 12/2002 | Adam et al. |
| 2003/0027862 A1 | 2/2003 | Haning et al. |
| 2003/0159221 A1 | 8/2003 | Lang |
| 2003/0166639 A1 | 9/2003 | Adam et al. |
| 2006/0008517 A1 | 1/2006 | Lynch et al. |
| 2007/0054904 A1 | 3/2007 | Knolle et al. |
| 2008/0132503 A1 | 6/2008 | Moradei et al. |
| 2009/0118303 A1 | 5/2009 | Jikyo et al. |
| 2010/0009990 A1* | 1/2010 | Venkataramani .... C07D 403/04 514/242 |
| 2010/0216806 A1 | 8/2010 | Liang et al. |
| 2010/0298358 A1 | 11/2010 | Lu et al. |
| 2010/0324046 A1 | 12/2010 | Harrington et al. |
| 2014/0080800 A1 | 3/2014 | Holson et al. |
| 2014/0080802 A1 | 3/2014 | Holson et al. |
| 2014/0335550 A1 | 11/2014 | Zhang et al. |
| 2016/0251351 A1 | 9/2016 | Holson et al. |
| 2016/0272579 A1 | 9/2016 | Mazitschek et al. |
| 2016/0347761 A1 | 12/2016 | Holson et al. |

FOREIGN PATENT DOCUMENTS

| | | |
|---|---|---|
| DE | 1108213 | 6/1961 |
| DE | 2163381 | 7/1972 |
| EP | 0 196 005 A1 | 10/1986 |
| EP | 0 309 423 | 3/1989 |
| EP | 1 402 888 A1 | 3/2004 |
| GB | 2 086 905 A | 5/1982 |
| JP | 3-232868 A | 10/1991 |
| JP | 9-503748 A | 4/1997 |
| JP | 9-227495 A | 9/1997 |
| JP | 2004-521072 A | 7/2004 |
| JP | 2005-508311 A | 3/2005 |
| JP | 2005-522440 A | 7/2005 |
| JP | 2008-509075 A | 3/2008 |
| JP | 2008-094847 A | 4/2008 |
| JP | 2009-523726 A | 6/2009 |
| JP | 2009-536615 A | 10/2009 |
| JP | 2012-510512 A | 5/2012 |
| JP | 2012-518612 A | 8/2012 |
| WO | WO 01/70675 | 9/2001 |
| WO | WO 02/14311 A2 | 2/2002 |
| WO | WO 03/013484 | 2/2003 |
| WO | WO 03/066623 A1 | 8/2003 |
| WO | WO 2005/030705 A1 | 4/2005 |
| WO | WO 2006/016680 A1 | 2/2006 |
| WO | WO 2007/087130 A2 | 8/2007 |
| WO | WO 2007/118137 A1 | 10/2007 |
| WO | WO 2009/002534 A1 | 12/2008 |
| WO | WO 2009/076234 A2 | 6/2009 |
| WO | WO 2010/028192 | 3/2010 |
| WO | WO 2010/065117 A1 | 6/2010 |
| WO | WO 2010/094678 A1 | 8/2010 |
| WO | WO 2010/142426 A1 | 12/2010 |
| WO | WO 2011/053876 A1 | 5/2011 |
| WO | WO 2012/118782 A1 | 9/2012 |
| WO | WO 2012/149540 | 11/2012 |
| WO | WO 2015/134973 A1 | 9/2015 |

OTHER PUBLICATIONS

Office Communication dated May 30, 2016 for Application No. EP 12775936.3.
European Search Report dated Mar. 4, 2014 for Application No. EP 13194971.1.
Office Communication dated Jul. 15, 2015 for Application No. EP 13194971.1.
Japanese Office Action dated Oct. 14, 2015 for Application No. JP 2014-508179.
International Search Report and Written Opinion dated Jul. 20, 2012 for Application No. PCT/US2012/035814.
International Preliminary Report on Patentability dated Nov. 7, 2013 for Application No. PCT/US2012/035814.
European Office Communication for European Application No. 13745773.5 dated Dec. 21, 2016.

(56) References Cited

OTHER PUBLICATIONS

Alberini, Transcription factors in long-term memory and synaptic plasticity. Physiol Rev. Jan. 2009;89(1):121-45. doi: 10.1152/physrev.00017.2008.
Alenghat et al., Nuclear receptor corepressor and histone deacetylase 3 govern circadian metabolic physiology. Nature. Dec. 18, 2008;456(7224):997-1000. doi: 10.1038/nature07541.
Arts et al., Histone deacetylase inhibitors: from chromatin remodeling to experimental cancer therapeutics. Curr Med Chem. Nov. 2003;10(22):2343-50.
Banker et al., Modern Pharmaceutics, 3rd ed. Marcel Dekker. 1996;451, 596.
Bannister et al., Regulation of chromatin by histone modifications. Cell Res. Mar. 2011;21(3):381-95. doi: 10.1038/cr.2011.22.
Bantscheff et al., Chemoproteomics profiling of HDAC inhibitors reveals selective targeting of HDAC complexes. Nat Biotechnol. Mar. 2011;29(3):255-65. doi: 10.1038/nbt.1759.
Barrett et al., Beyond transcription factors: the role of chromatin modifying enzymes in regulating transcription required for memory. Learn Mem. Jun. 26, 2008;15(7):460-7. doi: 10.1101/lm.917508.
Blanchard et al., Histone deacetylase inhibitors: new drugs for the treatment of inflammatory diseases? Drug Discov Today. Feb. 1, 2005;10(3):197-204.
Bradner et al., Chemical genetic strategy identifies histone deacetylase 1 (HDAC1) and HDAC2 as therapeutic targets in sickle cell disease. Proc Natl Acad Sci U S A. Jul. 13, 2010;107(28):12617-22. doi: 10.1073/pnas.1006774107.
Broide et al., Distribution of histone deacetylases 1-11 in the rat brain. J Mol Neurosci. 2007;31(1):47-58.
Brukshtus et al., Synthesis of N-acetyl derivatives of 5-and 6-ethoxy-2 methylthiobenzimidazole and their cardiotonic activity. Chem Heterocyclic Compounds. Jun. 1, 1997;33(6):665-71.
Bunn, Pathogenesis and treatment of sickle cell disease. N Engl J Med. Sep. 11, 1997;337(11):762-9.
Chang et al., Differential response of cancer cells to HDAC inhibitors trichostatin A and depsipeptide. Br J Cancer. Jan. 3, 2012;106(1):116-25. doi: 10.1038/bjc.2011.532.
Charache et al., Effect of hydroxyurea on the frequency of painful crises in sickle cell anemia. Investigators of the Multicenter Study of Hydroxyurea in Sickle Cell Anemia. N Engl J Med. May 18, 1995;332(20):1317-22.
Chemical Abstracts STN Database Record for RN 1019377-02-6. May 6, 2008. 1 page.
Chemical Abstracts STN Database Record for RN 1038237-56-7. Aug. 3, 2008. 1 page.
Chemical Abstracts STN Database Record for RN 1095240-42-8. Jan. 22, 2009. 1 page.
Chemical Abstracts STN Database Record for RN 1152996-49-0. Jun. 7, 2009. 1 page.
Chemical Abstracts STN Database Record for RN 1153085-77-8. Jun. 7, 2009. 1 page.
Chemical Abstracts STN Database Record for RN 1154691-98-1. Jun. 9, 2009. 1 page.
Chemical Abstracts STN Database Record for RN 1156303-71-7. Jun. 12, 2009. 1 page.
Chemical Abstracts STN Database Record for RN 1182778-35-3. Sep. 11, 2009. 1 page.
Chemical Abstracts STN Database Record for RN 1262320-49-9. Feb. 8, 2011. 1 page.
Chemical Abstracts STN Database Record for RN 128691-95-2. Aug. 10, 1990. 1 page.
Chemical Abstracts STN Database Record for RN 157026-22-7. Aug. 16, 1994. 1 page.
Chemical Abstracts STN Database Record for RN 169604-52-8. Nov. 3, 1995. 1 page.
Chemical Abstracts STN Database Record for RN 22380-13-8. Nov. 16, 1984. 1 page.
Chemical Abstracts STN Database Record for RN 76280-05-2. Nov. 16, 1984. 1 page.
Chemical Abstracts STN Database Record for RN 865837-30-5. Oct. 24, 2005. 1 page.
Chemical Abstracts STN Database Record for RN 92614-21-3. Mar. 13, 2007. 1 page.
Chemical Abstracts STN Database Record for RN 926186-52-9. Mar. 13, 2007. 1 page.
Chemical Abstracts STN Database Record for RN 926189-39-1. Mar. 13, 2007. 1 page.
Chemical Abstracts STN Database Record for RN 926194-42-5. Mar. 13, 2007. 1 page.
Chemical Abstracts STN Database Record for RN 926196-62-5. Mar. 13, 2007. 1 page.
Chemical Abstracts STN Database Record for RN 926204-50-4. Mar. 13, 2007. 1 page.
Chemical Abstracts STN Database Record for RN 926206-09-9. Mar. 13, 2007. 1 page.
Chemical Abstracts STN Database Record for RN 926217-10-9. Mar. 13, 2007. 1 page.
Chemical Abstracts STN Database Record for RN 926219-65-0. Mar. 13, 2007. 1 page.
Chemical Abstracts STN Database Record for RN 926219-90-1. Mar. 13, 2007. 1 page.
Chemical Abstracts STN Database Record for RN 926233-05-8. Mar. 13, 2007. 1 page.
Chemical Abstracts STN Database Record for RN 926246-05-1. Mar. 13, 2007. 1 page.
Chemical Abstracts STN Database Record for RN 926247-11-2. Mar. 13, 2007. 1 page.
Chemical Abstracts STN Database Record for RN 926260-48-2. Mar. 13, 2007. 1 page.
Chemical Abstracts STN Database Record for RN 926260-89-1. Mar. 13, 2007. 1 page.
Chemical Abstracts STN Database Record for RN 926264-98-4. Mar. 13, 2007. 1 page.
Chemical Abstracts STN Database Record for RN 926272-49-3. Mar. 13, 2007. 1 page.
Chemical Abstracts STN Database Record for RN 937607-77-7. Jun. 17, 2007. 1 page.
Chemical Abstracts STN Database Record for RN 937619-64-2. Jun. 17, 2007. 1 page.
Chemical Abstracts STN Database Record for RN 937624-40-3. Jun. 17, 2007. 1 page.
Chemical Abstracts STN Database Record for RN 953731-76-5 Nov. 15, 2007. 1 page.
Chemical Abstracts STN Database Record for RN 953741-80-5. Nov. 15, 2007. 1 page.
Chemical Abstracts STN Database Record for RN 953747-99-4. Nov. 15, 2007. 1 page.
Chou et al., Pimelic diphenylamide 106 is a slow, tight-binding inhibitor of class I histone deacetylases. J Biol Chem. Dec. 19, 2008;283(51):35402-9. doi: 10.1074/jbc.M807045200.
Citrome, Schizophrenia and valproate. Psychopharmacol Bull. 2003;37 Suppl 2:74-88.
Dörwald, Chapter 1: Organic Synthesis: General Remarks. Side Reactions in Organic Synthesis. A Guide to Successful Synthesis Design. Wiley-VCH Verlag GmbH & Co. KGaA. 2005. 32 pages.
Fischer et al., Cyclin-dependent kinase 5 is required for associative learning. J Neurosci. May 1, 2002;22(9):3700-7.
Fischer et al., Recovery of learning and memory is associated with chromatin remodelling. Nature. May 10, 2007;447(7141):178-82.
Fischle et al., Enzymatic activity associated with class II HDACs is dependent on a multiprotein complex containing HDAC3 and SMRT/N-CoR. Mol Cell. Jan. 2002;9(1):45-57.
Glaser et al., Differential protein acetylation induced by novel histone deacetylase inhibitors. Biochem Biophys Res Commun. Dec. 17, 2004;325(3):683-90.
Guan et al., HDAC2 negatively regulates memory formation and synaptic plasticity. Nature. May 7, 2009;459(7243):55-60. doi: 10.1038/nature07925.
Guenther et al., A core SMRT corepressor complex containing HDAC3 and TBL1, a WD40-repeat protein linked to deafness. Genes Dev. May 1, 2000;14(9):1048-57.

(56) References Cited

OTHER PUBLICATIONS

Johannessen et al., Valproate: past, present, and future. CNS Drug Rev. 2003 Summer;9(2):199-216.

Karagianni et al., HDAC3: taking the SMRT-N-CoRrect road to repression. Oncogene. Aug. 13, 2007;26(37):5439-49.

Katsura et al., Studies on antiulcer drugs. II. Synthesis and antiulcer activities of imidazo[1,2-alpha]pyridinyl-2-alkylaminobenzoxazoles and 5,6,7,8-tetrahydroimidazo[1,2-alpha]pyridinyl derivatives. Chem Pharm Bull (Tokyo). Feb. 1992;40(2):371-80.

Kilgore et al., Inhibitors of class 1 histone deacetylases reverse contextual memory deficits in a mouse model of Alzheimer's disease. Neuropsychopharmacology. Mar. 2010;35(4):870-80. doi: 10.1038/npp.2009.197.

Kouzarides, Chromatin modifications and their function. Cell. Feb. 23, 2007;128(4):693-705.

Kreutzberger et al., Antiinflammatory Agents, VII: Aroylation of 5-Chlorobenzotriazole [Published in German as Entzündungshemmende Wirkstoffe, 7. Mitt. Aroylierung von 5-Chlorbenzotriazol]. Arch. Pharm. 1980;313(3): 255-259. doi: 10.1002/ardp.19803130311.

Langley et al., Remodeling chromatin and stress resistance in the central nervous system: histone deacetylase inhibitors as novel and broadly effective neuroprotective agents. Curr Drug Targets CNS Neurol Disord. Feb. 2005;4(1):41-50.

Lattal et al., Systemic or intrahippocampal delivery of histone deacetylase inhibitors facilitates fear extinction. Behav Neurosci. Oct. 2007;121(5):1125-31.

Leoni et al., The antitumor histone deacetylase inhibitor suberoylanilide hydroxamic acid exhibits anti-inflammatory properties via suppression of cytokines. Proc Natl Acad Sci U S A. Mar. 5, 2002;99(5):2995-3000.

Lettre et al., DNA polymorphisms at the BCL11A, HBS1L-MYB, and beta-globin loci associate with fetal hemoglobin levels and pain crises in sickle cell disease. Proc Natl Acad Sci U S A. Aug. 19, 2008;105(33):11869-74. doi: 10.1073/pnas.0804799105.

Letvin et al., Augmentation of fetal-hemoglobin production in anemic monkeys by hydroxyurea. N Engl J Med. Apr. 5, 1984;310(14):869-73.

Levenson et al., Regulation of histone acetylation during memory formation in the hippocampus. J Biol Chem. Sep. 24, 2004;279(39):40545-59.

Li et al., Both corepressor proteins SMRT and N-CoR exist in large protein complexes containing HDAC3. EMBO J. Aug. 15, 2000;19(16):4342-50.

Malvaez et al., Modulation of chromatin modification facilitates extinction of cocaine-induced conditioned place preference. Biol Psychiatry. Jan. 1, 2010;67(1):36-43. doi: 10.1016/j.biopsych.2009.07.032.

Marks et al., Histone deacetylase inhibitors. Adv Cancer Res. 2004;91:137-68.

Marks et al., Histone deacetylases and cancer: causes and therapies. Nat Rev Cancer. Dec. 2001;1(3):194-202.

Matsushita et al., Smart cleavage reactions: the synthesis of benzimidazoles and benzothiazoles from polymer-bound esters. Tetrahedron Letters. 2004;45:313-16.

Mcquown et al., HDAC3 is a critical negative regulator of long-term memory formation. J Neurosci. Jan. 12, 2011;31(2):764-74. doi: 10.1523/JNEUROSCI.5052-10.2011.

Menzel et al., A QTL influencing F cell production maps to a gene encoding a zinc-finger protein on chromosome 2p15. Nat Genet. Oct. 2007;39(10):1197-9.

Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8. doi: 10.1016/j.bmcl.2007.12.031. Epub Jan. 7, 2008.

Miller et al., Histone deacetylase inhibitors. J Med Chem. Nov. 20, 2003;46(24):5097-116.

Monfils et al., Extinction-reconsolidation boundaries: key to persistent attenuation of fear memories. Science. May 15, 2009;324(5929):951-5. doi: 10.1126/science.1167975.

Platt et al., Hydroxyurea enhances fetal hemoglobin production in sickle cell anemia. J Clin Invest. Aug. 1984;74(2):652-6.

Rai et al., Two new pimelic diphenylamide HDAC inhibitors induce sustained frataxin upregulation in cells from Friedreich's ataxia patients and in a mouse model. PLoS One. Jan. 21, 2010;5(1):e8825. doi: 10.1371/journal.pone.0008825.

Roozendaal et al., Membrane-associated glucocorticoid activity is necessary for modulation of long-term memory via chromatin modification. J Neurosci. Apr. 7, 2010;30(14):5037-46. doi: 10.1523/JNEUROSCI.5717-09.2010.

Sankaran et al., Developmental and species-divergent globin switching are driven by BCL11A. Nature. Aug. 27, 2009;460(7259):1093-7. doi: 10.1038/nature08243.

Sankaran et al., Human fetal hemoglobin expression is regulated by the developmental stage-specific repressor BCL11A. Science. Dec. 19, 2008;322(5909):1839-42. doi: 10.1126/science.1165409.

Schultz et al., Kinetics and comparative reactivity of human class I and class IIb histone deacetylases. Biochemistry. Aug. 31, 2004;43(34):11083-91.

Song et al., Synthesis of New Crown Ethers Containing Appended Pyridine, 10-hydroxybenzoquinoline, 8-hydroxyquinoline and 2-amino-1-hydroxybiphenyl Sidearms. Supramolecular Chemistry. 2002;14(2-3):263-269.

Stefanko et al., Modulation of long-term memory for object recognition via HDAC inhibition. Proc Natl Acad Sci U S A. Jun. 9, 2009;106(23):9447-52. doi: 10.1073/pnas.0903964106.

Steinberg et al., Effect of hydroxyurea on mortality and morbidity in adult sickle cell anemia: risks and benefits up to 9 years of treatment. JAMA. Apr. 2, 2003;289(13):1645-51. Erratum in: JAMA. Aug. 13, 2003;290(6):756.

Steinberg, Management of sickle cell disease. N Engl J Med. Apr. 1, 1999;340(13):1021-30.

Suuronen et al., Regulation of microglial inflammatory response by histone deacetylase inhibitors. J Neurochem. Oct. 2003;87(2):407-16.

Tsankova et al., Sustained hippocampal chromatin regulation in a mouse model of depression and antidepressant action. Nat Neurosci. Apr. 2006;9(4):519-25.

Turconi et al., Synthesis of a New Class of 2,3-Dihydro-2-oxo-1H-benzimidazole-1-carboxylic Acid Derivatives as Highly Potent 5-$HT_3$ Receptor Antagonists. J Med Chem. 1990;33:2101-8.

Uda et al., Genome-wide association study shows BCL11A associated with persistent fetal hemoglobin and amelioration of the phenotype of beta-thalassemia. Proc Natl Acad Sci U S A. Feb. 5, 2008;105(5):1620-5. doi: 10.1073/pnas.0711566105.

Vecsey et al., Histone deacetylase inhibitors enhance memory and synaptic plasticity via CREB:CBP-dependent transcriptional activation. J Neurosci. Jun. 6, 2007;27(23):6128-40.

Wagner et al., An Isochemogenic Set of Inhibitors To Define the Therapeutic Potential of Histone Deacetylases in β-Cell Protection. ACS Chem Biol. Feb. 19, 2016;11(2):363-74. doi: 10.1021/acschembio.5b00640.

Wagner et al., Small molecule inhibitors of zinc-dependent histone deacetylases. Neurotherapeutics. Oct. 2013;10(4):589-604. doi: 10.1007/s13311-013-0226-1.

Weïwer et al., Therapeutic potential of isoform selective HDAC inhibitors for the treatment of schizophrenia. Future Med Chem. Sep. 2013;5(13):1491-508. doi: 10.4155/fmc.13.141.

Wolff, Burger's Medicinal Chemistry, 5th ed. Part I. John Wiley & Sons. 1995;975-7.

\* cited by examiner

A linear trend indicates a competitive binding mechanism

Compound1 binding constant was estimated from protection experiment against HDAC1 inactivation A linear trend indicates a competitive binding mechanism

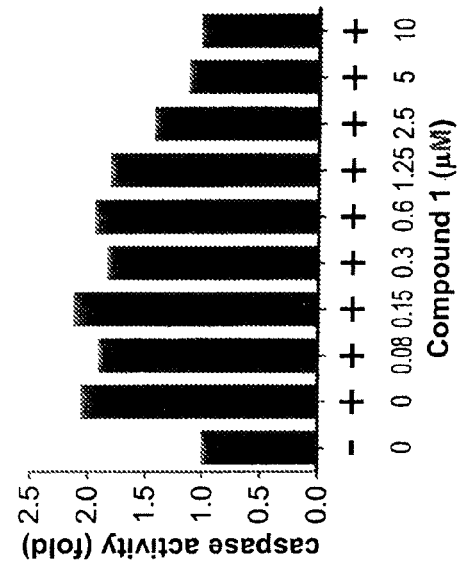
FIG. 9A
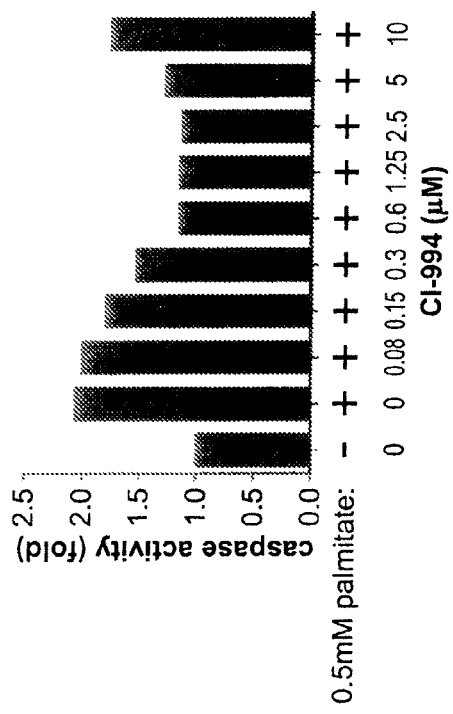
FIG. 9B
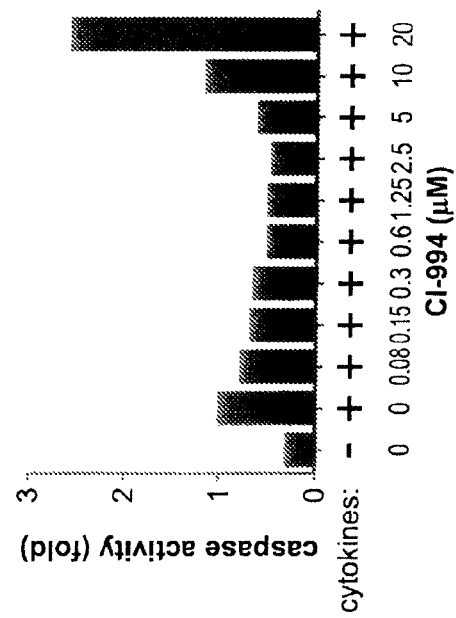
FIG. 9C
FIG. 9D

INHIBITORS OF HISTONE DEACETYLASE

This application is a national stage filing under 35 U.S.C. §371 of International PCT Application No. PCT/US2013/052572, filed Jul. 29, 2013, entitled "INHIBITORS OF HISTONE DEACETYLASE", which claims the benefit under 35 U.S.C. §119(e) to U.S. Provisional Application No. 61/676,496, filed Jul. 27, 2012, entitled "INHIBITORS OF HISTONE DEACETYLASE", each of which is hereby incorporated by reference in its entirety.

GOVERNMENT SUPPORT

This invention was made with government support under Grant No. DP2-DK083048 awarded by the National Institutes of Health. The government has certain rights in the invention.

FIELD OF THE INVENTION

The present invention relates generally to inhibitors of histone deacetylase and to methods of making and using them. These compounds are useful for treating, alleviating, and/or preventing metabolic disorders such as dyslipidemias, lipodystrophies, liver diseases associated with metabolic syndrome, obesity, diabetes, polycystic ovarian syndrome, and inflammation. The compounds of the invention protect β-cells and improve insulin resistance. Compounds of the invention are also useful for promoting cognitive function and enhancing learning and memory formation. As a result, these compounds are useful for treating, alleviating, and/or preventing various conditions, including for example, neurological disorders, memory and cognitive function disorders/impairments, and extinction learning disorders. The compounds of the invention are also useful against fungal diseases and infections, viral diseases and infections such as an HIV infection, inflammatory diseases, hematological diseases, lysosomal storage diseases, liver diseases, and neoplastic diseases in humans and animals.

BACKGROUND OF THE INVENTION

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs (Marks, P. et al., Nat. Rev. Cancer, 1, 194-202, (2001); and Marks, P. et al., Adv. Cancer Res, 91, 137-168, (2004)). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. (Langley, B. et al., Curr. Drug Targets CNS Neurol. Disord., 4, 41-50, (2005)). A recent review has summarized the evidence that aberrant histone acetyltransferase (HAT) and histone deacetylases (HDAC) activity may represent a common underlying mechanism contributing to neurodegeneration. HDAC activity has also been reported to contribute to long-term memory formation (Alarcon, Neuron, 42, 947-959, 2004). Moreover, using a mouse model of depression, Nestler has recently highlighted the therapeutic potential of histone deacetylation inhibitors (HDAC5) in depression (Tsankova, N. M. et al., Nat. Neurosci., 9, 519-525, (2006)). HDAC inhibition has been reported as having an effect in a variety of metabolic disorders (Pipalia, et al., PNAS, early release, approved Feb. 24, 2011; Li, et al., Diabetes, 61, 797-806 (2012); Lu, et al., PNAS, 108, 21200-21205 (2011)). The inhibition of HDAC3 has been shown to protect beta cells from cytokine-induced apoptosis (Chou, D H, et al. Chemistry & biology 19, 669-673 (2012)). Histone deacetylases 1 and 3 but not 2 have been shown to mediate cytokine-induced beta cell apoptosis in INS-1 cells and dispersed primary islets from rats and are differentially regulated in the islets of type 1 diabetic children (Lundh, M, et al., Diabetologia 55, 2421-2431 (2012)). The inhibition of HDAC3 has also been reported as having a role in activating latent HIV-1 (Huber, et al., J. Bio. Chem. 286, 25, 22211-22218 (2011)).

There are 18 known human histone deacetylases, grouped into four classes based on the structure of their accessory domains. Class I includes HDAC1, HDAC2, HDAC3, and HDAC8 and has homology to yeast RPD3. HDAC4, HDAC5, HDAC7, and HDAC9 belong to class IIa and have homology to yeast HDA1. HDAC6 and HDAC10 contain two catalytic sites and are classified as class IIb. Class III (the sirtuins) includes SIRT1, SIRT2, SIRT3, SIRT4, SIRT5, SIRT6, and SIRT7. HDAC11 is another recently identified member of the HDAC family and has conserved residues in its catalytic center that are shared by both class I and class II deacetylases and is sometimes placed in class IV.

There is still much to be understood about the family of HDACs, including the varying functions of different HDACs and the range of HDAC substrates. In order to learn more about the role that the individual HDACs play, it is important to develop compounds with binding selectivity for individual HDAC isoforms or for subsets of HDAC isoforms. While some degree of isoform selectivity has been shown by a few compounds, this problem of identifying selective inhibitors is far from solved, and the problem is complicated by the interactions of the HDACs with each other as well as other proteins (cofactors) that can possibly alter their interaction with various inhibitors (Glaser, et al., Biochem. Biophys. Res. Commun., 325, 683-690 (2004)).

Recent results indicate that HDAC3 is a critical negative regulator of long-term memory formation and may play a critical role in the molecular mechanisms underlying long-term memory formation. It has been demonstrated that knockout of HDAC3 in the brain of mice enhanced learning and memory and that administration of an HDAC3 selective compound (RGFP106) also enhanced learning and memory in mice (McQuown, S. C., et al., HDAC3 is a critical regulator of long-term memory formation. The Journal of Neuroscience, 31(1)(2011), 764-774)(see also, McQuown, Neurobiol. Learn. Mem. 2011, 96(1): 27-34 and WO 2012/016081). Despite the clinical efficacy of HDAC inhibitors, treatment of patients with HDAC inhibitors results in undesirable hematological side effects, such as anaemia and thrombocytopenia (loss of platelets). Side effects of HDAC inhibitors may be due to the targeting of (multiple) HDACs. For example, the dual knockdown of HDAC1 and 2 together has been shown to be involved in the mechanistic basis for thrombocytopenia (Wilting, R. H. et al., Overlapping functions of HDAC1 and HDAC2 in cell cycle regulation and haematopoiesis, EMBO Journal. (2010) 29, 1586-1597). The dose limiting toxicity of CI-994, a compound that inhibits HDAC1, HDAC2 and HDAC3, in humans is thrombocytopenia. It has also been shown that CI-994 is cytotoxic to megakaryocytes, the progenitor cell for platelets, presumably via inhibition of HDAC1 and HDAC2 (Volpe, D. A. et al, In vitro and in vivo effects of acetyldinaline on murine megakaryocytopoiesis. Cancer Chemother. Pharmacol. (2004) 54, 89-94).

HDAC inhibitors have great therapeutic potential. However, there is a need to identify specific and selective HDAC inhibitors e.g., selective HDAC3 inhibitors to identify the structural features required for potent HDAC inhibitory activity and define the relevant HDAC isoforms to target in specific disease indications. Clinically, the optimal dose, timing and duration of therapy, as well as the most appropriate agents to combine with HDAC inhibitors, are also still to be defined.

SUMMARY OF THE INVENTION

The present invention provides compounds useful for the inhibition of histone deacetylase (HDAC). The invention provides a compound having the formula I:

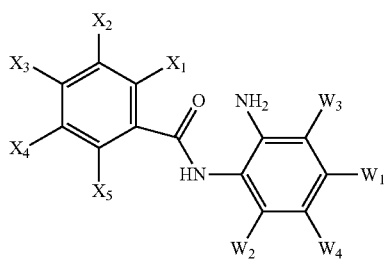

or a pharmaceutically acceptable salt, hydrate, solvate, or prodrug thereof. In the formula, the variables $X_1, X_2, X_3, X_4, X_5, W_1, W_2, W_3$, and $W_4$ can be selected from the respective groups of chemical moieties later defined in the detailed description.

In addition, the invention provides pharmaceutical compositions comprising an effective amount of a compound of the invention and a pharmaceutical carrier, diluent, or excipient.

In one aspect, the invention provides a method of treating, alleviating, and/or preventing a condition in a subject comprising administering to a subject in need thereof an effective amount of a compound of the invention or a pharmaceutically acceptable salt, hydrate, solvate or prodrug thereof. In one aspect, the condition is selected from a metabolic disorder such as diabetes (type 1 or type 2), dyslipidemia, lipodystrophy, liver disease, polycystic ovarian syndrome, or obesity; inflammatory disease; neurological disorder; memory or cognitive function disorder or impairment; extinction learning disorder; fungal disease or infection; a viral disease or infection such as an HIV infection; hematological disease; lysosomal storage disease; and neoplastic disease.

In one aspect, the invention provides a method of treating, alleviating, and/or preventing memory loss or impairment in a subject comprising administering to the subject in need thereof an effective amount of a compound of the invention or a pharmaceutically acceptable salt, hydrate, solvate, or prodrug thereof.

In one aspect, the invention provides a method of treating, alleviating, and/or preventing a cognitive function disorder or impairment in a subject in need thereof comprising administering to the subject an effective amount of a compound of the invention or a pharmaceutically acceptable salt, hydrate, solvate, or prodrug thereof. In one aspect, the cognitive function disorder or impairment is associated with Alzheimer's disease, Huntington's disease, seizure induced memory loss, schizophrenia, Rubinstein Taybi syndrome, Rett Syndrome, Fragile X, Lewy body dementia, vascular dementia, Parkinson's disease, ADHD, dyslexia, bipolar disorder and social, cognitive and learning disorders associated with autism, traumatic head injury, or attention deficit disorder. In one aspect, the cognitive function disorder or impairment is associated with an anxiety disorder, conditioned fear response, panic disorder, obsessive compulsive disorder, post-traumatic stress disorder, phobia, social anxiety disorder, substance dependence recovery or Age Associated Memory Impairment (AAMI), or Age Related Cognitive Decline (ARCD).

In one aspect, the invention provides a method of treating, alleviating, and/or preventing an inflammatory disease in a subject in need thereof comprising administering to the subject an effective amount of a compound or a pharmaceutically acceptable salt, hydrate, solvate, or prodrug thereof.

In one aspect, the invention provides a method of treating, alleviating, and/or preventing a fungal disease or infection in a subject in need thereof comprising administering to the subject an effective amount of a compound of the invention or a pharmaceutically acceptable salt, hydrate, solvate, or prodrug thereof.

In one aspect, the invention provides a method of treating, alleviating, and/or preventing a viral disease or infection in a subject in need thereof comprising administering to the subject an effective amount of a compound of the invention or a pharmaceutically acceptable salt, hydrate, solvate, or prodrug thereof. In one aspect, the viral infection is an HIV infection. In one aspect, the viral infection is a latent infection. In a further aspect, the viral infection is a latent HIV infection.

In one aspect, the invention provides a method of potentiate dopaminergic signaling. In one aspect, the invention provides a method of treating, alleviating, and/or preventing a dopaminergic-based neurodegenerative disorders. In one aspect, the disorder is Parkinson's disease. In one aspect, the disorder is Huntington's disease.

In one aspect, the invention provides a method of treating, alleviating, and/or preventing a hematological disease in a subject comprising administering to the subject in need thereof an effective amount of a compound of the invention or a pharmaceutically acceptable salt, hydrate, solvate, or prodrug thereof. In one aspect, the hematological disease is selected from acute myeloid leukemia, acute promyelocytic leukemia, acute lymphoblastic leukemia, chronic myelogenous leukemia, myelodysplastic syndromes, and sickle cell anemia. In one aspect, the hematological disease is sickle cell anemia.

In one aspect, the invention provides a method of treating, alleviating, and/or preventing a neoplastic disease in a subject comprising administering to the subject in need thereof an effective amount of a compound of the invention or a pharmaceutically acceptable salt, hydrate, solvate, or prodrug thereof. In one aspect, the neoplastic disease is cancer.

In one aspect, the invention provides a method of treating, alleviating, and/or preventing a psychiatric disease (depression, mood, mania disorders etc.) in a subject comprising administering to the subject in need thereof an effective amount of a compound of the invention or a pharmaceutically acceptable salt, hydrate, solvate, or prodrug thereof.

In one aspect, the invention provides a method of treating, alleviating, and/or preventing a metabolic disorder in a subject comprising administering to the subject in need thereof an effective amount of a compound of the invention or a pharmaceutically acceptable salt, hydrate, solvate, or prodrug thereof. In one aspect, the metabolic disorder is obesity. In one aspect, the metabolic disorder is Gaucher disease. In one aspect, the metabolic disorder is Niemann-Pick type C disease. In one aspect, the metabolic disorder is liver disease associated with metabolic syndrome.

In one aspect, the invention provides a method of treating, alleviating, and/or preventing a liver disease in a subject comprising administering to the subject in need thereof an effective amount of a compound of the invention or a pharmaceutically acceptable salt, hydrate, solvate, or prodrug thereof. In one aspect, the liver disease is liver heptosteatosis. In one aspect, the liver disease is fatty liver disease. In one aspect, the liver disease is NASH (Non-alcoholic steatohepatitis). In one aspect, the liver disease is NAFLD (Non-alcoholic fatty liver disease).

In one aspect, the invention the invention provides a method of treating, alleviating, and/or preventing diabetes in a subject comprising administering to the subject in need thereof an effective amount of a compound of the invention or a pharmaceutically acceptable salt, hydrate, solvate, or prodrug thereof. In one aspect, the diabetes is type 1 diabetes. In one aspect, the diabetes is type 2 diabetes.

In one aspect, the invention provides a method of treating, alleviating, and/or preventing dyslipidemia in a subject comprising administering to the subject in need thereof an effective amount of a compound of the invention or a pharmaceutically acceptable salt, hydrate, solvate, or prodrug thereof.

In one aspect, the invention provides a method of treating, alleviating, and/or preventing lipodystrophy in a subject comprising administering to the subject in need thereof an effective amount of a compound of the invention or a pharmaceutically acceptable salt, hydrate, solvate, or prodrug thereof. In one aspect, the lipodystrophy is HIV-associated lipodystrophy.

In one aspect, the invention provides a method, wherein the method is a combination therapy further comprising administering to the subject (1) a pharmaceutically active ingredient or exposing the subject to (2) cognitive behavioral therapy (CBT), (3) psychotherapy, (4) behavioral exposure treatments, (5) virtual reality exposure (VRE) or (6) cognitive remediation therapy or (7) any combination thereof.

In one aspect, the invention provides a combination therapy for treating, alleviating, and/or preventing post-traumatic stress disorder (PTSD) or Alzheimer's disease in a subject comprising administering to the subject in need thereof an effective amount of (1) a compound of the invention or a pharmaceutically acceptable salt, hydrate, solvate, or prodrug thereof and (2) a pharmaceutically active ingredient administered selected from Aricept®, memantine, and galantamine.

In one aspect, the invention provides a combination therapy for treating, alleviating, and/or preventing diabetes (type 1 and/or type 2) in a subject comprising administering to the subject in need thereof an effective amount of (1) a compound of the invention or a pharmaceutically acceptable salt, hydrate, solvate, or prodrug thereof and (2) an antidiabetic drug. The antidiabetic drug is a biguanide such as metformin, a thiazolidinedione such as rosiglitazone, an incretin mimetic such as exenatide, a dipeptidyl peptidase-4 inhibitors such as sitagliptin or injected insulin.

In one aspect, the invention provides a method of treating extinction learning disorders in a subject in need thereof comprising administering to the subject an effective amount of a compound of the invention or a pharmaceutically acceptable salt, hydrate, solvate, or prodrug thereof. In one aspect, the extinction learning disorder is fear extinction deficit. In one aspect, the extinction learning disorder is post-traumatic stress disorder. In one aspect, the method is a combination therapy for treating extinction learning disorders in a subject in need thereof comprising administering to the subject (1) an effective amount of a compound of the invention or a pharmaceutically acceptable salt, hydrate, solvate, or prodrug thereof and (2) exposing the subject to cognitive behavioral therapy (CBT), psychotherapy, behavioral exposure treatments, virtual reality exposure (VRE) or cognitive remediation therapy.

In one aspect, the invention provides a method of treating, alleviating, and/or preventing a lysosomal storage disease in a subject comprising administering to the subject in need thereof an effective amount of a compound of the invention or a pharmaceutically acceptable salt, hydrate, solvate, or prodrug thereof.

In one aspect, the invention provides a method wherein the compound of the invention or a pharmaceutically acceptable salt, hydrate, solvate, or prodrug thereof is administered by a route selected from oral, parenteral, intramuscular, intranasal, sublingual, intratracheal, inhalation, ocular, vaginal, rectal, and intracerebroventricular.

In one aspect, the invention provides a method, wherein the subject is a human.

In one aspect, the invention provides a method of synthesizing a compound of the invention or a pharmaceutically acceptable salt, hydrate, solvate, or prodrug thereof.

In one aspect, the invention provides a kit containing one or more compounds of the invention or a pharmaceutically acceptable salt, hydrate, solvate, or prodrug thereof. In one aspect, the kit further contains a pharmaceutically active ingredient.

BRIEF DESCRIPTION OF THE FIGURES

FIG. 9 is a series of 4 bar graphs. FIGS. 9A and 9B show a dose-response analysis of CI-994 and compound 1 in suppression of palmitate induced beta-cell apoptosis. FIGS. 9C and 9D show a dose-response analysis of CI-994 and compound 1 in suppression of cytokine-induced beta-cell apoptosis.

FIG. 10 is a series of bar graphs.

FIG. 13 is a series of bar graphs.

FIG. 14 is a series of bar graphs which show 10 μM compound 1 reduces endoplasmic reticulum (ER) stress by reducing CHOP expression and JNK phosphorylation.

FIG. 16 is a series of bar graphs.

DETAILED DESCRIPTION OF THE INVENTION

Figure 1:
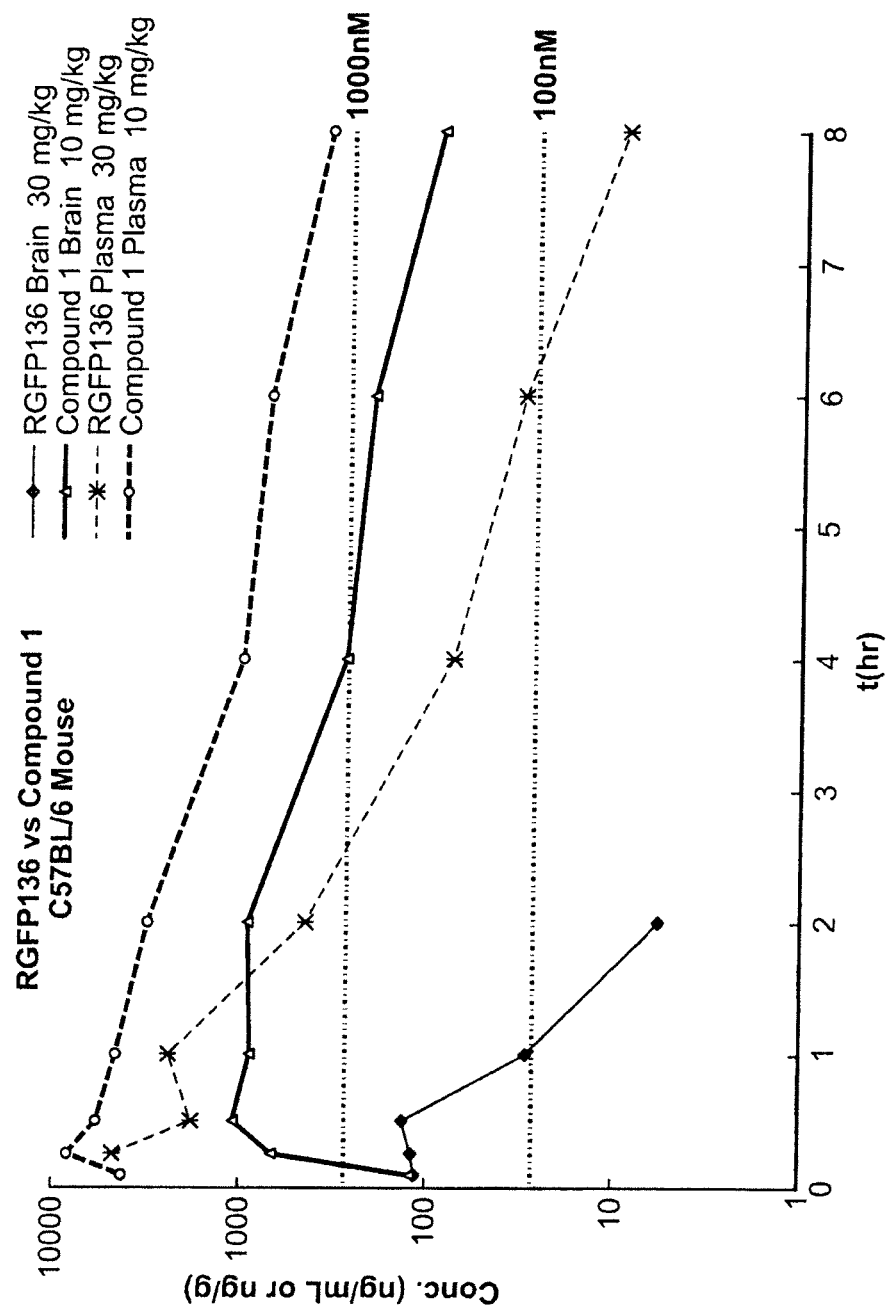
FIG. 1 is a graph which shows a comparison of the exposure over time of Repligen 136 and compound 1 in brain and plasma (Example 2).

The invention provides compounds, pharmaceutical compositions and methods for inhibiting class I histone deacetylase enzymatic activity. The invention provides compounds, pharmaceutical compositions and methods for selective inhibition of HDAC 3 activity. The invention also provides compounds, pharmaceutical compositions and methods for protecting β-cells and improving insulin resistance, promoting cognitive function and treating, alleviating and/or preventing various conditions e.g., metabolic disorders such as diabetes (type 1 or type 2), dyslipidemia, lipodystrophy, polycystic ovarian syndrome, liver disease, or obesity, inflammatory diseases, neurological disorders, memory and cognitive function disorders/impairments, extinction learning disorders, fungal diseases or infections, viral diseases or infections such as HIV, hematological diseases, lysosomal storage disease, and neoplastic diseases. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties that have from 1, 2, 3, or 4 carbon atoms including methyl, ethyl, n-propyl, and n-butyl. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. The term "$C_3$-$C_8$ cycloalkyl" also includes cyclooctyl. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted as specified herein.

The term "$C_4$-$C_8$ cycloalkenyl" refers cyclobutenyl, cyclopentyl, cyclohexenyl, cycloheptenyl, and cyclooctenyl rings having one or more sites of unsaturation e.g., one or more double bonds.

The term "3 to 8 membered ring" includes a 3, 4, 5, 6, 7, and 8-membered ring.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom.

The term "halogen" refers to fluoro, chloro, bromo, or iodo.

The term "hydroxyl" means OH.

The term "aryl" or "aromatic ring" alone or in combination, means a carbocyclic aromatic system containing one, two or three rings wherein such rings may be attached together in a pendent manner or may be fused. The term "aryl" or "aromatic ring" embraces aromatic radicals such as phenyl ($C_6H_6$), naphthyl, tetrahydronapthyl, indane and biphenyl, and includes carbocyclic aryl, and biaryl groups, all of which may be optionally substituted.

The term "heteroaryl" or "heteroaromatic ring" as used herein includes 5-, 6- and 7-membered single-ring aromatic groups that may include from 1, 2, 3, or 4 heteroatoms, for example, pyrrole, furan, thiophene, imidazole, oxazole, thiazole, triazole, pyrazole, pyridine, pyrazine, pyridazine, azepine, oxepine, oxazine, triazine and pyrimidine, and the like. Those aryl groups having heteroatoms in the ring structure may also be referred to as "aryl heterocycles" or "heteroaromatics." The aromatic and heteroaromatic rings can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like.

The term "heterocyclic ring" or "heterocycle" is taken to mean a saturated, unsaturated, or partially unsaturated containing from 1, 2, 3, or 4 heteroatoms selected from nitrogen, oxygen and sulfur, said ring optionally being benzofused. A heterocyclic ring can be multicyclic e.g., bicyclic or tricyclic. The term "3- to 8-membered heterocyclic ring" refers to a ring having from 3, 4, 5, 6, 7 or 8 atoms. The term "3- to 6-membered heterocyclic ring" refers to a ring having from 3, 4, 5, or 6 atoms. The term "5- to 6-membered heterocyclic ring" refers to a ring having 5 or 6 atoms. Exemplary heterocyclic rings, for the purposes of the present invention, include furanyl, thiophenyl (thienyl or thiopheneyl), pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Heterocyclic rings include bicyclic rings for example, 3-azabicyclo[3.1.0]hexane, 8-oxa-3-azabicyclo[3.2.1]octane. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted, which also of course includes optionally substituted on the benzo ring when the heterocycle is benzofused.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds unless otherwise specified. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient(s) and salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

The term "acid addition salt" refers to a salt of a compound of the invention prepared by reaction of a compound of the invention with a mineral or organic acid. For exemplification of pharmaceutically acceptable acid addition salts see, e.g., Berge, S. M, Bighley, L. D., and Monkhouse, D. C., *J. Pharm. Sci.*, 66:1, 1977. Compounds of this invention which are amines, are basic in nature and accordingly react with any of a number of inorganic and organic acids to form pharmaceutically acceptable acid addition salts.

Pharmaceutically acceptable acid addition salts of the invention can be formed by the reaction of a compound of the invention with an equimolar or excess amount of acid. Alternatively, hemi-salts can be formed by the reaction of a compound of the invention with the desired acid in a 2:1 ratio, compound to acid. The reactants are generally combined in a mutual solvent such as diethylether, tetrahydrofuran, methanol, ethanol, isopropanol, benzene, or the like. The salts normally precipitate out of solution within about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, 3-hydroxybutyrate, glycollate, tartrate, methanesulfonate, propanesulfonate, naphthalene-1-sulfonate, naphthalene-2-sulfonate, mandelate and the like.

Some of the compounds of the present invention may exist in unsolvated as well as solvated forms such as, for example, hydrates.

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the compounds of the invention, methods of delivering the same and compositions containing the same. "Prodrugs" are intended to include any covalently bonded carriers that release an active parent drug of the present invention in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the invention wherein a hydroxyl or amino, group is bonded to any group that, when the prodrug of the present invention is administered to a mammalian subject, it cleaves to form a free hydroxyl or free amino group, respectively. Examples of prodrugs include, but are not limited to, acetate, formate, and benzoate derivatives of alcohol and amine functional groups in the compounds of the present invention.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "suitable solvent" refers to any solvent, or mixture of solvents, inert to the ongoing reaction that sufficiently solubilizes the reactants to afford a medium within which to effect the desired reaction.

The compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention. Furthermore, the invention also includes metabolites of the compounds described herein.

The invention also comprehends isotopically-labeled compounds, which are identical to those recited in the formulae of the invention, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$, $^2H$ and $^{18}F$.

Compounds of the present invention and salts, hydrates, solvates or prodrugs of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., 3H, and carbon-14, i.e., $^{14}C$, isotopes are particularly preferred for their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances, isotopically labeled compounds of this invention can generally be prepared by carrying out the procedures disclosed in the Schemes and/or in the Examples below, by substituting a readily available isotopically labeled reagent for a non-isotopically labeled reagent. In one embodiment, the compounds of the invention, salts, hydrates, solvates, or prodrugs thereof are not isotopically labelled.

When any variable (e.g., $R^x$) occurs more than one time in any constituent or formula for a compound, its definition at each occurrence is independent of its definition at every other occurrence. Thus, for example, if a group is shown to be substituted with one or more $R^x$ moieties, then $R^x$ at each occurrence is selected independently from the definition of $R^x$. Also, combinations of substituents and/or variables are permissible, but only if such combinations result in stable compounds within a designated atom's normal valency.

As used herein, the compound "Repligen 136" is also known as RGFP136 or [N-(6-(2-amino-4-fluorophenylamino)-6-oxohexyl)-4-methylbenzamide].

As used herein, the compound CI-994 is also known as 4-(Acetylamino)-N-(2-aminophenyl)benzamide, acetyldinaline, 5'-Deoxy-5-fluoro-N-((pentyloxy)carbonyl)cytidine, Goe 5549, Go 5549, PD 123654, and Tacedinaline.

As used herein, the compound MS-275 is also known as Entinostat and SNDX-275.

As used herein, the compound SAHA is also known as suberoylanilide hydroxamic acid, Vorinostat, Zolinza, and N1-hydroxy-N8-phenyl-octanediamide.

As used herein, the term "treat," "treating," "alleviate," or "alleviating" herein, is meant decreasing the symptoms, markers, and/or any negative effects of a condition in any appreciable degree in a patient who currently has the condition. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one aspect, the subject is a human. Such subject can be considered to be in need of treatment with an HDAC inhibitor.

As used herein, "unsaturated" refers to compounds or structures having at least one degree of unsaturation (e.g., at least one double or triple bond).

As used herein, the term "a compound of the invention" includes a compound of any of formulae I, IA, IB, IC, II, IIA, IIB, III, IIIA, IIIB, IV, IVA, IVB, V, or VA, or any compound explicitly disclosed herein. In one aspect, a compound of the invention is not a compound of formulae IIIC or IVC.

As used herein, the term "negative control" is a compound that is not for use as a therapeutic but rather it is a compound for use in in vitro or in vivo assays to develop therapeutic HDAC inhibitors. A negative control compound retains many of the chemical structural features of an HDAC inhibitor but has no HDAC inhibitory activity.

The problem to be solved by the present invention is the identification of novel compounds for treating, alleviating or preventing various conditions, including but not limited to metabolic disorders such as type 1 or type 2 diabetes, dyslipidemia, lipodystrophy, polycystic ovarian syndrome, liver disease, or obesity, inflammatory diseases, neurological disorders, memory and cognitive function disorders/impairments, extinction learning disorders, fungal diseases and infections, viral diseases and infections such as HIV infection, hematological diseases, and lysosomal storage diseases. In one aspect, invention provides compounds that are potent, selective HDAC3 inhibitors. In one aspect, the invention provides compounds that possess thermodynamic and kinetic binding selectivity for HDAC3 over HDAC1 and HDAC2 and HDACs 4, 5, 6, 7, 8 and 9. While there are HDAC inhibitors in the clinic, most of these do not show significant selectivity for an individual HDAC isoform. Non-selective HDAC inhibitors may be associated with adverse effects. For example, some non-selective inhibitors are believed to be associated with undesirable hematological side effects, such as anemia and thrombocytopenia (loss of platelets). Other adverse side effects related to non-selective HDAC inhibition include fatigue, anorexia, and GI-toxicity. The invention provides the solution of new compounds and their use. In some instances, the compounds are fluorinated. The compounds described herein have one or more of the following advantages: improved isoform specificity, improved potency, improved selectivity for an individual HDAC isoform, extended residence time for an individual HDAC isoform, differential binding kinetics for individual HDAC isoform, a larger therapeutic window, reduced toxicities, increased tolerability at higher doses and exposures and/or a superior pharmacokinetic profile such as a higher Cmax, higher AUC, longer half-life, and/or sustained exposure in the plasma or brain. The advantageous effects of the compounds of the invention allow for the effective treatment of diseases, which were not treatable prior to the present invention with non-selective HDAC inhibitors due to their high toxicity.

Compounds of the Invention

In one aspect, the invention provides a compound of formula I:

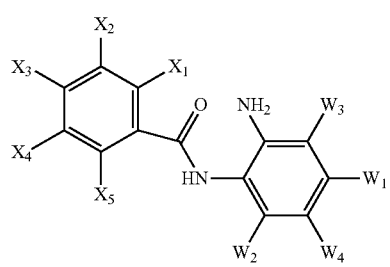

(I)

or a pharmaceutically acceptable salt, hydrate, solvate, or prodrug thereof, wherein $W_1$, $W_2$, $W_3$, and $W_4$ are each independently selected from hydrogen, fluorine, chlorine, bromine, $CF_3$, $CH_3$, and deuterium, provided that at least one of $W_1$, $W_2$, $W_3$, or $W_4$ is not hydrogen;

$X_1$ and $X_5$ are each independently selected from hydrogen, halogen and $C_1$-$C_3$ alkyl;

$X_2$, $X_3$, and $X_4$ are each independently selected from hydrogen, halogen, $OR^5$, $C(O)R^6$, $OS(O)_pR^7$, $NR^3R^4$, $NR^1C(O)R^2$, $NR^1S(O)^pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring is unsubstituted or substituted with one or more $R^a$ and one or two of $X_2$, $X_3$, and $X_4$ is hydrogen;

$R^a$ is selected from halogen, $OR^{25}$, $C_1$-$C_8$ alkyl, $CF_3$, $CHF_2$, $CH_2F$, $NR^{26}C(O)R^{27}$, and $NR^{28}R^{29}$;

or $X_2$ and $X_3$ or $X_4$ and $X_3$ taken together with the atoms to which they are attached form ring selected from a $C_3$-$C_8$ cycloalkyl, $C_4$-$C_8$ cycloalkenyl, aromatic ring, 3-8 membered heteroaromatic ring and 3-8 membered saturated or partially saturated heterocyclic ring, wherein said ring is unsubstituted or substituted with one or more $R^v$;

$R^v$ is selected from halogen, $OR^{25}$, $C_1$-$C_8$ alkyl, $CF_3$, $CHF_2$, $CH_2F$, $NR^{26}C(O)R^{27}$, $NR^{28}R^{29}$, $S(O)_qR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, and $NR^{19}C(O)NR^{20}R^{21}$;

$R^1$ and $R^{26}$ are each independently selected from hydrogen and $C_1$-$C_8$ alkyl;

$R^2$ is selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^b$;

$R^{27}$ is selected from hydrogen, $C_1$-$C_8$ alkyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^b$;

$R^b$ is selected from halogen, $C_1$-$C_8$ alkyl, $CF_3$, $CHF_2$, $CH_2F$, —$OR^{25}$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{b1}$;

$R^{b1}$ is selected from halogen, $C_1$-$C_3$ alkyl, $CF_3$, $CHF_2$, $CH_2F$, $OH$, $OCH_3$, $SOCH_3$, $S(O)_2CH_3$, $NH_2$, $NHCH_3$, and $N(CH_3)_2$;

$R^3$ and $R^4$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^g$;

$R^{28}$ and $R^{29}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^g$;

$R^g$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^h$;

$R^h$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^5$ and $R^{25}$ are each independently selected from hydrogen, $C_1$-$C_8$ alkyl, $CF_3$, $CHF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^c$;

$R^c$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^d$;

$R^d$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^6$ is selected from hydrogen, $OR^{25}$, $C_1$-$C_8$ alkyl, $CF_3$, $CHF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, alkenyl, alkynyl, cycloalkyl, cycloalkenyl, aromatic ring, heteroaromatic ring and heterocyclic ring are unsubstituted or substituted with one or more $R^e$;

$R^e$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^f$;

$R^f$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^7$ is selected from $C_1$-$C_8$ alkyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, cycloalkyl, cycloalkenyl, aromatic ring, heteroaromatic ring, and heterocyclic ring are unsubstituted or substituted with one or more $R^i$;

$R^i$ is selected from halogen, $C_1$-$C_3$ alkyl, $CF_3$, $CHF_2$, $CH_2F$, OH, $OCH_3$, $NH_2$, $NHCH_3$, and $N(CH_3)_2$;

$R^{10}$ are each independently selected from $C_1$-$C_8$ alkyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, cycloalkyl, cycloalkenyl, aromatic ring, heteroaromatic ring, and heterocyclic ring are unsubstituted or substituted with one or more $R^j$;

$R^j$ is selected from halogen, $C_1$-$C_3$ alkyl, $CF_3$, $CHF_2$, $CH_2F$, OH, $OCH_3$, $NH_2$, $NHCH_3$, and $N(CH_3)_2$;

$R^{11}$ is selected from hydrogen, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, alkenyl, alkynyl, cycloalkyl, cycloalkenyl, aromatic ring, heteroaromatic ring and heterocyclic ring are unsubstituted or substituted with one or more $R^k$;

$R^k$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{k1}$;

$R^{k1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{12}$ and $R^{13}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^l$;

$R^l$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^m$;

$R^m$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^{14}$ is selected from $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, and aromatic ring; wherein said alkyl, alkenyl, alkynyl, cycloalkyl, cycloalkenyl, and aromatic ring are unsubstituted or substituted with one or more $R^n$;

$R^n$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{n1}$;

$R^{n1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{15}$ and $R^{16}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^o$;

$R^o$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^p$;

$R^p$ is selected from halogen, $C_1$-$C_3$ alkyl, $CF_3$, $CHF_2$, $CH_2F$, OH, $OCH_3$, $SOCH_3$, $S(O)_2CH_3$, $NH_2$, $NHCH_3$, and $N(CH_3)_2$;

$R^{17}$ and $R^{19}$ are each independently selected from hydrogen and $C_1$-$C_8$ alkyl;

$R^{18}$ is selected from $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated heterocyclic ring; wherein said alkyl, alkenyl, alkynyl, cycloalkyl, cycloalkenyl, heteroaromatic ring, heterocyclic ring, and aromatic ring are unsubstituted or substituted with one or more $R^q$;

$R^q$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^{q1}$;

$R^{q1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{20}$ and $R^{21}$ are each independently selected from selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^r$;

$R^r$ is selected from halogen, $C_1$-$C_3$ alkyl, $CF_3$, $CHCF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^s$;

$R^s$ is selected from halogen, $C_1$-$C_3$ alkyl, $CF_3$, $CHF_2$, $CH_2F$, OH, $OCH_3$, $SOCH_3$, $SO_2CH_3$, $NH_2$, $NHCH_3$, and $N(CH_3)_2$; and p and q are each independently selected from 0, 1, and 2.

In one aspect, the invention provides a compound of formula I or a pharmaceutically acceptable salt, hydrate, solvate, or prodrug thereof, wherein $W_1$, $W_2$, $W_3$, and $W_4$ are each independently selected from hydrogen, chlorine, fluorine, and deuterium, provided that at least one of $W_1$, $W_2$, $W_3$, and $W_4$ is not hydrogen;

$X_1$ and $X_5$ are each independently selected from hydrogen, halogen and $C_1$-$C_3$ alkyl;

$X_2$, $X_3$, and $X_4$ are each independently selected from hydrogen, halogen, $OR^5$, $C(O)R^6$, $OS(O)_pR^7$, $NR^3R^4$, $NR^1C(O)R^2$, $NR^1S(O)_pR^7$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring is unsubstituted or substituted with one or more $R^a$ and one or two of $X_2$, $X_3$, and $X_4$ is hydrogen;

$R^a$ is selected from halogen, $OR^{25}$, $C_1$-$C_8$ alkyl, $CF_3$, $CHF_2$, $CH_2F$, $NR^{26}C(O)R^{27}$ and $NR^{28}R^{29}$; or $R^1$ and $R^{26}$ are each independently selected from hydrogen and $C_1$-$C_8$ alkyl;

$R^2$ is selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^b$;

$R^{27}$ is selected from hydrogen, $C_1$-$C_8$ alkyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^b$;

$R^b$ is selected from halogen, $OR^{25}$ and $C_1$-$C_8$ alkyl;

$R^{28}$ and $R^{29}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, aromatic ring, 3-8 membered heteroaromatic ring, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^g$;

$R^{28}$ and $R^{29}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, and 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^g$;

$R^g$ is selected from halogen, $C_1$-$C_3$ alkyl, $CF_3$, $CHCF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^h$;

$R^h$ is selected from halogen, $C_1$-$C_3$ alkyl, $CF_3$, $CHCF_2$, $CH_2F$, OH, $OCH_3$, $SOCH_3$, $S(O)_2CH_3$, $NH_2$, $NHCH_3$, and $N(CH_3)_2$;

$R^5$ and $R^{25}$ are each independently selected from hydrogen, $C(O)R^6$, $C_1$-$C_8$ alkyl, $CF_3$, $CHCF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said alkyl, alkenyl, alkynyl, cycloalkyl, cycloalkenyl, aromatic ring, heteroaromatic ring and heterocyclic ring are unsubstituted or substituted with one or more $R^c$;

$R^c$ is selected from halogen, $C_1$-$C_3$ alkyl, $CF_3$, $CHCF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^d$;

$R^d$ is selected from halogen, $C_1$-$C_3$ alkyl, $CF_3$, $CHCF_2$, $CH_2F$, OH, $OCH_3$, $SOCH_3$, $S(O)_2CH_3$, $NH_2$, $NHCH_3$, and $N(CH_3)_2$;

$R^6$ is selected from hydrogen, $OR^{25}$, $C_1$-$C_8$ alkyl, $CF_3$, $CHCF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring; wherein said alkyl, alkenyl, alkynyl, cycloalkyl, cycloalkenyl, aromatic ring, heteroaromatic ring and heterocyclic ring are unsubstituted or substituted with one or more $R^e$;

$R^e$ is selected from halogen, $C_1$-$C_3$ alkyl, $CF_3$, $CHCF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, 3-8 membered saturated or partially saturated heterocyclic ring, wherein said cycloalkyl, cycloalkenyl, aromatic ring, heteroaromatic ring, and heterocyclic ring is unsubstituted or substituted with one or more $R^f$;

$R^f$ is selected from halogen, $C_1$-$C_3$ alkyl, $CF_3$, $CHCF_2$, $CH_2F$, OH, $OCH_3$, $SOCH_3$, $S(O)_2CH_3$, $NH_2$, $NHCH_3$, and $N(CH_3)_2$;

$R^7$ is selected from $C_1$-$C_8$ alkyl, aromatic ring, 3-8 membered heteroaromatic ring, and 3-8 membered saturated or partially saturated heterocyclic ring; wherein said alkyl, cycloalkyl, cycloalkenyl, aromatic ring, heteroaromatic ring, and heterocyclic ring are unsubstituted or substituted with one or more $R^i$;

$R^i$ is selected from halogen, $C_1$-$C_3$ alkyl, $CF_3$, $CHCF_2$, $CH_2F$, OH, $OCH_3$, $NH_2$, $NHCH_3$, and $N(CH_3)_2$;

p is selected from 0, 1, and 2.

In one aspect, the invention provides a compound formula I or a pharmaceutically acceptable salt, hydrate, solvate, or prodrug thereof, wherein $R^a$ is selected from halogen, $OR^{25}$, $C_1$-$C_8$ alkyl, $CF_3$, $CHF_2$, $CH_2F$, and $NR^{28}R^{29}$.

In one aspect, the invention provides a compound of formula I or a pharmaceutically acceptable salt, hydrate, solvate, or prodrug thereof, wherein the compound is not N-(2-amino-4-fluorophenyl)-4-[N-(Pyridin-3-ylacryloyl)aminomethyl]benzamide or N-(2-amino-4-fluorophenyl)-4-[N-cinnamoylaminomethyl]benzamide.

In one aspect, the invention provides a compound of formula I or a pharmaceutically acceptable salt, hydrate, solvate, or prodrug thereof, wherein $W_1$, $W_2$, $W_3$ and $W_4$ are each independently selected from hydrogen, fluorine, and deuterium.

In one aspect, the invention provides a compound of formula IA:

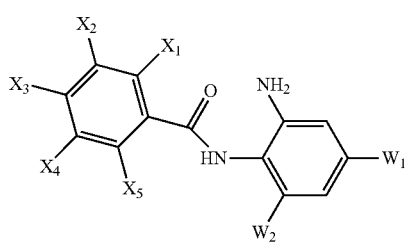

(IA)

or a pharmaceutically acceptable salt, hydrate, solvate, or prodrug thereof, wherein $W_1$, $W_2$, $X_1$, $X_2$, $X_3$, $X_4$, and $X_5$, are as defined formula I.

In one aspect, the invention provides a compound of formula IB:

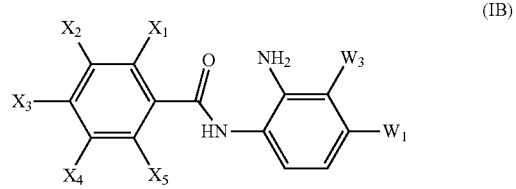

(IB)

or a pharmaceutically acceptable salt, hydrate, solvate, or prodrug thereof, wherein $W_1$, $W_3$, $X_1$, $X_2$, $X_3$, $X_4$, and $X_5$, are as defined for formula I.

In one aspect, the invention provides a compound of formula IC:

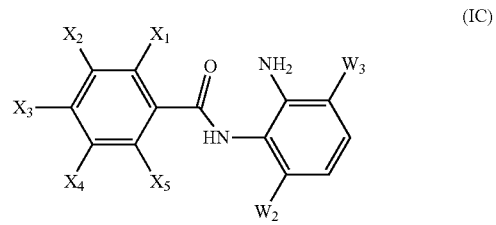

(IC)

or a pharmaceutically acceptable salt, hydrate, solvate, or prodrug thereof, wherein $W_2$, $W_3$, $X_1$, $X_2$, $X_3$, $X_4$, and $X_5$, are as defined for formula I.

In one aspect, the invention provides a compound of formula II:

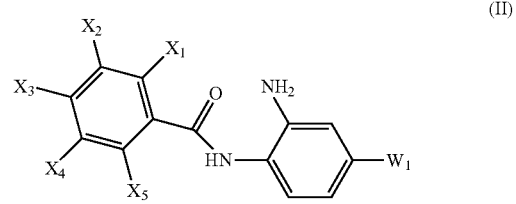

(II)

or a pharmaceutically acceptable salt, hydrate, solvate, or prodrug thereof, wherein $W_1$, $X_1$, $X_2$, $X_3$, $X_4$, and $X_5$, are as defined for formula I.

In one aspect, the invention provides a compound of formula II, wherein $W_1$ is fluorine and the remaining $X_1$, $X_2$, $X_3$, $X_4$, and $X_5$ are as defined for formula I.

In one aspect, the invention provides a compound of formula II, wherein $W_1$ is methyl and the remaining $X_1$, $X_2$, $X_3$, $X_4$, and $X_5$ are as defined for formula I. In one aspect, a compound of formula II, wherein $W_1$ is methyl is not an HDAC3 selective compound. In one aspect, a compound of formula II, wherein $W_1$ is methyl is useful as a negative control for HDAC1,2,3 inhibitory activity.

In one aspect, the invention provides a compound of formula II, wherein $W_1$ is $CF_3$ and the remaining $X_1$, $X_2$, $X_3$, $X_4$, and $X_5$ are as defined for formula I. In one aspect, a compound of formula II, wherein $W_1$ is $CF_3$ is not an HDAC3 selective compound. In one aspect, a compound of formula II, wherein $W_1$ is $CF_3$ is useful as a negative control for HDAC1,2,3 inhibitory activity.

In one aspect, the invention provides a compound of formula IIA:

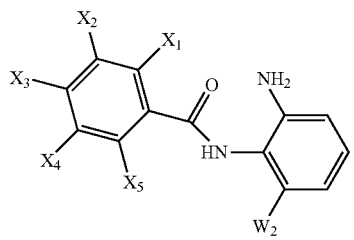

(IIA)

or a pharmaceutically acceptable salt, hydrate, solvate, or prodrug thereof, wherein $W_2$, $X_1$, $X_2$, $X_3$, $X_4$, and $X_5$, are as defined for formula I.

In one aspect, the invention provides a compound of formula IIA, wherein $W_2$ is fluorine and the remaining $X_1$, $X_2$, $X_3$, $X_4$, and $X_5$ are as defined for formula I.

In one aspect, the invention provides a compound of formula IIB:

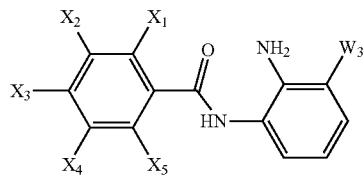

(IIB)

or a pharmaceutically acceptable salt, hydrate, solvate, or prodrug thereof, wherein $W_3$, $X_1$, $X_2$, $X_3$, $X_4$, and $X_5$, are as defined for formula I.

In one aspect, the invention provides a compound of formula IIB, wherein $W_3$ is fluorine and the remaining $X_1$, $X_2$, $X_3$, $X_4$, and $X_5$ are as defined for formula I.

In one aspect, the invention provides a compound of formula I or a pharmaceutically acceptable salt, hydrate, solvate, or prodrug thereof, wherein $W_1$ is deuterium and $W_2$ and $W_3$ are each hydrogen.

In one aspect, the invention provides a compound of formula I or a pharmaceutically acceptable salt, hydrate, solvate, or prodrug thereof, wherein $W_1$ and $W_3$ are each hydrogen and $W_2$ is deuterium.

In one aspect the invention provides a compound of formula I or a pharmaceutically acceptable salt, hydrate, solvate, or prodrug thereof, wherein $W_1$ and $W_2$ are each hydrogen and $W_3$ is deuterium.

In one aspect, the invention provides a compound of formula III:

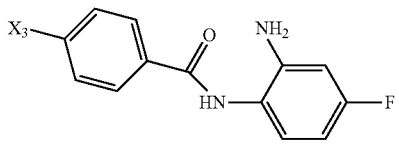

(III)

or a pharmaceutically acceptable salt, hydrate, solvate, or prodrug thereof, wherein $X_3$ is as for formula I. In one aspect, a compound of formula III is HDAC3 selective.

In one aspect, the invention provides a compound of formula IIIC:

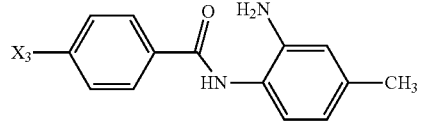

(IIIC)

or a pharmaceutically acceptable salt, hydrate, solvate, or prodrug thereof, wherein $X_3$ is as defined for formula I. In one aspect, a compound of formula IIIC is a negative control.

In one aspect, the invention provides a compound of formula IIIA:

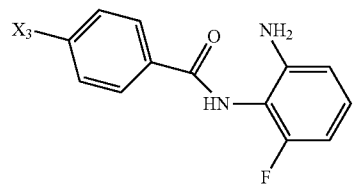

(IIIA)

or a pharmaceutically acceptable salt, hydrate, solvate, or prodrug thereof, wherein $X_3$ is as defined for formula I.

In one aspect, the invention provides a compound of formula IIIB:

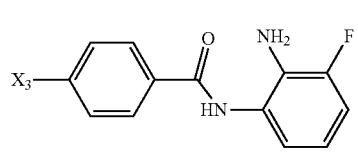

(IIIB)

or a pharmaceutically acceptable salt, hydrate, solvate, or prodrug thereof, wherein $X_3$ is as defined for formula I.

In one aspect, the invention provides a compound of formula IV:

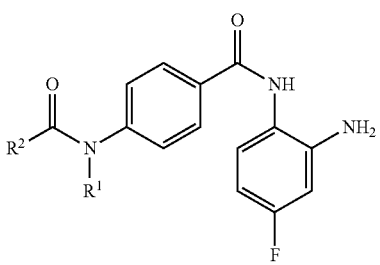

(IV)

or a pharmaceutically acceptable salt, hydrate, solvate, or prodrug thereof, wherein $R_1$ and $R_2$ are as defined for formula I. In one aspect, a compound of formula IV is an HDAC3 selective compound.

In one aspect, the invention provides a compound of formula IVC:

(IVC)

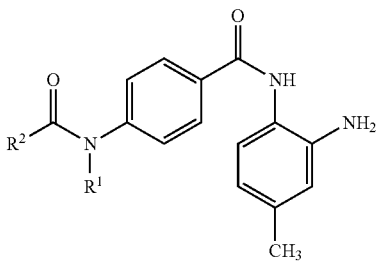

or a pharmaceutically acceptable salt, hydrate, solvate, or prodrug thereof, wherein R₁ and R₂ are as defined for formula I. In one aspect, a compound of formula IVC is a negative control.

In one aspect, the invention provides a compound of formula IVA:

(IVA)

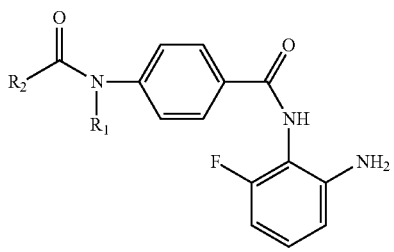

or a pharmaceutically acceptable salt, hydrate, solvate, or prodrug thereof, wherein R₁ and R₂ are as defined for formula I.

In one aspect, the invention provides a compound of formula IVB:

(IVB)

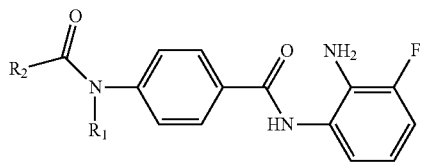

or a pharmaceutically acceptable salt, hydrate, solvate, or prodrug thereof, wherein R₁ and R₂ are as defined for formula I.

In one aspect, the invention provides a compound of formula IV, IVA, IVB, or IVC, wherein $R^1$ is hydrogen and $R^2$ is methyl.

In one aspect, the invention provides a compound of formula V:

(V)

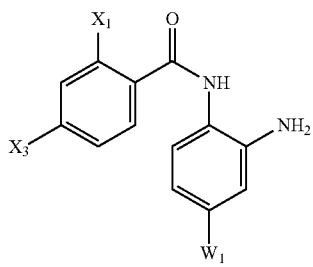

or a pharmaceutically acceptable salt, hydrate, solvate, or prodrug thereof, wherein $X_1$ and $W_1$ are each independently selected from hydrogen and fluorine, and provided that at least one of $X_1$ or $W_1$ is fluorine; $X_3$ is as defined for formula I.

In one aspect, the invention provides a compound of formula VA:

(VA)

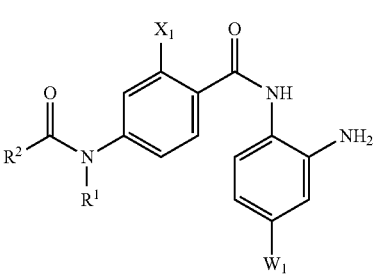

or pharmaceutically acceptable salt, hydrate, solvate, or prodrug thereof, wherein $X_1$ is selected from hydrogen and fluorine, $W_1$ is F, and $X_3$, $R^1$, and $R^2$ are each as defined for formula I.

In one aspect, the invention provides a compound of formulae I, IA, IB, IC, II, IIA, or IIB, wherein two of $X_2$, $X_3$, and $X_4$ are not each independently selected from $OR^5$, $C(O)R^6$, $OS(O)_pR^7$, $NR^3R^4$, $NR^1C(O)R^2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring.

In one aspect, the invention provides a compound of formulae I, IA, IB, IC, II, IIA, or IIB, wherein one of $X_2$, $X_3$, and $X_4$ is selected from $OR^5$, $C(O)R^6$, $OS(O)_pR^7$, $NR^3R^4$, $NR^1C(O)R^2$, $C_3$-$C_8$ cycloalkyl, $C_4$-$C_8$ cycloalkenyl, aromatic ring, 3-8 membered heteroaromatic ring, and 3-8 membered saturated or partially saturated heterocyclic ring and the remaining two of $X_2$, $X_3$, and $X_4$ are each hydrogen.

In one aspect, the invention provides a compound of formulae I, IA, IB, IC, II, IIA, or IIB or a pharmaceutically acceptable salt, hydrate, solvate, or prodrug thereof, wherein $X_1$, $X_2$, $X_4$, and $X_5$ are all hydrogen.

In one aspect, the invention provides a compound of formulae I, IA, IB, IC, II, IIA, or IIB or a pharmaceutically acceptable salt, hydrate, solvate, or prodrug thereof, wherein $X_1$, $X_3$, $X_4$, and $X_5$ are all hydrogen.

In one aspect, the invention provides a compound of formulae I, IA, IB, IC, II, IIA, or IIB or a pharmaceutically acceptable salt, hydrate, solvate, or prodrug thereof, wherein one of $X_1$, $X_2$, $X_4$, and $X_5$ is halogen.

In one aspect, the invention provides a compound of formulae I, IA, IB, IC, II, IIA, or IIB or a pharmaceutically acceptable salt, hydrate, solvate, or prodrug thereof, wherein one of $X_1$, $X_3$, and $X_5$ is halogen.

In one aspect, the invention provides a compound of formulae I, IA, IB, IC, II, IIA, or IIB or a pharmaceutically acceptable salt, hydrate, solvate, or prodrug thereof, wherein one of $X_1$, $X_3$, and $X_5$ is fluorine.

In one aspect, the invention provides a compound of formulae I, IA, IB, IC, II, IIA, IIB, III, IIIA, IIIB, or V or a pharmaceutically acceptable salt, hydrate, solvate, or prodrug thereof, wherein $X_3$ is selected from $NR^1C(O)R^2$, $NR^1S(O)_pR^7$, $OC(O)OR^{14}$, $OC(O)NR^{15}R^{16}$, $NR^{17}C(O)OR^{18}$, and $NR^{19}C(O)NR^{20}R^{21}$.

In one aspect, the invention provides a compound of formulae I, IA, IB, IC, II, IIA, IIB, III, IIIA, IIIB, or V or a pharmaceutically acceptable salt, hydrate, solvate, or prodrug thereof, wherein $X_3$ is $NR^1C(O)R^2$.

In one aspect, the invention provides a compound of formulae I, IA, IB, IC, II, IIA, or IIB or a pharmaceutically acceptable salt, hydrate, solvate, or prodrug thereof, wherein one of $X_2$ or $X_4$ is selected from $NR^1C(O)R^2$, $OC(O)OR^{14}$, $OC(O)NR^{15}R^{16}$, $NR^{17}C(O)OR^{18}$, and $NR^{19}C(O)NR^{20}R^{21}$. In one aspect, the remaining $X_2$ or $X_4$ is hydrogen.

In one aspect, the invention provides a compound of formulae I, IA, IB, IC, II, IIA, or IIB or a pharmaceutically acceptable salt, hydrate, solvate, or prodrug thereof, wherein one of $X_2$ or $X_4$ is $NR^1C(O)R^2$. In one aspect, the remaining $X_2$ or $X_4$ is hydrogen.

In one aspect, the invention provides a compound of formulae I, IA, IB, IC, II, IIA, IIB, III, IIIA, IIIB, IV, IVA, IVB, or VA or a pharmaceutically acceptable salt, hydrate, solvate, or prodrug thereof, wherein $R^1$ is hydrogen.

In one aspect, the invention provides a compound of formulae I, IA, IB, IC, II, IIA, IIB, III, IIIA, IIIB, IV, IVA, IVB, or VA or a pharmaceutically acceptable salt, hydrate, solvate, or prodrug thereof, wherein $R^1$ is methyl.

In one aspect, the invention provides a compound of formulae I, IA, IB, IC, II, IIA, IIB, III, IIIA, IIIB, IV, IVA, IVB or VA or a pharmaceutically acceptable salt, hydrate, solvate, or prodrug thereof, wherein $R^2$ is selected from $C_1$-$C_8$ alkyl, $CF_3$, $CH_2F$, and $CF_2H$. In one aspect, $R^2$ is $C_1$-$C_8$ alkyl. In one aspect, $R^2$ is $C_1$-$C_3$ alkyl. In one aspect, $R^2$ is methyl.

In one aspect, the invention provides a compound of formulae I, IA, IB, IC, II, IIA, IIB, III, IIIA, IIIB, IV, IVA, IVB, or VA or a pharmaceutically acceptable salt, hydrate, solvate, or prodrug thereof, wherein $R^1$ is hydrogen or methyl and $R^2$ is selected from $C_1$-$C_8$ alkyl, $CF_3$, $CH_2F$, and $CF_2H$. In one aspect, $R^1$ is hydrogen or methyl and $R^2$ is $C_1$-$C_8$ alkyl. In one aspect, $R^1$ is hydrogen or methyl and $R^2$ is $C_1$-$C_3$ alkyl. In one aspect, $R^2$ is methyl.

In one aspect, the invention provides a compound of formulae I, IA, IB, IC, II, IIA, or IIB, wherein $X_3$ is halogen and $X_2$ and $X_4$ are each hydrogen.

In one aspect, the invention provides a compound according to Table 1 or a pharmaceutically acceptable salt, hydrate, solvate, or prodrug thereof.

In addition to those compounds presented in the examples, the following compounds further illustrate the scope of the present invention:

TABLE 1

| Structure | Compound Number |
|---|---|
| $C_{15}H_{14}FN_3O_2$ | 1 |
| $C_{16}H_{17}N_3O_2$ | 2 |
| $C_{16}H_{17}F_3N_3O_2$ | 9 |
| $C_{16}H_{14}F_3N_3O_2$ | 10 |
| $C_{15}H_{14}FN_3O_2$ | 3 |
| $C_{15}H_{14}FN_3O_2$ | 4 |

TABLE 1-continued

| Structure | Compound Number |
|---|---|
| (structure) $C_{15}H_{14}BrN_3O_2$ | 5 |
| (structure) $C_{15}H_{13}F_2N_3O_2$ | 6 |
| (structure) $C_{13}H_{11}FN_2O$ | 7 |
| (structure) $C_{13}H_{10}F_2N_3O$ | 8 |

Procedure A

TABLE 1-continued

| Structure | Compound Number |
|---|---|
| (structure) | 11 |
| (structure) | 12 |

In one aspect, a compound of the invention is not compound 12. In one aspect, a compound of the invention is not compounds 9 and 10. In one aspect, a compound of the invention is not compound 11. It is preferred that the subject to be administered a compound of the invention is human.

In one aspect, the invention provides a pharmaceutical composition comprising an effective amount of a compound of the invention or a pharmaceutically acceptable salt, hydrate, solvate, or prodrug thereof and a pharmaceutical carrier, diluent, or excipient.

In one aspect, the invention provides a kit containing one or more compounds of the invention or a pharmaceutically acceptable salt, hydrate, solvate, or prodrug thereof. In one aspect, the kit further contains a pharmaceutically active ingredient.

The present invention relates to a method of synthesizing a compound of the invention or a pharmaceutically acceptable salt, hydrate, solvate or prodrug thereof. A compound of the invention can be synthesized using a variety of methods known in the art. The schemes and description below depict general routes for the preparation of a compound of the invention. Scheme 1 depicts a generally useful preparation.

Scheme I

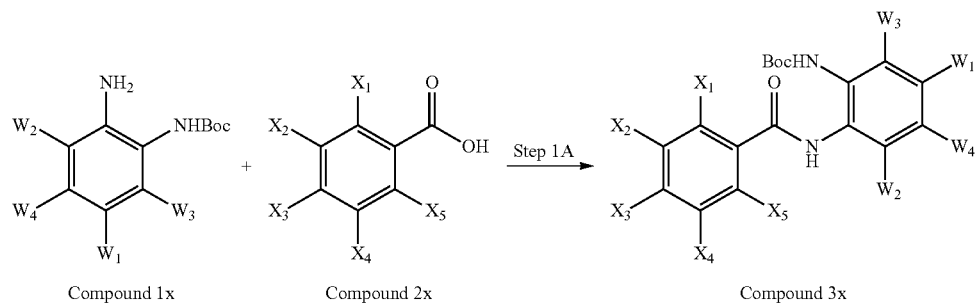

Compound 1x + Compound 2x → Step 1A → Compound 3x

Step 2A

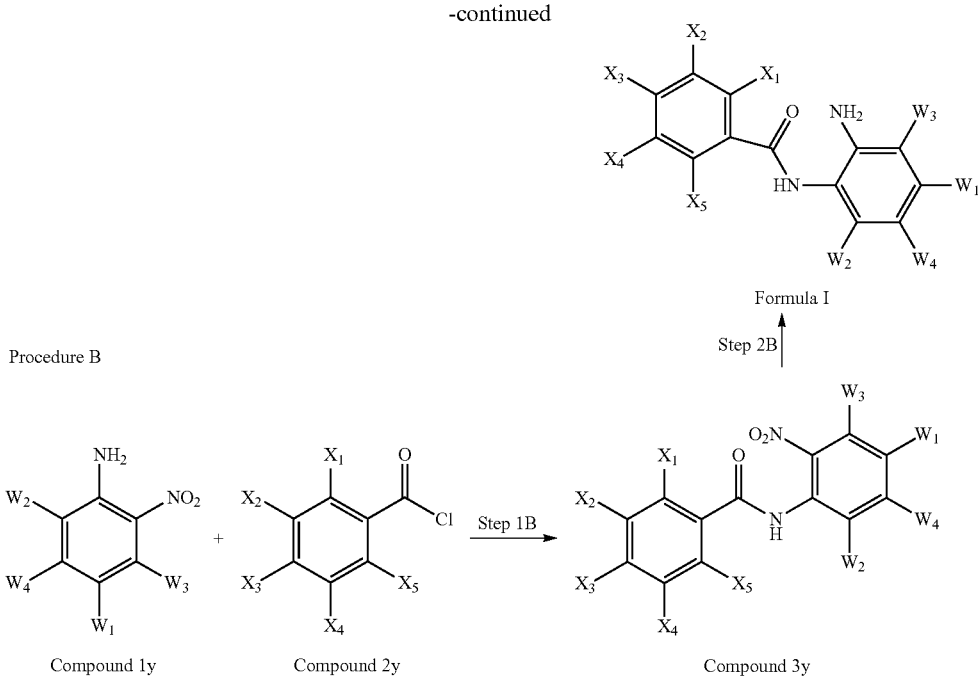

Formula I

Procedure B

Compound 1y        Compound 2y        Compound 3y

Scheme 1 outlines a preparation for a compound of the invention of Formula I. Compounds of Formula I may be prepared using either procedure A or procedure B.

Procedure A:

In procedure A, the preparation outlined in Scheme 1 begins with compound 1x and compound 2x, which are commercially available from chemical vendors. In step 1A, compound 1x and compound 2x are coupled to form compound 3x. For example, compound 1x and compound 2x in an organic solvent (e.g., DMF) are treated with a peptide coupling reagent (e.g., HATU (O-(7-azabenzotriazol-1-yl)-N,N,N',N'-tetramethyluronium hexafluorophosphate) in DMF). The reaction mixture may be quenched by a base (e.g., sodium bicarbonate). Compound 3x may precipitate out of solution and may be filtered off as a solid. The remaining solution containing compound 3x may be extracted with an organic solvent (e.g., ethyl acetate), and the combined organic layer containing compound 3x may be concentrated and then purified by column chromatography (e.g., silica gel, 20-80% EtOAc/hexanes).

In Step 2A, compound 3x in an organic solvent (e.g., dichloromethane) is deprotected to afford a compound of formula I. For example, compound 3x may be treated with an acid (e.g., trifluoroacetic acid). The reaction may be quenched with a base (e.g., saturated aqueous solution of sodium bicarbonate). The compound of formula I may precipitate out of solution and may be filtered off as a solid. The precipitate may be washed with an organic solvent (e.g., cold EtOAc). The aqueous phase containing formula I may be extracted with an organic solvent (e.g., EtOAc). The combined organic layers containing formula I may be concentrated and then purified by column chromatography (e.g., silica gel, 20% EtOAc/hexanes).

Procedure B:

In procedure B, the preparation outlined in Scheme 1 begins with compound 1y and compound 2y, which are commercially available from chemical vendors. In step 1B, compound 1y and compound 2y are coupled to form compound 3y. For example, compound 1y and compound 2y may be treated with a base in an organic solvent (e.g. pyridine in toluene). The resulting reaction mixture may be heated (e.g., reflux overnight). The reaction mixture may then be concentrated, and the residue may be partitioned between an organic solvent and an aqueous base solution (e.g., ethylacetate and a saturated aqueous solution of sodium bicarbonate). Compound 3y may be isolated as resulting solid and washed with a mixture of organic solvents (e.g., ethyl acetate and hexanes (1/1)).

Selected Methods of the Invention

Compounds of the invention are inhibitors of class I histone deacetylases (HDAC). These compounds are useful for protecting β-cells and improving insulin sensitivity, promoting cognitive function and enhancing learning and memory formation. These compounds are also useful in treating, alleviating, and/or preventing various conditions, including e.g., metabolic disorders such as diabetes (type 1 or type 2), dyslipidemias, lipodystrophies, polycystic ovarian syndrome, liver diseases, or obesity, inflammatory diseases, neurological disorders, memory and cognitive function disorders/impairments, extinction learning disorders, fungal diseases and infections, viral diseases and infections such as HIV infection, hematological diseases, lysosomal storage diseases, and neoplastic diseases in humans and animals. In one aspect, compounds of the invention are selective inhibitors of HDAC3 useful for treating diabetes (type 1 or type 2). In one aspect, the compounds of the invention are selective inhibitors of HDAC3 useful for promoting long-term memory formation.

Inhibition of Histone Deacetylase

The compounds of the present invention are useful in a variety of applications for human and animal health. In one aspect, a compound of the invention is a histone deacetylase (HDAC) inhibitor. In one aspect, a compound of the invention is not a histone deacetylase inhibitor. A histone deacetylase inhibitor as used herein is a compound that inhibits, reduces, or otherwise modulates the activity of histone deacetylase. HDACs catalyze the removal of acetyl groups from lysine residues on proteins, including histones. HDAC inhibitors also show diverse biological functions including effecting gene expression, cell differentiation, cell cycle progression, growth arrest, and/or apoptosis. (J. Med. Chem. 2003, 46:5097 and Curr. Med. Chem. 2003, 10:2343). In various embodiments, the compounds of the invention reduce HDAC activity by at least about 50%, at least about 75%, or at least about 90% or more. In further embodiments, HDAC activity is reduced by at least about 95% or at least about 99% or more.

One aspect of the invention provides a method of inhibiting histone deacetylase in a cell, comprising contacting a cell in which inhibition of histone deacetylase is desired with an inhibition effective amount of a compound of the invention or a composition thereof. Because compounds of the invention inhibit histone deacetylase(s), they are useful research tools for in vitro study of the role of histone deacetylase in biological processes. Accordingly, in one aspect of the invention, the step of contacting the cell is performed in vitro.

The term an "inhibiting effective amount" is meant to denote a dosage sufficient to cause inhibition of activity of one or more histone deacetylase in a cell, which cell can be in a multicellular organism. The multicellular organism can be a plant, a fungus, or an animal, preferably a mammal, more preferably a human. The fungus may be infecting a plant or a mammal, preferably a human, and could therefore be located in and/or on the plant or mammal. If the histone deacetylase is in a multicellular organism, the method according to this aspect of the invention comprises administering to the organism a compound or composition of the invention. Measurement of the effect of a compound of the invention on the enzymatic activity of a histone deacetylase is achieved using known methodologies (or example, Bradner, J. et al. Nature Chemical Biology, Vol. 6, March 2010, 238-243 and WO 2013/67391).

The potential of HDAC inhibitors is tremendous, but the development of clinical compounds will likely require the design of isoform selective compounds to minimize side effect issues e.g., fatigue, anorexia, hematological and GI-toxicity. Isoform specific HDAC inhibitors provide advantages by reducing toxicities associated with inhibition of other HDACs and/or the effects of inhibiting multiple HDAC isoforms simultaneously. Selective HDAC inhibitors provide a higher therapeutic index, resulting in better tolerance by patients during chronic or long term treatment. While several HDAC inhibitors are now in the clinic, most of these do not show significant selectivity for individual HDAC isoforms.

HDACs are classified into four classes depending on sequence identity, domain, organization, and function. Compounds of the invention are predominately inhibitors of class I histone deacetylases. Class I enzymes (HDACs 1, 2, 3, and 8) range in size from 42-55 kDa, and are homologs of yeast Rpd3. They are ubiquitously expressed, predominantly nuclear and mainly function as transcriptional corepressors.

In some other embodiments, the compound reduces the activity of fewer than all histone deacetylases in the cell. In certain embodiments, the compound reduces the activity of one histone deacetylase (e.g., HDAC3) or a sub-group of histone deacetylases (e.g., HDAC1, HDAC2, and HDAC3) to a greater extent than other histone deacetylases. Where the compound preferentially reduces the activity of a sub-group of histone deacetylases, the reduction in activity of each member of the sub-group may be the same or different.

In certain embodiments, the present invention relates to the aforementioned compound, wherein the compounds of the invention are selective HDAC class 1 inhibitors. In one aspect, a compound is a HDAC3 inhibitor. In one aspect, a compound is a selective HDAC3 inhibitor. In another aspect, a compound is a non-selective HDAC3 inhibitor. In one aspect, a compound is a HDAC2 inhibitor. In other embodiments, the compound is a non-selective inhibitor of HDAC2. In another aspect, the compound is a HDAC1 inhibitor. In other embodiments, the compound is a non-selective inhibitor of HDAC1. In another embodiment, the compound is a HDAC1,2,3 selective inhibitor.

In one embodiment, a compound selective for HDAC3 will have at least about 2-fold (e.g., at least about 5-fold, 10-fold, 15-fold, or 20-fold) greater activity to inhibit HDAC3 as compared to one or more other HDACs (e.g., one or more HDACs of class I or II, one or more of HDAC1 and HDAC2).

In one aspect, a compound of the invention possesses thermodynamic and kinetic binding selectivity for HDAC3 over HDAC1 and HDAC2. Long residence times are advantageous in terms of duration of pharmacological effect and target selectivity. Long residence times can also mitigate off-target toxicity (Copeland, R. A. et al., Nature, 5, 730-739 (2006); Copeland, R. A. et al., Future Med. Chem. 3(12), 1491-1501 (2011)).

In one embodiment, a compound selectively inhibits at least one class I HDAC enzyme with an $IC_{50}$ value greater than 0.0000001 µM and less than or equal to 0.1 µM, 1 µM, 5 µM, or 30 µM. In another embodiment, a compound selectively inhibits HDAC3 with an $IC_{50}$ value greater than 0.0000001 µM and less than or equal to 0.1 µM, 1 µM, 5 µM, or 30 µM. In one embodiment, a compound selectively inhibits at least two class I HDAC enzymes with $IC_{50}$ values greater than 0.0000001 µM and less than or equal to 0.1 µM, 1 µM, 5 µM, or 30 µM. In one embodiment, a compound selectively inhibits at least three class I HDAC enzymes with $IC_{50}$ values greater than 0.0000001 µM and less than or equal to 0.1 µM, 1 µM, 5 µM, or 30 µM.

In one aspect, the invention provides a method of treating, alleviating, and/or preventing an HDAC3 mediated disease in a subject comprising administering to the subject in need thereof an effective amount of a compound of the invention or a pharmaceutically acceptable salt, hydrate, solvate, or prodrug thereof.

In one aspect, compound 9 and compound 10 do not have a therapeutic utility but rather each is a compound for use as a negative control in in vitro assays to develop therapeutic HDAC inhibitors.

Dopaminergic Disorders

In one aspect, the invention provides a method of treating, alleviating, and/or preventing a dopaminergic disorder in a subject comprising administering to the subject in need thereof an effective amount of a compound of the invention or a pharmaceutically acceptable salt, hydrate, solvate, or prodrug thereof.

In one aspect, a compound of the invention influences dopaminergic signaling. Prior to the present invention, the only compound reported to increase motor responses to amphetamine was a combination treatment of D-amphetamine with the anxiolytic chlordiazepoxide, although these data have been largely dismissed in recent years (Douma et al., Behavioural Brain Research, 225, 377-381, 2011; Kelly et al., Pharmacology, Biochemistry and Behavior, 92, 649-654, 2009). Thus, it is quite a unique/novel finding of the present invention to identify a compound to potentiate amphetamine-induced activity in mice.

Figure 5:
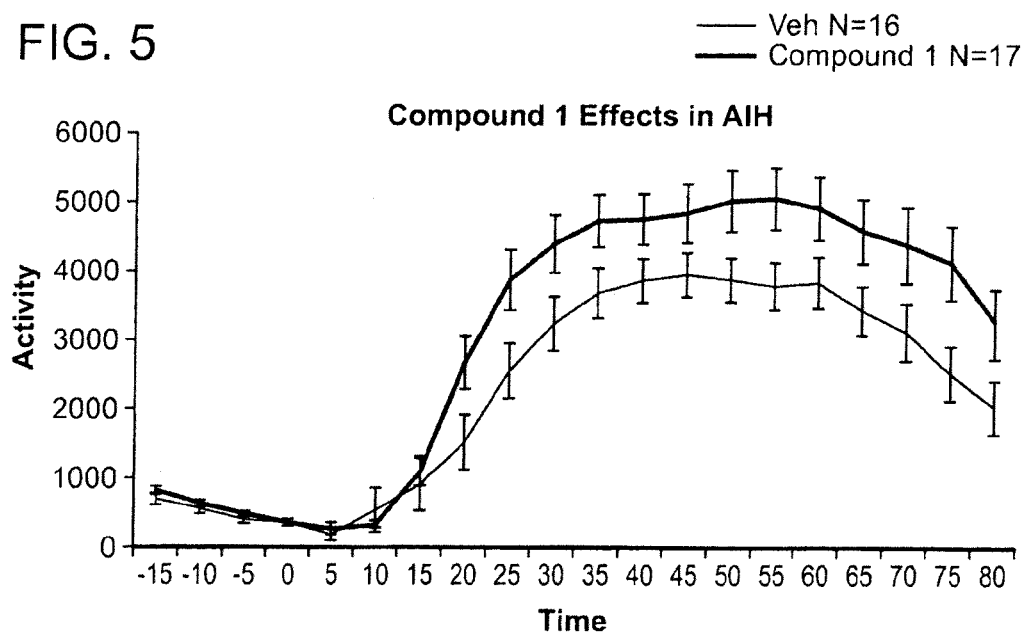
FIG. 5 is a graph which shows the effect of compound 1 in comparison to vehicle to potentiate amphetamine-induced hyperactivity over time (Example 7).
Figure 6:
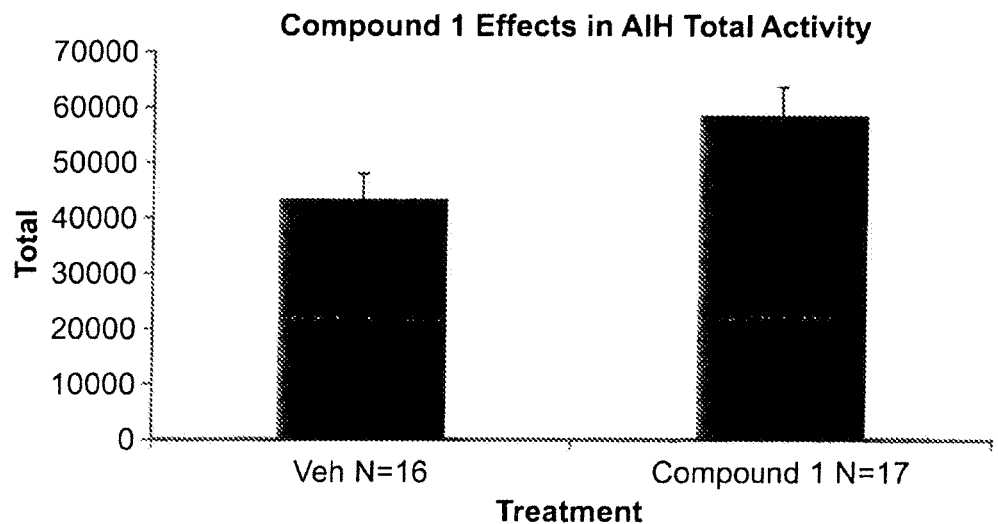
FIG. 6 is a bar graph which shows the effect of compound 1 in amphetamine-induced hyperactivity total activity (Example 7).

HDAC inhibitors designed to target HDAC1,2 are known to attenuate amphetamine induce hyperactivity (AIH) (Schroeder, et al. 2013, submitted). The data presented in FIGS. 5 and 6 shows that the selective HDAC3 inhibitor, compound 1, potentiates (makes more active) the amphetamine-induced hyperactivity.

The ability of the HDAC3 inhibitors of the present invention to potentiate dopaminergic signaling makes them useful in a host of dopaminergic-based neurodegenerative disorders, including Parkinson's and Huntington's disease. A recent publication has demonstrated that inhibition of HDAC3 modulates dopaminergic transmission and medium spiny neqron activity in in-vitro models of Huntington's disease, providing results that inhibition of HDAC3 can relieve HD-like phenotypes in model systems (Jia et al., Neurobiology of Disease, 46, 351-361, 2012).

In one aspect, the invention provides a method of treating, alleviating, and/or preventing a neurodegenerative disorder in a subject comprising administering to the subject in need thereof an effective amount of a compound of the invention or a pharmaceutically acceptable salt, hydrate, solvate, or prodrug thereof. In one aspect, the neurodegenerative disorder is a dopaminergic-based neurodegenerative disorder. In one aspect, the neurodegenerative disorder is selected from Parkinson's disease and Huntington's disease.

Neurological Disorders

In one aspect, the invention provides methods and compositions for treating, alleviating, and/or preventing neurological disorders in a subject comprising administering to the subject in need thereof an effective amount of a compound of the invention.

Recent reports have detailed the importance of histone acetylation in central nervous system ("CNS") functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525).

In one aspect, the invention provides methods and compositions for treating, alleviating, and/or preventing neurological disorders. The term "neurological disorder" as used herein includes neurological diseases, neurodegenerative diseases and neuropsychiatric disorders. A neurological disorder is a condition having as a component a central or peripheral nervous system malfunction. Neurological disorders may cause a disturbance in the structure or function of the nervous system resulting from developmental abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems).

As used herein, the term "neurodegenerative disease" implies any disorder that might be reversed, deterred, managed, treated, improved, or eliminated with agents that stimulate the generation of new neurons. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage diseases such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurodegenerative diseases affecting sensory neurons include Friedreich's ataxia, diabetes, peripheral neuropathy, and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

In some instances the neurological disorder is a neuropsychiatric disorder, which refers to conditions or disorders that relate to the functioning of the brain and the cognitive processes or behavior. Neuropsychiatric disorders may be further classified based on the type of neurological disturbance affecting the mental faculties. The term "neuropsychiatric disorder," considered here as a subset of "neurological disorders," refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV).

One group of neuropsychiatric disorders includes disorders of thinking and cognition, such as schizophrenia and delirium. A second group of neuropsychiatric disorders includes disorders of mood, such as affective disorders and anxiety. A third group of neuropsychiatric disorders includes disorders of social behavior, such as character defects and personality disorders. A fourth group of neuropsychiatric disorders includes disorders of learning, memory, and intelligence, such as mental retardation and dementia. Accordingly, neuropsychiatric disorders encompass schizophrenia, delirium, attention deficit disorder (ADD), schizoaffective disorder, Alzheimer's disease, Rubinstein-Taybi syndrome, depression, mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

In one embodiment, the neurological disorder is Alzheimer's disease, Huntington's disease, seizure-induced memory loss, schizophrenia, Rubinstein Taybi syndrome, Rett Syndrome, Fragile X, Lewy body dementia, vascular dementia, ADHD, ADD, dyslexia, bipolar disorder and social, cognitive and learning disorders associated with autism, traumatic head injury, or attention deficit disorder.

In another embodiment, the neurological disorder is an anxiety disorder, conditioned fear response, panic disorder, obsessive compulsive disorder, post-traumatic stress disorder, phobia, social anxiety disorder, or substance dependence recovery.

In some embodiments neurological disorders are treated or prevented by decreasing the amount of DNA damage within the neuronal cell. In some embodiments neurological disorders are treated or prevented by increasing histone deacetylase activity within the neuronal cell. In some embodiments neurological disorders are treated or prevented by decreasing histone acetyl transferase activity within the neuronal cell. In some embodiments neurological disorders are treated or prevented by increasing the activity of class I histone deacetylases.

Enhancing Cognitive Function

In one aspect, the invention provides methods and compositions for promoting cognitive function and enhancing learning and memory formation in both normal subjects as well as those suffering from memory loss and cognitive function disorders/impairments. As described in the sections below, HDAC3 is the most highly expressed class of HDAC throughout the brain and has been demonstrated to be a critical negative regulator of long-term memory formation. While further testing is expected, it is noted no effect was observed in a wild type normal mouse experiment with compound 1 at a single dose in a fear conditioning assay in normal animals in accordance with protocol of Guan et al., Nature, 55-63, (2004). A normal subject, as used herein, is a subject that has not been diagnosed with a disorder associated with impaired cognitive function. "Cognitive function" refers to mental processes of a subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like.

Memory Disorders/Impairment

Transcription is thought to be a key step for long-term memory processes (Alberini, 2009, Physiol. Rev. 89, 121-145). Transcription is promoted by specific chromatin modifications, such as histone acetylation, which modulate histone-DNA interactions (Kouzarides, 2007, Cell, 128:693-705). Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467).

In contrast, HDACs have been shown to be powerful negative regulators of long-term memory processes. Non-specific HDAC inhibitors enhance synaptic plasticity as well as long-term memory (Levenson et al., 2004, J. Biol. Chem. 279:40545-40559; Lattal et al., 2007, Behav Neurosci 121:1125-1131; Vecsey et al., 2007, J. Neurosci 27:6128; Bredy, 2008, Learn Mem 15:460-467; Guan et al., 2009, Nature 459:55-60; Malvaez et al., 2010, Biol. Psychiatry 67:36-43; Roozendaal et al., 2010, J. Neurosci. 30:5037-5046). For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition have considerable therapeutic potential for many memory and cognitive disorders.

Currently, the role of individual HDACs in long-term memory has been explored in two recent studies. Kilgore et al. 2010, Neuropsychopharmacology 35:870-880 revealed that nonspecific HDAC inhibitors, such as sodium butyrate, inhibit class I HDACs (HDAC1, HDAC2, HDAC3, HDAC8) with little effect on the class IIa HDAC family members (HDAC4, HDAC5, HDAC7, HDAC9). This suggests that inhibition of class I HDACs may be critical for the enhancement of cognition observed in many studies. HDAC3 is the most highly expressed class I HDAC throughout the brain, including the hippocampus (Broide et al., 2007, J. Mol. Neurosci. 31:47-58). HDAC3 alters gene expression as part of a large complex that contains corepressors, nuclear receptor corepressor 1 (NCoR) and silencing mediator for retinoid and thyroid-hormone receptors (SMRT), as well as class IIa HDACs, such as HDAC4 (Guenther et al. 2000, Genes Dev. 14:1048-1057; Li et al., 2000, EMBO J. 19:4342-4350) (for review, see Karagianni, 2007, Oncogene 26:5439-5449). NCoR associates with HDAC3 through the deacetylase activation domain (DAD) of NCoR and a single amino acid substitution (Y478A) in the NCoR DAD results in a mutant protein that is unable to associate with or activate HDAC3 (Alenghat et al., 2008, Nature 456:997-1000). In addition, class IIa HDACs may require interaction with HDAC3 for their HDAC activity (Fischle et al., 2002, Mol. Cell 9:45-57). It has been demonstrated that HDAC3 is a critical negative regulator of long-term memory formation. Specifically, focal deletion of HDAC3 as well as selective inhibition of HDAC3 significantly enhanced long-term memory in a persistent manner (McQuown, 2011, 31(2)764-774).

A "memory" as used herein refers to the ability to recover information about past events or knowledge. Memories include short-term memory (also referred to as working or recent memory) and long-term memory. Short-term memories involve recent events, while long-term memories relate to the recall of events of the more distant past. Methods of assessing the ability to recall a memory are known to those of skill in the art and may involve routine cognitive tests. Enhancing or retrieving memories is distinct from learning. However, in some instances in the art learning is referred to as memory. Learning, unlike memory enhancement, refers to the ability to create new memories that had not previously existed. Thus in order to test the ability of a compound to effect the ability of a subject to learn rather than recall old memories, the compound would be administered prior to or at the same time as the memory is created. In order to test the ability of a compound to affect recall of a previously created memory the compound is administered after the memory is created and preferably after the memory is lost.

As used herein "age related memory loss" refers to any of a continuum of conditions characterized by a deterioration of neurological functioning that does not rise to the level of a dementia, as further defined herein and/or as defined by the Diagnostic and Statistical Manual of Mental Disorders: 4th Edition of the American Psychiatric Association (DSM-IV, 1994). Age related memory loss is characterized by objective loss of memory in an older subject compared to his or her younger years, but cognitive test performance that is within normal limits for the subject's age. Age related memory loss subjects score within a normal range on standardized diagnostic tests for dementias, as set forth by the DSM-IV. Moreover, the DSM-IV provides separate diagnostic criteria for a condition termed Age-Related Cognitive Decline. In the context of the present invention, as well as the terms "Age-Associated Memory Impairment" and "Age-Consistent Memory Decline" are understood to be synonymous with the age related memory loss. Age-related memory loss may include decreased brain weight, gyral atrophy, ventricular dilation, and selective loss of neurons within different brain regions. For purposes of some embodiments of the present invention, more progressive forms of memory loss are also included under the definition of age-related memory disorder. Thus persons having greater than age-normal memory loss and cognitive impairment, yet scoring below the diagnostic threshold for frank dementia, may be referred to as having a mild neurocognitive disorder, mild cognitive impairment, late-life forgetfulness, benign senescent forgetfulness, incipient dementia, provisional dementia, and the like. Such subjects may be slightly more susceptible to developing frank dementia in later life (See also US patent application 2006/008517 (Vasogen Ireland limited) which is incorporated by reference). Symptoms associated with age-related memory loss include but are not limited to alterations in biochemical markers associated with the aging brain, such as IL-1 beta, IFN-gamma, p-JNK, p-ERK, reduction in synaptic activity or function, such as synaptic plasticity, evidenced by reduction in long term potentiation, diminution of memory and learning.

As used herein "injury related memory loss" refers to a loss of memory wherein there is damage to the brain, and there may have also been neurological damage. Sources of brain injury include traumatic brain injury such as concussive injuries or penetrating head wounds, brain tumors, alcoholism, Alzheimer's disease, stroke, heart attack and other conditions that deprive the brain of oxygen, meningitis, AIDS, viral encephalitis, and hydrocephalus.

Methods for enhancing memories can include reestablishing access to memories as well as recapturing memories. The term re-establishing access as used herein refers to increasing retrieval of a memory. Although Applicants are not bound by a mechanism of action, it is believed that the compounds of the invention are effective in increasing retrieval of memories by re-establishing a synaptic network. The process of re-establishing a synaptic network may include an increase in the number of active brain synapses and or a reversal of neuronal loss.

The invention provides methods for enhancing memory in a subject having a memory disorder. Examples of types of memory disorders include Alzheimer's disease, absent-minded professor, absent-mindedness, amnesia, anterograde amnesia, blackout (alcohol-related amnesia), bromism, childhood amnesia, false memory syndrome, fugue state, hyperthymesia, Korsakoff's syndrome, lacunar amnesia, memory distrust syndrome, memory loss, post-traumatic amnesia, prosopamnesia, psychogenic amnesia, repressed memory, retrograde amnesia, Ribot's Law, selective memory loss, sywald skeid, source amnesia, source-monitoring error, the seven sins of memory, tip of the tongue, transient epileptic amensia, transient global amnesia, and twilight sleep.

In one embodiment, Alzheimer's disease is the memory disorder. Such methods optionally involve administering the inhibitor and monitoring the subject to identify recapture of a memory that was previously lost. Subjects may be monitored by routine tests known in the art.

In other embodiments the Alzheimer's subject is one that has late stage Alzheimer's disease. Many of the drugs suggested for treating Alzheimer's disease are designed to treat the early stages of the disease by preventing plaque buildup. The compounds of the invention are useful for treating both early stages and late stages of dementia because they actually improve memory and cognition rather than preventing only plaque accumulation.

Cognitive Function Disorders/Impairment

The invention relates to methods of treating, alleviating, and/or preventing cognitive function disorders/impairments in a subject by administering to the subject in need thereof an effective amount of a compound of the invention.

Impaired cognitive function refers to cognitive function that is not as robust as that observed in an age-matched normal subject and includes states in which cognitive function is reduced. In some cases, cognitive function is reduced by about 5%, about 10%, about 30%, or more, compared to cognitive function measured in an age-matched normal subject. Cognitive function may be promoted to any detectable degree, but in humans preferably is promoted sufficiently to allow an impaired subject to carry out daily activities of normal life.

In some embodiments, the cognitive function disorders or impairments are associated with, but not limited to, Alzheimer's disease, Huntington's disease, seizure induced memory loss, schizophrenia, Rubinstein Taybi syndrome, Rett Syndrome, Fragile X, Lewey body dementia, Vascular dementia, bipolar disorder and social, cognitive and learning disorders associated with autism, attention deficit hyperactivity disorder (ADHD), dyselexia, learning disorders, traumatic head injury, stroke induced cognitive and motor impairment, traumatic brain injury, neurodegeneration and neuronal loss mediated cognitive impairment, and attention deficit disorder.

In some embodiments, the cognitive function disorders or impairments are associated with, but not limited to, anxiety disorders, conditioned fear response, panic disorders, obsessive compulsive disorders, post-traumatic stress disorder, phobias, social anxiety disorders, substance dependence recovery or Age Associated Memory Impairment (AAMI), and Age Related Cognitive Decline (ARCD).

In some embodiments, the invention relates to methods of treating, alleviating, and/or preventing vascular dementia. Vascular dementia, also referred to as "multi-infarct dementia", refers to a group of syndromes caused by different mechanisms all resulting in vascular lesions in the brain. The main subtypes of vascular dementia are, for example vascular mild cognitive impairment, multi-infarct dementia, vascular dementia due to a strategic single infarct (affecting the thalamus, the anterior cerebral artery, the parietal lobes or the cingulate gyms), vascular dementia due to hemorrhagic lesions, small vessel disease (including, e.g. vascular dementia due to lacunar lesions and Binswanger disease), and mixed Alzheimer's Disease with vascular dementia.

In some embodiments, the invention relates to treating, alleviating, and/or preventing Huntington's Disease. Huntington's Disease is a neurological disease which results in cognitive decline associated with inexorable progression to death. Cognitive symptoms associated with Huntington's Disease include loss of intellectual speed, attention, and short term memory and/or behavioral symptoms.

Cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." Neurotoxicol Teratol 1996; 18(4):499-504), Stroop Test, Trail Making, Wechsler Digit Span, or the CogState computerized cognitive test (see also Dehaene et al. "Reward-dependent learning in neuronal networks for planning and decision making." Brain Res. 2000; 126:21729; Iverson et al. "Interpreting change on the WAIS-III/WMS-III in clinical samples." Arch Clin Neuropsychol. 2001; 16(2):183-91; and Weaver et al. "Mild memory impairment in healthy older adults is distinct from normal aging." Cogn. 2006; 60(2):146-55). The methods of the invention may be used to promote cognitive function in a normal subject or to treat, alleviate and/or prevent a subject from having a cognitive dysfunction. A normal subject, as used herein, is a subject that has not been diagnosed with a disorder associated with impaired cognitive function.

Compounds of the invention can be evaluated for their ability to treat, alleviate, or prevent a cognitive disorder using methods know in the art see e.g., Learning tests: all behavioral testing is described in Fischer et al., Neuron 48, 825-838 (2005); Learn Mem. 2005 March-April; 12(2): 111-9. Transgenic mice expressing a truncated form of CREB-binding protein (CBP) exhibit deficits in hippocampal synaptic plasticity and memory storage. Wood M A, Kaplan M P, Park A, Blanchard E J, Oliveira A M, Lombardi T L, Abel T; References: Cruz J C, et al. Neuron 2003, 40:471-483; Fischer A, et al, Neuron, 2005, 48: 825-838; Fischer A, et al., Nature 2007, 447: 178-182.

Extinction Learning Disorders

In one aspect, the invention relates to methods of treating, alleviating, and/or preventing extinction learning disorders e.g., a fear extinction deficit in a subject comprising administering to the subject in need thereof an effective amount of a compound of the invention.

It has been demonstrated that administration of the HDAC inhibitors sodium butyrate or trichostatin A facilitates fear extinction in mice and this enhancement mirrors that caused by commonly used behavioral manipulation and is consistent with other studies demonstrating a role for the hippocampus in the extinction of contextual fear (Lattal, et al., 2007, Behav. Neurosci. 121, 5, 1125-1131).

Compounds of the invention can be used to facilitate the psychological process of extinction learning and thus are useful for treating, alleviating, and/or preventing neuropsychiatric disorders and other related disorders. Unlike traditional anti-anxiety drugs that are administered on a chronic basis and address physiological symptoms of anxiety, the compounds of the invention can be used on a chronic or acute basis in conjunction with a second therapy e.g., psychotherapy.

In one aspect, the present invention is directed to methods for treating, alleviating, and/or preventing a subject from having a neuropsychiatric disorder. The methods comprise subjecting the subject to one or more sessions of a combination therapy protocol, where the combination therapy protocol comprises an acute administration of a therapeutically effective amount of a compound of the invention that enhances learning or conditioning in combination with a session of psychotherapy. By "acute administration" is intended a single exposure of the subject to the therapeutically effective amount of the compound that enhances learning or conditioning. In one aspect, the exposure to the compound occurs within about 24 hours prior to initiating the session of psychotherapy, preferably within about 12 hours, and more preferably within about 6 hours prior to initiating the session of psychotherapy. A full course of treatment for the neuropsychiatric disorder entails at least one session of this combination therapy protocol.

For purposes of the present invention, a subject may have a single disorder, or may have a constellation of disorders that are to be treated, alleviated, and/or prevented by the methods described herein.

In some embodiments, the invention provides method of treating, alleviating, and/or preventing a neuropsychiatric disorder in a subject comprising administering to the subject in need thereof an effective amount of a compound of the invention or a pharmaceutically acceptable salt, hydrate, solvate, or prodrug thereof.

The neuropsychiatric disorders contemplated in the present invention include, but are not limited to, fear and anxiety disorders, addictive disorders including substance-abuse disorders, and mood disorders. Within the fear and anxiety disorder category, the invention encompasses the treatment or prevention of panic disorder, specific phobia, post-traumatic stress disorder (PTSD), obsessive-compulsive disorder, and movement disorders such as Tourette's syndrome. The disorders contemplated herein are defined in, for example, the DSM-IV (Diagnostic and Statistical Manual of Mental Disorders (4th ed., American Psychiatric Association, Washington D.C., 1994)), which is herein incorporated by reference.

Anxiety-related disorders relate to those disorders characterized by fear, anxiety, addiction, and the like. Patients with anxiety-related disorders can have a single such disorder, or can have a constellation of disorders. The anxiety-related disorders contemplated in the present invention include, but are not limited to, anxiety disorders, addictive disorders including substance-abuse disorders, mood disorders (e.g., depression and/or bipolar disorder), movement disorders such as Tourette's syndrome, psychogenic erectile dysfunction (impotence resulting from a man's inability to obtain or maintain an erection of his penis), insomnia (e.g. chronic insomnia), and eating disorders (e.g. anorexia).

Anxiety disorders include, but are not limited to, panic disorder, agoraphobia, social phobia, specific phobia, PTSD, obsessive-compulsive disorder, and generalized anxiety disorder. The disorders contemplated herein are defined in, for example, the DSM-IV (Diagnostic and Statistical Manual of Mental Disorders (4th ed., American Psychiatric Association, Washington D.C., 1994)).

Movement disorders are neurological conditions that affect the speed, fluency, quality, and ease of movement. Representative movement disorders include but are not limited to ataxia, chorea, myoclonus, dystonia, Parkinson's disease, restless leg syndrome, tics, and Tourette's syndrome. Movement disorders typically occur as a result of damage or disease in the basal ganglia region of the brain. Movement disorders can result from age-related changes, medications, genetic disorders, metabolic disorders, disease, stroke, or injury. Recovery of movement after stroke or injury may be facilitated when treated according to the methods of the invention.

Addictive disorders are disorders characterized by addiction to an activity or substance, and include, for example, alcohol addiction, drug addiction, and gambling addiction.

Depression refers to the clinical condition known as major depressive disorder, and is characterized by a state of intense sadness, melancholia, or despair that has advanced to the point of being disruptive to an individual's social functioning and/or activities of daily living. Depression is alleviated if either (or both) the severity or frequency of a symptom of the depression is reduced. However, a subject can be treated for depression in accordance with the methods of the invention irrespective of whether the treatment actually was successful in alleviating the depression.

Insomnia is defined herein as the inability to fall asleep or to stay asleep for a sufficient amount of time during regular sleeping hours. It includes acute insomnia, which occurs in either a transient or short term form, and chronic insomnia. It also includes initial insomnia, defined as difficulty in falling asleep; middle insomnia, defined as awakening in the middle of the night followed by eventually falling back to sleep, but with difficulty; and terminal insomnia, defined as awakening before one's usual waking time and being unable to return to sleep.

As defined by the National Institute of Mental Health, Autism Spectrum Disorders (ASD), also widely known as Pervasive Developmental Disorders (PDDs), cause severe and pervasive impairment in thinking, feeling, language, and the ability to relate to others. These disorders are usually first diagnosed in early childhood and range from a severe form, called autistic disorder, through pervasive development disorder not otherwise specified (PDD-NOS), to a much milder form, Asperger syndrome. They also include two rare disorders, Rett syndrome and childhood disintegrative disorder.

Attention-Deficit Hyperactivity Disorder (ADHD) is one of the most common mental disorders that develop in children. Children with ADHD typically have impaired functioning in multiple settings, including home, school, and in relationships with peers. Symptoms of ADHD include impulsiveness, hyperactivity, and inattention.

Typical treatments encompassed by the present invention include combination therapies. For instance, the combination therapy may be a pharmacotherapy (i.e., a compound of the invention) and a behavioral therapy. Behavioral therapy comprises, but is not limited to, electroconvulsive seizure therapy, exercise, group therapy, talk therapy, or conditioning. In another embodiment, the behavioral therapy is cognitive-behavioral therapy. Examples of behavioral therapy that may be used in the ongoing methods are described, for example, in Cognitive-Behavioral Therapies by K. Dobson, ed., Guilford Publications, Inc., 2002; The new Handbook of Cognitive Therapy: Basics and Beyond by Judith S. S. Beck, Guilford Publications, Inc. 1995 herein incorporated by reference in their entireties. Any pharmaceutical active ingredient that is recognized by the skilled artisan as being a pharmacologic agent that enhances learning or conditioning can be used in the methods of the invention. For example, one such class of pharmaceutical active ingredients contemplated herein comprises compounds that increase the level of norepinephrine in the brain. Such compounds include those acting as norepinephrine reuptake inhibitors, for example tomoxetine, reboxetine, duloxetine, venlafaxine, and milnacipran, and those compounds that cause release of norepinephrine, for example amphetamine, dextroamphetamine, pemoline, and methylphenidate. Another class of such pharmaceutical active ingredients is those compounds that increase the level of acetylcholine in the brain, including, for example, compounds that block its breakdown. Examples of such compounds include, but are not limited to, donepezil HCl or Aricept™ and tacrine, which inhibit cholinesterase activity.

Methods of the invention also encompass the use in combination with a compound of the invention of any type of psychotherapy that is suitable for the particular psychiatric disorder for which the subject is undergoing treatment. Suitable methods of psychotherapy include exposure based psychotherapy, cognitive psychotherapy, and psychodynamically oriented psychotherapy. Methods of the invention also encompass exposing the subject to cognitive behavioral therapy (CBT), behavioral exposure treatments, virtual reality exposure (VRE) or cognitive remediation therapy.

Methods of the invention also encompass extinction training. The goal of extinction training is to pair a stimulus that previously provoked a deleterious, unwanted response with a new learning that will not lead to a negative outcome, thereby generating in a subject a new, more appropriate response to the stimulus to compete with and ideally replace the previous undesirable response. Extinction training frequently exposes a subject to a stimulus or situation in the absence of an aversive consequence, e.g., a subject that has deleterious, high anxiety responses to a given stimulus or situation is exposed to that stimulus or situation in the absence of an aversive consequence. A typical goal of extinction training is to produce new learning in the subject that results from the pairing of the original stimulus or situation with a non-deleterious outcome, thereby generating, in subsequent exposures to the stimulus, a more appropriate response in place of the unwanted response. An extinction learning event refers to a completed stimulus/response extinction training cycle.

One form of extinction training entails psychotherapy. For example, the methods of the invention contemplate treating, alleviating, and/or preventing anxiety disorders by: (i) administering psychotherapy to treat, alleviate, and/or prevent an anxiety-related disorder in a suitable human subject, and (ii) administering a therapeutically effective dose a compound of the invention to said subject on an achronic, post-training, pre-sleep basis. Suitable methods of psychotherapy include but are not limited to exposure-based psychotherapy, cognitive psychotherapy, and psychodynamically oriented psychotherapy.

One method of psychotherapy that is specifically contemplated is the use of virtual reality (VR) exposure therapy to treat, alleviate, and/or prevent an anxiety disorder using the methods of the invention.

Another method of psychotherapy that is particularly beneficial when utilized in combination with a compound or composition of the present invention is cognitive behavioral therapy ("CBT"). CBT is a form of psychotherapy that combines cognitive therapy and behavior therapy, and emphasizes the critical role of thinking in causing people to act and feel as they do. Therefore, if an individual is experiencing unwanted feelings and behaviors, CBT teaches that it is important to identify the thinking that is causing the undesirable feelings and/or behaviors and to learn how to replace this deleterious thinking with thoughts that lead to more desirable reactions. CBT is widely used to help people who are experiencing a range of mental health difficulties, some of which do not conveniently fit definitions of a particular medical affliction. CBT has been used to treat anxiety disorders, mood disorders, addictive disorders, eating disorders, insomnia, chronic pain, schizophrenia, fibromyalgia, ADHD, and autism spectrum disorders, among others. Post-extinction training pre-sleep administration of a compound of the invention, subsequent to CBT treatment, can be used to augment the effectiveness of the CBT treatment for these medical conditions.

In one embodiment, subjects suffering from social anxiety disorder undergo weekly cognitive behavioral therapy sessions to treat the affliction. After each therapy session, subjects are administered a therapeutically effective formulation of compounds of the invention on a post-extinction training pre-sleep basis. Relative to subjects treated only via cognitive behavioral therapy, or to subjects treated via cognitive behavioral therapy and a placebo, anxiety associated with social anxiety disorder is expected to be reduced to a greater extent in subjects treated with a combination of cognitive behavioral therapy and achronic administration of a compound of the invention on a post-extinction training pre-sleep basis.

In another embodiment of the invention, a compound of the invention is administered after extinction training only if the extinction training yields positive results on that day. For example, a subject undergoing cognitive behavioral therapy for PTSD is administered a compound of the invention on a post-extinction training only if the cognitive behavioral therapy was deemed to be successful, as determined by the subject and/or therapist. In one aspect, the compound is administered on a post-extinction, pre-sleep basis. In another aspect, a subject undergoing cognitive behavioral therapy for PTSD is administered a compound of the invention on a pre-extinction training. In one aspect, the compound is administered on a pre-extinction, pre-sleep basis. This method may also be useful when applied to treatment of autism spectrum disorders or attention-deficit hyperactivity disorder.

In another embodiment of the invention, subjects afflicted with anxiety disorders such as PTSD receive extinction training using Eye Movement Desensitization and Reprocessing (EMDR), and subsequently are administered a therapeutically effective dose of a compound of the invention on a post-extinction training pre-sleep basis.

Another form of extinction training is provided by biofeedback, which is particularly useful in enabling subjects to learn to control physiological processes that normally occur involuntarily, such as blood pressure, heart rate, muscle tension, and skin temperature. As used herein, "biofeedback" refers to a technique in which subjects are trained to improve their health by using signals from their own bodies to control their own physiological responses.

In one embodiment of the invention, a subject suffering from chronic pain undergoes biofeedback sessions to help alleviate the pain. Upon the conclusion of each session wherein the subject has made progress in learning/developing responses that reduce the chronic pain, the subject is administered a compound of the invention on a post-extinction training pre-sleep basis in order to consolidate the desired learning.

In another embodiment, a subject suffering from phantom limb syndrome undergoes thermal biofeedback sessions to reduce and hopefully eliminate the symptoms. After each session, the subject is administered a therapeutically effective formulation of a compound of the invention on a post-extinction training pre-sleep basis.

In another embodiment, extinction training can be provided by physical therapy, or virtual reality physical therapy such as virtual reality gait therapy. For example, a stroke victim re-learning how to walk can undergo virtual reality gait therapy, and then be administered a compound of the invention on an achronic, post-extinction training pre-sleep basis.

Another form of extinction training can be provided by pharmacotherapy. For example, a man afflicted with erectile dysfunction can have an extinction learning event based on a positive sexual outcome, including instances wherein the positive sexual outcome was achieved with the pharmacological assistance of a PDE-5 inhibitor such as sildenafil, tadalafil, vardenafil, and/or udenafil. By administering a compound of the invention on a post-extinction training pre-sleep basis to a subject with erectile dysfunction, following a successful sexual outcome wherein the subject utilized sildenafil, the heightened confidence and reduced sexual performance anxiety resulting from a successful outcome can be consolidated in said subject's psyche, thereby facilitating extinction of any deleterious performance anxiety associated with sexual intercourse.

Extinction training does not always require intervention of a trained specialist. Individuals can carry out extinction training on themselves.

Fungal Diseases or Infections or Viral Diseases or Infections

In some aspects, the invention relates to a method for treating, alleviating, and/or preventing a fungal disease or infection in a subject comprising administering to the subject need thereof an effective amount of a compound of the invention. In some aspects, the invention relates to a method for treating, alleviating, and/or preventing a viral disease or infection in a subject comprising administering to the subject need thereof an effective amount of a compound of the invention. In a further aspect, the method is for a latent viral infection. The invention provides a method for treating, alleviating, and/or preventing a hospital-acquired fungal infections that attack immunocompromised patients including those with HIV and cancer. In one embodiment, the invention provides a method for treating, alleviating, and/or preventing a fungal disease in a subject not suffering from cancer.

Viral Immunodeficiency

In one aspect, the invention relates to a method for treating, alleviating, and/or preventing a viral immunodeficiency infection in a subject comprising administering to the subject need thereof an effective amount of a compound of the invention. In one aspect, the invention relates to a method for treating, alleviating, and/or preventing an HIV infection in a subject comprising administering to the subject need thereof an effective amount of a compound of the invention. In one aspect, the method is for treating a latent viral immunodeficiency infection. In a further aspect, the method is for treating a latent HIV infection. Proviral latency of human immunodeficiency virus type 1 (HIV-1) is a principal obstacle to curing the infection. In one aspect, the invention relates to treatment for reactivating latent HIV. Latent infection of resting CD4+ T cells is established early during HIV-1 infection, making eradication of HIV unachievable with current therapies. One of the mechanisms through which HIV latency is maintained is by the action of histone deacetylases at the HIV-1 long terminal repeat (LTR) promote. Specifically, deacetylation of histone proteins at the HIV-LTR by HDACs promotes transcriptional repression and virus latency. As such, HDAC inhibitors can be used to deplete reservoirs of persistent, quiescent HIV-1 proviral infection (Archin, et al., Nature, 487, 482-460 (2012); Archin et al., AIDS 23, 1799-1806 (2009)). The development of HDAC inhibitors to purge latent HIV-1 requires knowledge of the HDAC isoforms contributing to viral latency and the development of inhibitors specific to these isoforms. It has been found that the inhibition of HDAC3 is necessary to activate latent HIV-1 (Huber, K. et al., J. Bio. Chem. 286, 25, 22211-22218 (2011)).

Inflammatory Disease

In some aspects, the invention relates to a method for treating, alleviating, and/or preventing an inflammatory disease in a subject by administering to the subject in need thereof an effective amount of a compound of the invention. HDACs regulate inflammatory gene expression as indicated by the potent anti-inflammatory activity of pan-HDAC inhibitors. Recently, it was found that HDAC3 deficient macrophages were unable to activate inflammatory gene expression when stimulated with LPS (Chen, X. et al., PNAS, early addition, accepted May 9, 2012, 1-10).

Inflammatory disease includes but is not limited to stroke, rheumatoid arthritis, lupus erythematosus, ulcerative colitis and traumatic brain injuries (Leoni et al., PNAS, 99(5); 2995-3000 (2002); Suuronen et al. J. Neurochem. 87; 407-416 (2003) and Drug Discovery Today, 10: 197-204 (2005)). In one aspect, type 2 diabetes is an inflammatory disease. The participation of inflammation in the pathogenesis of type 2 diabetes has been described (Donath et al., Nat. Rev. Immunol. 11(2); 98-107 (2011)). Type 1 diabetes also contains an inflammatory aspect (Donath et al. Endocrine Reviews (2008) 29(3):334-350).

Metabolic Disorders

In some aspects, the invention relates to methods of treating, alleviating, and/or preventing a metabolic disorder in a subject comprising administering to the subject in need thereof a compound of the invention to a subject. Metabolism is the breaking down of food to its simpler components: proteins, carbohydrates (or sugars), and fats. Metabolic disorders occur when these normal processes become disrupted. Disorders in metabolism can be inherited, in which case they are also known as inborn errors of metabolism, or they may be acquired during your lifetime. Many metabolic disorders exist, and they are common in the United States. For, instance, diabetes is a metabolic disorder that affects approximately 26 million Americans.

HDACs have been implicated in a variety of different metabolic disorders, including diabetes (Glamozzi, A., et al., Diabetes, published on-line Oct. 15, 2012, 1-11; Ishikawa-Kobayashi, E. Chronobiology International, 29(8), 982-993 (2012)). HDAC inhibitors have also been show to prevent degradation and restore the activity of glucocerebrosidase in Gaucher disease (Lu, et al., PNAS, 108, 21200-21205 (2011)) Treatment with HDAC inhibitors has also been shown to dramatically reduce cholesterol accumulation in Niemann-Pick type C1 mutant human fibroblasts (Pipalia, et al., PNAS, early release, 1-6).

Fibroblast growth factor (FGF21) is a metabolic regulator. For example, FGF21 has been shown to improve pancreatic β-cell function and survival by activation of extracellular signal-regulated kinase ½ and Akt signaling pathways (Wolf, W. et al., Diabetes, 55, 2470-2478 (2006)) and to improve glucose and lipid metabolism as well as to reduce overall body weight and adipose mass (Berglund, E. D. et al., Endocrinology, 150(9), 4084-4093 (2009)). FGF21 is also known to stimulate fatty acid oxidation and ketone body production in animals. For example, FGF21 administration increases energy expenditure, decreases blood lipids, and reduces hepatic steatosis in dietary obese mice. It has been shown that sodium butyrate stimulates the expression of FGF21 in liver by inhibition of HDAC3 (Li, et al., Diabetes, 61, 797 (2012). The metabolic state of diabetic monkeys has been shown to be regulated by FGF21 (Kharitonenkov, A. et al., Endocrinology, 148(2), 774-781 (2007). Example 9 shows that compounds of the invention upregulate FGF21 mRNA expression in Hep2G cells. The ability of the compounds of the invention to upregulate FGF21 makes them useful in the treatment of metabolic disorders, including diabetes, obesity and associated comorbities such as hyperglycemia, insulin resistance, increased triglycerides, etc. The ability of a compound of the invention to treat diabetes by upregulating a protein such as FGF21 at the site of action provides advantages over strategies focused on the delivery of FGF21 directly.

By the inhibition of HDAC3 transcription of the endogenous FGF21 protein can be used as opposed to the direct delivery of the protein FGF21 by IV or subcutaneous injections. The problems with the delivery of the FGF21 protein directly relate to poor inherent PK properties of FGF21, high dose requirements and high peripheral exposures, which are needed to overcome the poor PK properties. This approach leads to higher concentrations of FGF21 at sites other than the liver, fat tissue and possibly pancreas where the efficacious effects are driven. High concentrations of FGF21 can effect bone loss (Wei, W. et al., PNAS, 109, 3143 (2012). Attempts have been made to solve the protein delivery problem by making synthetic constructs and new formulations of FGF21 to get better and more sustained exposures. However, the problem of suboptimal PK properties and the resulting high peripheral exposures to achieve sufficient exposure within target tissue are still not solved.

An HDAC3 selective inhibitor, such as a compound of the invention, increases FGF21 in the liver, which is the location of the site of action and then, the protein is secreted into the peripheral. Thus, by increasing the concentration of FGF21 within the specific cell types where the sight of action is located (human liver cells, HEPG2), efficacy can be achieved with only a small fraction of the peripheral exposure and increase the therapeutic window for this approach.

In one aspect, the invention relates to a method of upregulating FGF21 expression in a subject by administering to the subject in need thereof an effective amount of a compound of the invention. The FGF21 expression is increased by 2-fold, 3-fold, 5-fold, 10-fold, 15-fold, 20-fold, 50-fold, or 80-fold. The upregulation of FGF21 expression by a compound of the invention is desirable. In one aspect, a compound of the invention improves glycemic control in the subject. In one aspect, a compound of the invention ameliorates hyperglycemia. In one aspect, a compound of the invention increases glucose disposal. In one aspect, a compound of the invention improves hepatic insulin sensitivity. In one aspect, a compound of the invention suppresses hepatic glucose production. In one aspect, a compound of the invention increases liver glycogen. In one aspect, a compound of the invention lowers glucagon. In one aspect, a compound of the invention improves glucose clearance.

Metabolic disorders can be complications of severe diseases or conditions, including liver or respiratory failure, cancer, chronic obstructive pulmonary disease (COPD, includes emphysema and chronic bronchitis), and HIV/AIDS.

Metabolic syndrome is a combination of medical disorders that, when they occur together, increase the risk of developing cardiovascular disease and diabetes. Metabolic syndrome is also known as metabolic syndrome X, cardiometabolic syndrome, syndrome X, insulin resistance syndrome, Reaven's syndrome (named for Gerald Reaven), and CHAOS (in Australia). In one aspect, the invention relates to a method for treating, alleviating, or preventing a metabolic disorders, wherein the disorder is liver disease associated with metabolic syndrome.

Some of the more common genetic metabolic disorders include: lysosomal storage diseases such as congenital lipodystrophy, Hurler syndrome, Niemann-Pick disease, Tay-Sachs disease, Gaucher disease, Fabry disease, Krabbe disease, galactosemia, maple syrup urine disease, phenylketonuria (PKU); glycogen storage diseases; mitochondrial disorders; Friedreich ataxia; peroxisomal disorders including Zellweger syndrome, adrenoleukodystrophy; metal metabolism disorders such as Wilson disease, hemochromatosis, organic acidemias: methylmalonic acidemia and propionic acidemia and urea cycle disorders: ornithine transcarbamylase deficiency and citrullinemia.

In one aspect, the invention relates to methods of treating, alleviating, and/or preventing dyslipidemia in a subject by administering to the subject in need thereof an effective amount a compound of the invention. Dyslipidemia is an abnormal amount of lipids (e.g. cholesterol and/or fat) in the blood. In one aspect dyslipidemias are hyperlipidemias; that is, an elevation of lipids in the blood. This is often due to diet and lifestyle. Prolonged elevation of insulin levels can also lead to dyslipidemia. Likewise, increased levels of O-Glc-NAc transferase (OGT) may cause dyslipidemia. Examples of dyslipidemias include: hyperlipidemia; hypercholesteremia (familial hypercholesterolemia; hyperglyceridemia; hypertriglyceridemia; hypolipidemia; hypocholesterolemia; hyperlipoproteinemia; hyperchylomicronemia; hypolipoproteinemia; abetalipoproteinemia; Tangier disease; combined hyperlipidemia (both LDL and triglycerides).

In one aspect, the invention relates to methods of treating, alleviating, and/or preventing lipodystrophy in a subject by administering to the subject in need thereof an effective amount a compound of the invention. Types of lypodystrophies include HIV-associated lipodystrophy, congenital lipodystrophies such as congenital generalized lipodystrophy (Beradinelli-Seip syndrome), familial partial lipodystrophy, acquired lipodystrophy, acquired partial lipodystrophy (Barraquer-Simons syndrome), acquired generalized lipodystrophy, centrifugal abdominal lipodystrophy (lipodystrophia centrifugalis abdominalis infantilis), lipoatrophia annularis (Ferreira-Marques lipoatrophia), and localized lipodystrophy.

In one aspect, the invention relates to methods of treating, alleviating, and/or preventing polycystic ovarian syndrome in a subject by administering to the subject in need thereof an effective amount a compound of the invention.

Diabetes

In some aspects, the invention relates to methods of treating, alleviating, and/or preventing diabetes in a subject by administering to the subject in need thereof an effective amount a compound of the invention. In one aspect, the diabetes is type 1 diabetes. In one aspect, the diabetes is type 2 diabetes. Diabetes is a disease in which blood glucose, or sugar, levels are too high. Glucose comes from the foods that are eaten. Insulin is a hormone that helps the glucose get into cells to give them energy. With type 1 diabetes, the body does not make insulin. With type 2 diabetes, the more common type, the body does not make or use insulin well. Without enough insulin, the glucose stays in blood. In one aspect, the diabetes is gestational diabetes.

The cells located within the islets of Langerhans of the pancreas secrete insulin. In type 2 diabetes, it is these beta cells of the pancreas that fail to produce enough insulin to meet the body's demand, in part because of an acquired decrease in beta-cell mass. The process leading to type 1 (insulin-dependent) diabetes appears to start when the immune system recognizes and attacks proteins on the surface of the beta cells, possibly mistaking them for proteins on an invading organism. Over the course of years, the beta cells are gradually destroyed. Once most of them are gone, the symptoms of diabetes begin to appear.

The ability to induce beta-cell regeneration with small molecules e.g., a compound of the invention would transform diabetes therapy. The path to restoration of pancreatic beta-cell mass includes protection of beta cells from autoimmune attack (type 1 diabetes), and protection of beta cells from the deleterious effects of glucose and free fatty acids (type 2 diabetes). The current standard of care for type 1 diabetes which is caused by autoimmune destruction of beta cells is insulin injection; no small molecule interventions have been approved for clinical use.

Type 1 Diabetes

Cytokine-induced beta-cell apoptosis is important to the etiology of type 1 diabetes. This process involves a set of signaling cascades initiated by interleukin-1β (IL-1β), interferon-γ (IFN-γ), and tumor necrosis factor-α (TNF-α). IL-1β and TNF-α induce NFκB expression, and downstream activation of gene expression is thought to occur through nitric oxide (NO) signaling, which increases endoplasmic reticulum stress-response pathways and decreases beta cell-specific functions. NO is a highly reactive molecule that inhibits the electron-transport chain, decreasing glucose oxidation rates, ATP generation, and insulin production; cellular nitrite is more stable and serves as a surrogate marker for NO. NFκB activation and IFN-γ-induced STAT-1 signaling both work together to induce beta-cell apoptosis. The downstream effector of this cascade, caspase-3, mediates apoptosis and the loss of GSIS.

Small molecules that increase beta-cell survival in the presence of cytokines could be of potential clinical benefit to early-stage type 1 diabetic patients. Previous studies describe small molecules that were discovered because of their antioxidant or anti-inflammatory effects. However, an important role for histone deacetylases (HDACs) has recently been uncovered, which demonstrates that small-molecule inhibition of HDACs with trichostatin A (TsA) or suberoylanilide hydroxamic acid (SAHA) prevents cytokine-induced beta-cell death, presumably by decreasing NFκB transactivation. ITF2357, another broad-spectrum HDAC inhibitor, has activity in vivo, protecting mouse islets from cytokines and preventing hyperglycemia in streptozocin-treated mice. Narrowing down the HDAC isoform responsible for this process, and targeting it specifically with small molecules, would avoid the liabilities involved with inhibiting many HDAC isoforms with these known broad inhibitors. An HDAC3 selective molecule such as a compound of the invention has potential for use in the prevention and/or treatment of type 1 diabetes.

Type 2 Diabetes

Failure of pancreatic β cells to compensate for insulin resistance is a prerequisite for the development of type 2 diabetes. Sustained elevated circulating levels of free fatty acids and glucose contribute to β-cell failure. Non-selective inhibitors of HDACs improve oxidative capacity in insulin sensitive tissues, but until the present invention the effects on β-cell glucolipotoxicity had not yet been investigated. The present invention provides selective HDAC3 inhibitors that can protect pancreatic β-cells from glucolipotoxicity by reducing reactive oxygen species (ROS) production, endoplasmic reticulum (ER) stress-induced apoptotic signally via JNK and CHOP and apoptosis via the intrinsic (mitochondrial) death pathway. Accordingly, compounds of the invention improve glycemia and increase insulin secretion.

Specifically, in type 2 diabetes, glucolipotoxicity, i.e. the inhibitory and proapoptotic actions of sustained elevated circulating levels of non-esterified fatty acids (NEFAs) and glucose is considered to be a major pathogenetic factor in progressive pancreatic β-cell failure and loss executed by oxidative stress (Carpentier, A., et al., (1999) Am. J. Physiol 276, E1055-E1066; Lenzen, S. (2008) Biochem. Soc. Trans. 36, 343-347; Keaney, J. F., Jr., et al., (2003) Arterioscler. Thromb. Vasc. Biol. 23, 434-439) and apoptosis in type 2 diabetic patients (Butler, A. E., et al., (2003) Diabetes 52, 102-110). β cells are highly sensitive to oxidative damage due to weak antioxidant defense mechanisms. (Lenzen, S., et al., (1996) Free Radic. Biol. Med. 20, 463-466.)

The dysmetabolic state in type 2 diabetes is associated with epigenetic alterations via posttranslational modifications of histone and non-histone proteins, (Ling, C. & Groop, L. (2009) Diabetes 58, 2718-2725), e.g. methylations and acetylations that affect protein expression and function. The enzyme families of histone acetyl transferases and deacetylases dynamically and differentially determine the protein acetylation status (Choudhary, C., et al., (2003) (2009) Science 325, 834-840). Two families of histone acetylases (HDACs) exist; the classical $Zn^{2+}$-dependent HDACs and the NAD+-dependent sirtuins (SIRT1-7). The classical HDACs are subdivided into three phylogenetic groups: Class I (HDAC1, HDAC2, HDAC3 and HDAC8), Class II (IIa: HDAC4, HDAC5, HDAC7 and HDAC9, IIb: HDAC6 and HDAC10) and Class IV (HDAC11) (de Ruijter, A. J., et al., (2003) Biochem. J. 370, 737-749), and all are expressed by the β cell (Lundh, M., Christensen, et al., (2010) Diabetologia 53, 2569-2578).

Non-selective histone deacetylase inhibitors (HDACi) improve metabolic control in type 2 diabetic models by increasing the oxidative capacity in liver, muscle and white adipose tissue. (Shimazu, T., et al. (2013) Science 339, 211-214; Galmozzi, A., Mitro, et al. (2012) Diabetes 62, 732-742). The results presented herein show that selective inhibition of HDAC3 can protect β cells against fatty-acid and glucose induced toxicity (FIGS. 8-13). Mechanistically, HDAC inhibition e.g. using a compound of the invention can counter-act the induced formation of ROS production, activation of the intrinsic pathway and apoptotic signals induced by ER stress (FIG. 14).

In the lab, the fatty acid palmitate is often used to mimic the process of fatty acid induced beta-cell apoptosis, which differs from cytokine-induced apoptosis in that endoplasmic reticulum (ER) stress appears to be involved in fatty acid-induced apoptosis only. The chemical chaperones sodium phenylbutyrate and tauroursodeoxycholic acid have been shown to protect beta cells from palmitate-induced apoptosis, and are now being tested in clinical trials for their effects on body fat distribution and peripheral insulin sensitivity. These compounds however, have multiple effects in cells, and may not be specific to this process. A more selective manner of protecting beta cells from fatty acid-induced apoptosis is needed for the treatment of type 2 diabetes. The examples of the application show that compounds of the invention can protect pancreatic β-cells from palmitate and high glucose induced apoptosis.

Glucolipotoxicity is known to cause oxidative stress in β cells via increased ROS formation from mitochondria (Lenzen, S. (2008) Biochem. Soc. Trans. 36, 343-347). The examples of the application show that selective HDAC3 inhibition can reduce ROS formation and activation of the intrinsic apoptotic pathway. Accordingly, selective HDAC3 inhibition e.g., using a compound of the invention decreases glucolipotoxicity-induced loss of mitochondrial activity, and this correlates with a decrease in ROS generation.

ROS generation is also known to be tightly coupled to ER stress and markers of ER stress are observed in liver and adipose tissue in models of obesity (Ozcan, U., et al., (2004) Science 306, 457-461) and in islets from type 2 diabetic patients (Laybutt, D. R., et al., (2007) Diabetologia 50, 752-763). High glucose or palmitate induced mitochondrial ROS is associated with ER stress and ROS scavengers reduce palmitate-induced ER stress in pancreatic β cells (Tang, C., et al. (2012) Diabetologia 55, 1366-1379; Lin, N. et al., (2012) Endocrine. 42, 107-117). ER stress causes activation of the unfolding protein response (UPR) resulting in either resolution of ER stress or, in case of severe or prolonged stress, induction of apoptosis (Hotamisligil, G. S. (2010) Cell 140, 900-917). Glucolipotoxic β-cell ER stress results in apoptosis through activation of c-Jun N-terminal kinase (JNK) and the transcription factor C/EBP homologous protein (CHOP) (Cunha, D. A., Hekerman, et al. (2008) J. Cell Sci. 121, 2308-2318). CHOP is linked to increased β-cell oxidative stress (Song, B., et al., (2008) J. Clin. Invest 118, 3378-3389) and ROS activates JNK (Lin, N., et al., (2012) Endocrine. 42, 107-117; Hou, N., et al., (2008) Endocrinology 149, 1654-1665). These observations support the close synergistic interdependence of ER and mitochondrial death pathways in β-cell glucolipotoxicity. The examples of the application show that selective HDAC3 inhibition e.g., using a compound of the invention reduces ER stress.

The β-cell protective molecular mechanisms of the compounds of the invention was examined by looking at the effect of the compounds on glucolipotoxicity induced changes in the three main pathways of the UPR; the IRE-pathway (Xbp1s, JNK), the PERK-pathway (Atf4, Atf3 and CHOP) and the ATF6-pathway (Bip). The results are described in the examples.

Pharmacological targeting of HDAC3 may offer several therapeutic benefits to patients with type 2 diabetes by 1) improving oxidative metabolism in muscle and adipose tissue (Galmozzi, A., et al. (2012) Diabetes 62, 732-742); 2) by preventing B-cell glucolipotoxicity; and 3) by counter-acting inflammatory B-cell damage (Lundh, M., et al. (2012) Diabetologia 55, 2421-2431; Chou, D. H., et al., (2012) Chem. Biol. 19, 669-673; Larsen, C. M., et. al., (2007) N. Engl. J. Med. 356, 1517-1526). The protective action of HDAC3 inhibition on direct β-cell cytokine-mediated damage may synergize with the effects of HDAC3 inhibition on macrophage activation and recruitment (Chen, X., et al., (2012) Proc. Natl. Acad. Sci. U. S. A 109, E2865-E2874).

Adverse effects such as anemia and thrombocytopenia of non-selective HDAC inhibition in clinical trials in cancer have been of major concern (Undevia, S. D., et al., (2004) Ann. Oncol. 15, 1705-1711; Fraczek, J., et al., (2013) Expert. Opin. Drug Metab Toxicol. Epub ahead of print), likely through inhibition of HDAC1 and HDAC2 as these are essential for megakaryocyte differentiation (Wilting, R. H., et al., (2010) EMBO J. 29, 2586-2597). In contrast to HDAC1,2,3 selective inhibitors such as CI-994 and MS-275, which demonstrate thrombocytopenic dose limiting toxicities, compound 1 does not perturb the growth of human megakaryocyte progenitors (FIG. 17) and may therefore provide a larger therapeutic window.

HDAC3 selective inhibition protects pancreatic β cells in models of type 2 diabetes in vitro and in vivo. Compounds of the invention have been shown to be HDAC3 selective inhibitors, which are useful as therapeutic agent for the treatment of type 2 diabetes.

Liver Disease

In one aspect, the invention relates to methods of treating, alleviating, and/or preventing liver disease in a subject by administering to the subject in need thereof an effective amount a compound of the invention. In one aspect, the liver disease is liver heptosteatosis. In one aspect, the liver disease is fatty liver disease. In one aspect, the liver disease is NASH (Non-alcoholic steatohepatitis). In one aspect, the liver disease is NAFLD (Non-alcoholic fatty liver disease). In one aspect, the liver disease is fatty liver disease.

Neoplastic Disease

In some aspects, the invention relates to methods of selectively inducing terminal differentiation, and arresting cell growth and/or apoptosis of neoplastic cells, thereby inhibiting proliferation of such cells. The compounds of the present invention are useful in treating, alleviating, and/or preventing cancer in a subject.

The term "cancer" refers to any cancer caused by the proliferation of neoplastic cells, such as solid tumors, neoplasms, carcinomas, sarcomas, leukemias, lymphomas and the like. In particular, cancers that may be treated, alleviated and/or prevented by the compounds of the invention include, but are not limited to: cardiac cancer, lung cancer, gastrointestinal cancer, genitourinary tract cancer, liver cancer, nervous system cancer, gynecological cancer, hematologic cancer, skin cancer, and adrenal gland cancer.

In some embodiments, the compounds of the invention relate to treating, alleviating, or preventing cardiac cancers selected from sarcoma (angiosarcoma, fibrosarcoma, rhabdomyosarcoma, liposarcoma), myxoma, rhabdomyoma, fibroma, lipoma and teratoma.

In some embodiments, the compounds of the invention relate to treating, alleviating, or preventing lung cancer selected from bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma.

In some embodiments, the compounds of the invention relate to treating, alleviating or preventing gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), and large bowel (adenocarcinoma, tubular adenoma, villous adenoma, hamartoma, leiomyoma).

In some embodiments, the compounds of the invention relate to treating, alleviating, and/or preventing genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

In some embodiments, the compounds of the invention relate to treating, alleviating, and/or preventing liver cancer selected from hepatoma (hepatocellular carcinoma), cholangiocarcinoma, hepatoblastoma, angiosarcoma, hepatocellular adenoma, and hemangioma.

In some embodiments, the compounds of the invention relate to treating, alleviating, and/or preventing bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors.

In some embodiments, the compounds of the invention relate to treating, alleviating, and/or preventing nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In some embodiments, the compounds of the invention relate to treating, alleviating, and/or preventing gynecological cancer selected from uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In some embodiments, the compounds of the invention relate to treating, alleviating, and/or preventing skin cancer selected from malignant melanoma, basal cell carcinoma, squamous cell carcinoma, Karposi's sarcoma, moles dysplastic nevi, lipoma, angioma, dermatofibroma, keloids, and psoriasis.

In some embodiments, the compounds of the invention relate to methods of treating, alleviating, and/or preventing adrenal gland cancer selected from neuroblastoma.

In some embodiments, the instant compounds are useful in the treatment, alleviation, and/or preventing of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

Hematologic Diseases

In some aspects, the invention relates to methods of treating, alleviating, or preventing hematolic diseases. Hematologic diseases include abnormal growth of blood cells which can lead to dysplastic changes in blood cells and hematologic malignancies such as various leukemias. Examples of hematologic diseases include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chormosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia. Sickle cell disease is attributable to homozygous inheritance of a single amino acid substitution in the β-globin gene that leads to polymerization of deoxygenated hemoglobin, deformation of red blood cells, microvascular occlusion, hemolysis, and consequent disease manifestations, including pain, strokes, and pulmonary complications (Bunn H F, 1997, J. Med. 337:762-769). Abundant biochemical, epidemiological, and clinical evidence have shown that a high level of γ globin, the fetal form of β globin, inhibits the aberrant polymerization of sickle hemoglobin and ameliorates the disease phenotype. The only Food and Drug Administration (FDA)-approved drug for sickle cell disease, hydroxyurea, causes significant induction of fetal hemoglobin, decreased disease severity, and benefits overall mortality (Letvin et al., 1984, N Engl J Med 310: 869-873; Platt O S, et al., 1984, J Clin Invest 74:652-656; Charache S, et al., 1995, N Engl J. Med 332: 317-1322; Steinberg M H, et al., 2003, JAMA 289:1645-1651). Nevertheless, hydroxyurea has bone marrow-suppressive effects and is ineffective in a significant portion of patients (Charache S, et al.; Steinberg M H, et al., 2003; Steinberg M H, 1999, N Engl J. Med 340:1021-1030). A drug that induces fetal hemoglobin more substantially with less myelosuppression would be expected to have greater therapeutic utility in sickle cell disease.

Transcriptional regulation of the human globin gene locus has been investigated intensively. Gamma-globin gene expression is influenced by transcription factors (GATA-1, EKLF, NF-E4p22, Ikaros) and chromatin modifying enzymes [SWI/SNF complex, HATs, and histone deacetylase (HDACs)] as part of multiprotein complexes, and a unique, dynamic chromatin structure termed the β-globin active chromatin hub (βACH) (8-11). Polymorphisms in BCL11A, a transcriptional repressor, alter baseline fetal hemoglobin levels, and a multiprotein complex containing BCL11a binds to the β-globin locus, resulting in repression of γ-globin expression (Menzel S, et al., 2007, Nat Genet 39:1197-1199; Lettre G, et al., 2008, Proc Natl Acad Sci USA 105:11869-11874; Sankaran V G, et al., 2008, Science 322:1839-1842; Uda M, et al., 2008, Proc NATL Acad Sci USA 105:1620-1625; Sankaran V G, et al., 2009, Nature 460:1093-1097). Despite this granularity, discrete targets amenable to ligand discovery efforts have not been identified and functionally validated.

Formulations

The compounds of the invention may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli*, Bacillus calmatte-guerin, *Shigella, Lactobacillus*); Live viral vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The term an "effective amount" of a compound of the invention refers to the amount necessary or sufficient to realize a desired biologic effect. For example, an effective amount of a compound of the invention is that amount sufficient to treat a condition. In another aspect, an effective amount of a compound is that amount sufficient to alleviate a condition. In another aspect, an effective amount of a compound is that amount sufficient to prevent a condition. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the condition being treated, the particular compounds being administered the size of the subject, or the severity of the condition.

The compounds of the invention may be administered by any route known, such as, for example, orally, transdermally, intravenously, cutaneously, subcutaneously, nasally, intramuscularly, intraperitoneally, intracranially, and intracerebroventricularly.

In certain embodiments, compounds of the invention are administered at dosage levels greater than about 0.001 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can also be administered to a subject.

In one embodiment, the compound of the invention is administered once-daily, twice-daily, or three-times daily. In one embodiment, the compound of the invention is administered continuously (i.e., every day) or intermittently (e.g., 3-5 days a week). In another embodiment, administration could be on an intermittent schedule.

Further, administration less frequently than daily, such as, for example, every other day may be chosen. In additional embodiments, administration with at least 2 days between doses may be chosen. By way of example only, dosing may be every third day, bi-weekly or weekly. As another example, a single, acute dose may be administered. Alternatively, compounds of the invention can be administered on a non-regular basis e.g., whenever symptoms begin. For any compound described herein the effective amount can be initially determined from animal models.

Toxicity and efficacy of the compounds of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds of the invention for use in humans. The dosage of such agents lies preferably within a range of circulating concentrations that include the ED50 with little or no toxicity. The dosage may vary within this range depending upon the dosage form employed and the route of administration utilized. For any compound used in the method of the invention, the effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Multiple doses of the compounds of the invention are also contemplated.

The formulations of the invention are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of one or more compounds of the invention can be administered to a subject by any mode that delivers the compound(s) to the desired surface, e.g., mucosal, systemic. Administering the pharmaceutical composition of the present invention may be accomplished by any means known to the skilled artisan. Compounds of the invention may be administered orally, transdermally, intravenously, cutaneously, subcutaneously, nasally, intramuscularly, intraperitoneally, intracranially, or intracerebroventricularly.

For oral administration, one or more compounds of the invention can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of one or more compounds of the invention. The compound(s) may be chemically modified so that oral delivery of the derivative is efficacious. Generally, the chemical modification contemplated is the attachment of at least one moiety to the compound itself, where said moiety permits (a) inhibition of proteolysis; and (b) uptake into the blood stream from the stomach or intestine. Also desired is the increase in overall stability of the compound(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4: 185-189. Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used. The compound of the invention can be included in the formulation as fine multiparticulates in the form of granules or pellets of particle size about 1 mm. The formulation of the material for capsule administration could also be as a powder, lightly compressed plugs or even as tablets. The compound of the invention could be prepared by compression.

Colorants and flavoring agents may all be included. For example, the compound of the invention may be formulated (such as by liposome or microsphere encapsulation) and then further contained within an edible product, such as a refrigerated beverage containing colorants and flavoring agents.

One may dilute or increase the volume of compound delivered with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell. Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic together to form a hard tablet and include materials from natural products such as *acacia*, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the compound of the invention to prevent sticking during the formulation process. Lubricants may be used as a layer between the compound and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compound into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the invention. The compound is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63: 135-144 (leuprolide acetate); Braquet et al., 1989, Journal of Cardiovascular Pharmacology, 13(suppl. 5): 143-146 (endothelin-1); Hubbard et al., 1989, Annals of Internal Medicine, Vol. IJJ, pp. 206-212 (a1-antitrypsin); Smith et al., 1989, J. Clin. Invest. 84: 1 145-1 146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified compound may also be prepared in different formulations depending on the type of chemical modification or the type of device employed. Formulations suitable for use with a nebulizer, either jet or ultrasonic, will typically comprise compound dissolved in water at a concentration of about 0.1 to 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., 50 to 90% by weight of the formulation. The compound should most advantageously be prepared in particulate form with an average particle size of less than 10 mm (or microns), most preferably 0.5 to 5 mm, for most effective delivery to the distal lung.

Nasal delivery of a compound of the invention is also contemplated. Nasal delivery allows the passage of a compound of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture diihensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compound, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249: 1527-1533, 1990, which is incorporated herein by reference.

The compounds of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a compound of the invention optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the invention, and with each other, in a manner such that there is no interaction which would substantially impair the desired pharmaceutical efficiency.

The compounds of the invention may be delivered to the brain using a formulation capable of delivering a compound across the blood brain barrier. One obstacle to delivering compounds to the brain is the physiology and structure of the brain. The blood-brain barrier is made up of specialized capillaries lined with a single layer of endothelial cells. The region between cells is sealed with a tight junction, so the only access to the brain from the blood is through the endothelial cells. The barrier allows only certain substances, such as lipophilic molecules through and keeps other harmful compounds and pathogens out. Thus, lipophilic carriers are useful for delivering non-lipohilic compounds to the brain. For instance, DHA, a fatty acid naturally occurring in the human brain has been found to be useful for delivering drugs covalently attached thereto to the brain (Such as those described in U.S. Pat. No. 6,407,137). U.S. Pat. No. 5,525,727 describes a dihydropyridine pyridinium salt carrier redox system for the specific and sustained delivery of drug species to the brain. U.S. Pat. No. 5,618,803 describes targeted drug delivery with phosphonate derivatives. U.S. Pat. No. 7,119,074 describes amphiphilic prodrugs of a therapeutic compound conjugated to an PEG-oligomer/polymer for delivering the compound across the blood brain barrier. The compounds described herein may be modified by covalent attachment to a lipophilic carrier or co-formulation with a lipophilic carrier. Others are known to those of skill in the art.

The compounds of the invention may be delivered with other methods for enhancing memory retrieval or treating other symptoms or causes of disorders associated with the memory loss. For instance, environmental enrichment (EE) has been used for enhancing memories. EE involves creating a stimulating environment around a subject. Other therapeutics may also be combined to treat the underlying disorder or to enhance memory.

Combination Therapies

The invention includes combination therapies including the methods of treating, alleviating, and/or preventing conditions described herein. Combination therapy includes administering one or more compounds of the invention in combination with one or more pharmaceutically active ingredients or exposing the subject to cognitive behavioral therapy (CBT), psychotherapy, behavioral exposure treatments, virtual reality exposure (VRE) or cognitive remediation therapy.

In one aspect, the combination therapy is for a method of treating, alleviating, or preventing a neurological disorder. In one aspect, the combination therapy is for methods of treating, alleviating, or preventing Alzheimer's disease. The combination therapies comprise the administration of an effective amount of one or more (e.g. one) compounds of the invention and the administration of an effective amount of one or more (e.g., one) other pharmaceutically active ingredients (e.g., drugs). The compounds of the invention and the other pharmaceutically active ingredients can be administered separately (i.e., each is in its own separate dosage form), or the compounds of the invention can be combined with the other pharmaceutically active ingredients in the same dosage form.

Pharmaceutically active ingredients that are useful in combination therapies of the invention include e.g., BACE inhibitors (beta secretase inhibitors), muscarinic antagonists, cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; GABA inverse agonists; inhibitors of amyloid aggregation; glycogen synthase kinase beta inhibitors; tau kinase inhibitors (e.g., GSK3beta inhibitors, cdk5 inhibitors, ERK inhibitors), promoters of alpha secretase activity; PDE-10 inhibitors and cholesterol absorption inhibitors. Further examples of pharmaceutically active ingredients that are useful for combination therapies of the invention are (+)-2,3-dihydro-5,6-dimethoxy-2-[[1-(phenylmethyl)-4-piperidinyl]methy-1]-1H-inden-1-one hydrochloride, i.e., donepezil hydrochloride, available as the Aricept™ brand of donepezil hydrochloride, Exelon (rivastigmine), Cognex (tacrine), anti-Abeta vaccine (active immunization), amyloid precursor protein (APP) ligands, agents that upregulate insulin degrading enzyme and/or neprilysin, cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe, fibrates (for example, clofibrate, Clofibride, Etofibrate, Aluminium Clofibrate), LXR agonists, LRP mimics, 5-HT6 receptor antagonists, nicotinic receptor agonists, H3 receptor antagonists, other histone deacetylase inhibitors, hsp90 inhibitors, muscarinic receptor agonists, 5-HT6 receptor antagonists mGluR1 or mGluR5 positive allosteric modulators or agonists, mGluR2/3 antagonists, anti-inflammatory agents that can reduce neuroinflammation, prostaglandin EP2 receptor antagonists, PAI-1 inhibitors and agents that can induce Abeta efflux such as gelsolin.

Examples of combination therapies of the compounds of the invention with other pharmaceutically active ingredients include combinations with: anti-Alzheimer's agents, beta-secretase inhibitors, gamma-secretase inhibitors, HMG-CoA reductase inhibitors, NSAID's including ibuprofen, N-methyl-D-aspartate (NMDA) receptor antagonists, such as memantine, cholinesterase inhibitors such as galantamine, rivastigmine, donepezil, and tacrine, vitamin E, CB-I receptor antagonists or CB-I receptor inverse agonists, antibiotics such as doxycycline and rifampin, anti-amyloid antibodies, or other pharmaceutically active ingredients that affect receptors or enzymes that either increase the efficacy, safety, convenience, or reduce unwanted side effects or toxicity of the compounds of the invention. The compounds of the invention may also be delivered in a cocktail of multiple HDAC inhibitors. Combination therapies of the invention may be in either unit dose or kit form.

The compounds of the invention are also useful in combination with known pharmaceutically active ingredients such as anti-cancer agents for treating, alleviating and/or preventing cancer. Combinations of the presently disclosed compounds with other anti-cancer or chemotherapeutic agents are within the scope of the invention. Examples of such agents can be found in Cancer Principles and Practice of Oncology by V. T. Devita and S. Hellman (editors), 6.sup.th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The compounds of the invention are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Additional combination therapies are discussed herein under the extinction learning section.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

The invention provides combination therapy for treating, alleviating, and/or preventing diabetes (type 1 or type 2) in a subject comprising administering to the subject in need thereof an effective amount of one or more compounds of the invention or a pharmaceutically acceptable salt, hydrate, solvate, or prodrug thereof and (2) an anti-diabetic drug. The antidiabetic drug is any anti-diabetic drug. In one aspect, the anti-diabetic drug is a biguanide such as metformin, a thiazolidinedione such as rosiglitazone, an incretin mimetic such as exenatide, a dipeptidyl peptidase-4 inhibitors such as sitagliptin or injected insulin.

Combination therapy can include administering one or more compounds of the invention in combination with insulin therapy for treating, alleviating, and/or preventing diabetes (type 1 or type 2). Insulin treatment replaces or supplements the body's own insulin, restoring normal or near-normal blood sugar levels. Many different types of insulin treatment can successfully control blood sugar levels. There are several different types of insulin. These types are classified according to how quickly they begin working and how long the insulin lasts: Rapid-acting (eg, insulin lispro [Humalog®], insulin aspart [Novolog®], and insulin glulisine [Apidra®]); Short-acting (eg, insulin regular); Intermediate-acting (eg, insulin NPH); Long-acting (eg, insulin glargine [Lantus®], insulin detemir [Levemir®]). Insulin types can be used in combination to achieve around-the-clock blood sugar control. Combination therapy can also include administering one or more compounds of the invention in combination with another anti-diabetic drug for lowering glucose levels in a subject e.g., metformin.

The following Examples are illustrative and should not be interpreted in any way so as to limit the scope of the invention.

EXAMPLES

Procedure A: Synthesis of
4-acetamido-N-(2-amino-4-fluorophenyl)benzamide,
Compound 1

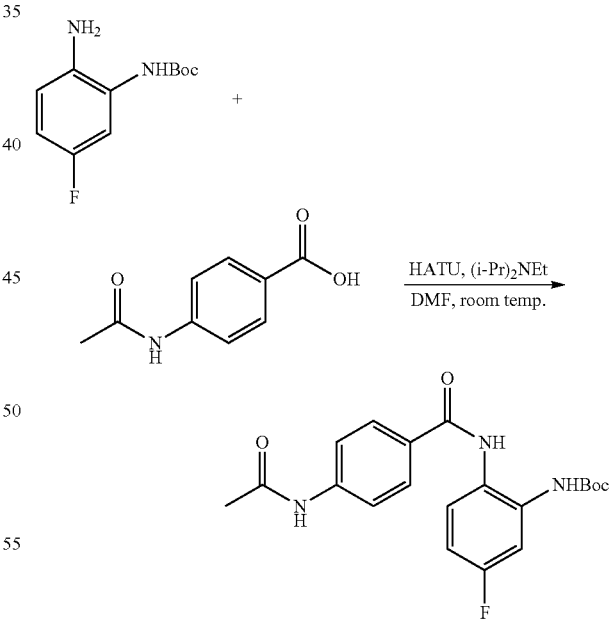

To solution of commercially available tert-butyl 2-amino-5-fluorophenylcarbamate (610 mg, 2.70 mmol) and 4-acetamidobenzoic acid (725 mg, 4.04 mmol) in DMF (2 mL) at room temperature was added dropwise a solution of HATU (1.54 g, 4.04 mmol) in DMF (1 mL) then N-ethyl-N-isopropylpropan-2-amine (1.337 ml, 8.09 mmol). The resulting reaction was stirred at room temperature for 14 h. The reaction was then quenched by sodium bicarbonate.

Some of the desired product precipitated out of solution and was filtered off as a white solid. The remaining solution was extracted with ethyl acetate. The combined organic layers were washed with brine, then dried over sodium sulfate, filtered and concentrated. The product was purified by column chromatography (silica gel, 20-80% EtOAc/hexanes) to obtain the desired product (0.64 g, 61% yield).

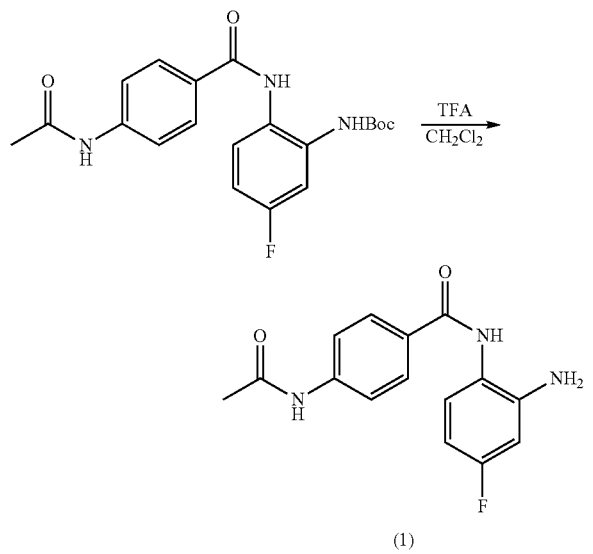

To a solution of tert-butyl 2-(4-acetamidobenzamido)-5-fluorophenylcarbamate (640 mg, 1.652 mmol) in dichloromethane (3 mL) at room temperature was added trifluoroacetic acid (1265 μL, 16.52 mmol). The resulting solution was stirred for 2 h. The reaction was then quenched with a saturated aqueous solution of sodium bicarbonate. The desired product crashed out of solution and was filtered. The precipitate was washed with cold EtOAc to obtain the desired product as a white solid. The aqueous phase was washed with EtOAc (3×10 mL). The combined organic layers were washed with water then brine, dried over sodium sulfate, filtered and concentrated. The product was purified by column chromatography (silica gel, 20% EtOAc/hexanes) to obtain the desired product. The combined yield was 0.29 g, 61% yield of compound 1. ESI+ MS: m/z 288.3 ([M+H]+); 1HNMR (500 MHz, d6-DMSO): 10.17 (s, 1H), 9.47 (s, 1H), 7.92 (d, J=8.5 Hz, 2H), 7.68 (d, J=8.5 Hz, 2H), 7.12-7.08 (m, 1H), 6.53 (dd, J=3.0, 11.5 Hz, 1H), 6.35 (dt, J=3.0, 8.5 Hz, 1H), 5.18 (s, 2H), 2.08 (s, 3H).

One skilled in the art will recognize that other compounds described below can be prepared in a similar manner to the procedure A described above.

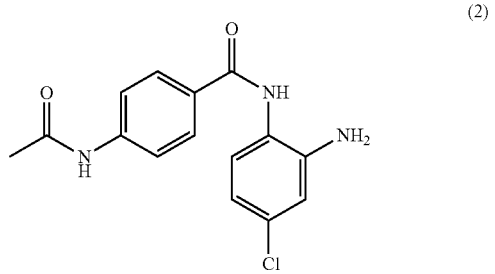 [SMILES: CC(=O)Nc1ccc(C(=O)Nc2ccc(Cl)cc2N)cc1]

4-acetamido-N-(2-amino-4-chlorophenyl)benzamide, compound 2, can be prepared by substituting tert-butyl 2-amino-5-fluorophenylcarbamate with tert-butyl 2-amino-5-chlorophenylcarbamate. ESI+ MS: m/z 304 ([M+H]+); 1H NMR (300 MHz, DMSO) δ 10.20 (s, 1H), 9.53 (s, 1H), 7.92 (d, J=9.0 Hz, 2H), 7.68 (d, J=9.0 Hz, 2H), 7.14 (d, J=6.0 Hz, 1H), 6.79 (d, J=3.0 Hz, 1H), 6.58 (dd, J=6.0, 3.0 Hz, 1H), 5.22 (s, 2H), 2.07 (s, 3H).

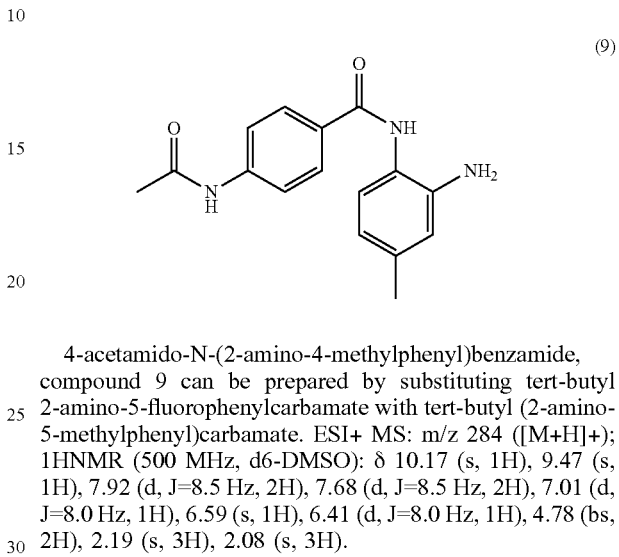

4-acetamido-N-(2-amino-4-methylphenyl)benzamide, compound 9 can be prepared by substituting tert-butyl 2-amino-5-fluorophenylcarbamate with tert-butyl (2-amino-5-methylphenyl)carbamate. ESI+ MS: m/z 284 ([M+H]+); 1HNMR (500 MHz, d6-DMSO): δ 10.17 (s, 1H), 9.47 (s, 1H), 7.92 (d, J=8.5 Hz, 2H), 7.68 (d, J=8.5 Hz, 2H), 7.01 (d, J=8.0 Hz, 1H), 6.59 (s, 1H), 6.41 (d, J=8.0 Hz, 1H), 4.78 (bs, 2H), 2.19 (s, 3H), 2.08 (s, 3H).

4-acetamido-N-(2-amino-6-fluorophenyl)benzamide, compound 3 can be prepared by substituting tert-butyl 2-amino-5-fluorophenylcarbamate with tert-butyl (2-amino-3-fluorophenyl)carbamate. ESI+ MS: m/z 288 ([M+H]+); 1HNMR (300 MHz, d6-DMSO): δ 10.22 (s, 1H), 9.40 (s, 1H), 7.96 (d, J=9.0 Hz, 2H), 7.70 (d, J=9.0 Hz, 2H), 7.01-6.97 (m, 1H), 6.56 (d, J=6.0 Hz, 1H), 6.40 (t, J=6.0, 1H), 3.40 (bs, 2H), 2.09 (s, 3H).

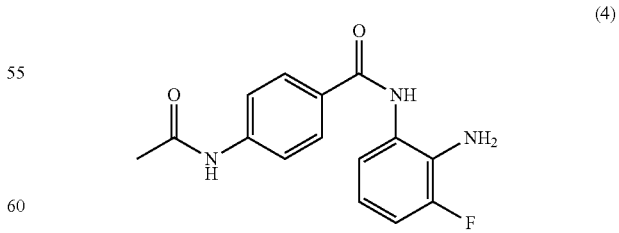

4-acetamido-N-(2-amino-3-fluorophenyl)benzamide, compound 4 can be prepared by substituting tert-butyl 2-amino-5-fluorophenylcarbamate with tert-butyl (2-amino-6-fluorophenyl)carbamate. ESI+ MS: m/z 288 ([M+H]+); 1HNMR (300 MHz, d6-DMSO): δ 10.21 (s, 1H), 9.69 (s, 1H), 7.93 (d, J=9.0 Hz, 2H), 7.69 (d, J=9.0 Hz, 2H), 7.03 (d, J=9.0 Hz, 1H), 6.98-6.90 (m, 1H), 6.62-6.54 (m, 1H), 4.86 (bs, 2H), 2.07 (s, 3H).

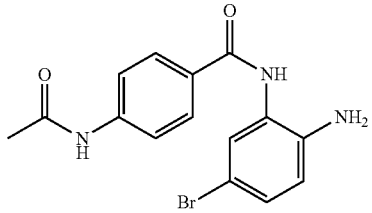

(5)

4-acetamido-N-(2-amino-5-bromophenyl)benzamide, compound 5 can be prepared by substituting tert-butyl 2-amino-5-fluorophenylcarbamate with tert-butyl (2-amino-4-bromophenyl)carbamate. ESI+ MS: m/z 348 ([M]+); 1HNMR (500 MHz, d6-DMSO): δ 10.19 (s, 1H), 9.54 (s, 1H), 7.92 (d, J=8.5 Hz, 2H), 7.69 (d, J=8.5 Hz, 2H), 7.38 (d, J=2.5 Hz, 1H), 7.10 (dd J=8.5, 2.5 Hz, 1H), 6.73 (d, J=8.5 Hz, 1H), 5.11 (bs, 2H), 2.08 (s, 3H).

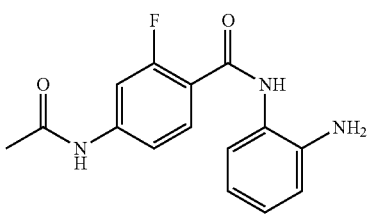

(12)

4-acetamido-N-(2-aminophenyl)-2-fluorobenzamide, compound 12 can be prepared by substituting tert-butyl 2-amino-5-fluorophenylcarbamate with tert-butyl(2-aminophenyl)carbamate and by substituting 4-acetamidobenzoic acid with 4-acetamido-2-fluorobenzoic acid. ESI+ MS: m/z 288 ([M+H]+); 1HNMR (300 MHz, d6-DMSO): δ 10.38 (s, 1H), 9.36 (s, 1H), 7.73-7.69 (m, 2H), 7.36-7.28 (m, 2H), 6.95 (t, J=6.0 Hz, 1H), 6.77 (d, J=6.0, 1H), 6.59 (t, J=6.0 Hz, 1H), 4.91 (s, 2H), 2.09 (s, 3H).

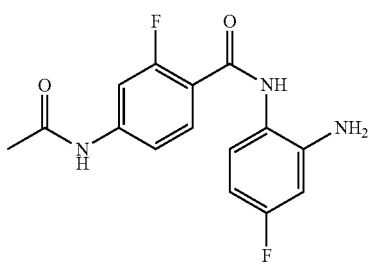

(6)

4-acetamido-N-(2-amino-4-fluorophenyl)-2-fluorobenzamide, compound 6 can be prepared by substituting 4-acetamidobenzoic acid with 4-acetamido-2-fluorobenzoic acid. ESI+ MS: m/z 306.3 ([M+H]+); 1H NMR (300 MHz, DMSO) δ 10.38 (s, 1H), 9.31 (s, 1H), 7.75-7.65 (m, 2H), 7.34 (dd, J=9.0, 3.0 Hz, 1H), 7.21 (dd, J=9.0, 6.0 Hz, 1H), 6.53 (dd, J=12.0, 3.0 Hz, 1H), 6.36 (td, J=12.0, 3.0 Hz, 1H), 5.23 (s, 2H), 2.09 (s, 4H).

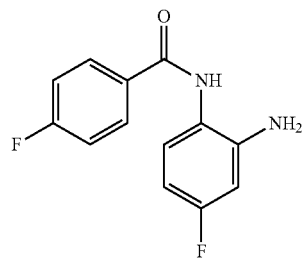

(8)

N-(2-amino-4-fluorophenyl)-4-fluorobenzamide, compound 8 can be prepared by substituting 4-acetamidobenzoic acid with 4-fluorobenzoic acid. ESI+ MS: m/z 249 ([M+H]+); 1HNMR (400 MHz, d6-DMSO): 9.59 (s, 1H), 8.07-8.03 (m, 2H), 7.33 (t, J=8.4 Hz, 2H), 7.10 (t, J=8.4 Hz, 1H), 6.53 (dd, J=11.2, 3.2 Hz, 1H), 6.38-6.32 (m, 1H), 5.23 (s, 2H).

Procedure B: Synthesis of 4-acetamido-N-(2-amino-4-(trifluoromethyl)phenyl)benzamide, Compound 10

A mixture of 4-acetamidobenzoyl chloride (0.38 g, 1.94 mmol), 2-nitro-4-(trifluoromethyl)aniline (0.20 g, 0.97 mmol) and pyridine (0.61 g, 7.76 mmol) in toluene (30 mL) was heated to reflux overnight. The reaction mixture was concentrated. The residue was partitioned between ethylacetate (25 mL) and a saturated aqueous solution of sodium bicarbonate (25 mL). The suspension was filtered and the resulting yellow solid was washed with ethyl acetate and hexanes (1/1) to afford the desired compound (0.19 g, 53% yield).

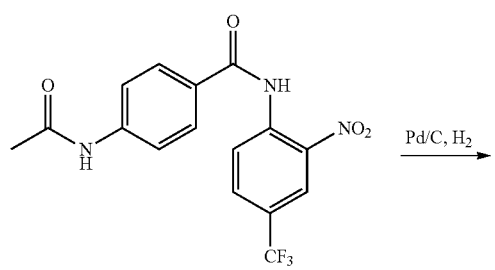

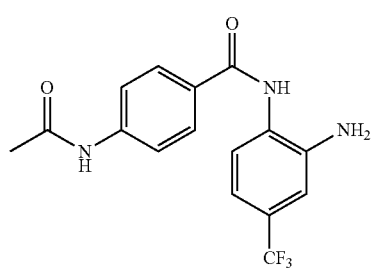

(10)

To a solution of 4-acetamido-N-(2-nitro-4-(trifluoromethyl)phenyl)benzamide (0.19 g, 0.517 mmol) in ethyl acetate (30 mL) was added Pd/C (50 mg). The reaction mixture was stirred for 2 h under hydrogen atmosphere. The catalyst was filtered off over Celite and the filtrate was concentrated in vacuo. The obtained solids were washed with ethylacetate and hexanes (⅓) to provide the desired product as a white solid (0.11 g, 63% yield). ESI+ MS: m/z 338 ([M+H]+); 1HNMR (500 MHz, d6-DMSO): δ 10.22 (s, 1H), 9.65 (s, 1H), 7.94 (d, J=9.0, 2H), 7.70 (d, J=9.0, 2H), 7.42 (d, J=8.5, 1H), 7.09 (d, J=1.5, 1H), 6.89 (dd, J=8.5, 1.5, 1H), 5.40 (s, 2H), 3.09 (s, 3H).

One skilled in the art will recognize that other compounds described below can be prepared in a similar manner to the procedures A and B described above.

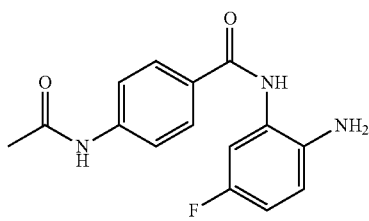 [SMILES: CC(=O)Nc1ccc(C(=O)Nc2cc(F)ccc2N)cc1]

(11)

4-acetamido-N-(2-amino-5-fluorophenyl)benzamide, compound 11 can be prepared by substituting tert-butyl 2-amino-5-fluorophenylcarbamate with 5-fluoro-2-nitroaniline in procedure A and using the hydrogenolysis in procedure B. ESI+ MS: m/z 288 ([M+H]+); 1HNMR (500 MHz, d6-DMSO): δ 10.21 (s, 1H), 9.55 (s, 1H), 7.92 (d, J=9.0, 2H), 7.70 (d, J=9.0, 2H), 7.16 (dd, J=10.0, 3.0, 1H), 6.82-6.75 (m, 2H), 4.82 (s, 2H), 2.08 (s, 3H).

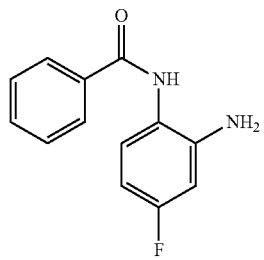 [SMILES: Nc1cc(F)ccc1NC(=O)c1ccccc1]

(7)

N-(2-amino-4-fluorophenyl)benzamide, compound 7 can be prepared by substituting 4-acetamidobenzoyl chloride with benzoyl chloride in procedure B and using the TFA deprotection in procedure A. ESI+ MS: m/z 231 ([M+H]+); 1HNMR (400 MHz, d6-DMSO): 9.57 (s, 1H), 7.97 (d, J=6.0 Hz, 2H), 7.56-7.48 (m, 3H), 7.10 (t, J=12.0 Hz, 1H), 6.54-6.52 (m, 1H), 6.36-6.33 (m, 1H), 5.21 (s, 1H).

Example 2

Brain and Plasma Concentration

The brain and plasma concentrations of Repligen 136 (30 mg/kg) and compound 1 (10 mg/kg) were compared in mice. Specifically, mice were injected with a single dose of compound and the concentration of compound was measured in the brain and plasma of mice at 8 time points. The samples were analyzed by LC-MS/MS.

FIG. 1 is a graph which shows a comparison of the brain and plasma exposure versus time. A table of the results is presented below. The concentration of Repligen 136 in the brain was not measurable after 2 hours. In comparison, compound 1 was still present in the brain after 8 hours. Compound 1 showed 30 times (dose normalized) better brain exposure in comparison to Repligen 136 as measured by Cmax and 120 times (dose normalized) better brain exposure measured by AUC. The concentration of compound 1 in plasma was also improved over Repligen 136. As shown in the table below, compound 1 had 30 times better exposure as measured by AUC than Repligen 136. These superior and improved brain penetration and exposure results of compound 1 over Repligen 136 are surprising and unexpected.

| | | Plasma | | | Brain | | | | |
| --- | --- | --- | --- | --- | --- | --- | --- | --- | --- |
| | | AUC Plasma μmol/L · hr | $T_{1/2}$ Plasma hr | Cmax Plasma μmol/L | AUC Brain μmol/L · hr | $T_{1/2}$ Brain hr | Cmax Brain μmol/L | Brain/Plasma Cmax | Brain/Plasma AUC |
| Repligen 136 | 30 mg/kg | 6.73 | 1.38 | 13.11 | 0.32 | 0.34 | 0.37 | 0.03 | 0.05 |
| Compound 1 | 10 mg/kg | 67.23 | 2.26 | 29.50 | 12.77 | 2.06 | 3.80 | 0.13 | 0.19 |

Example 3

Kinetics of the Inhibition of HDAC1

Figure 2A:
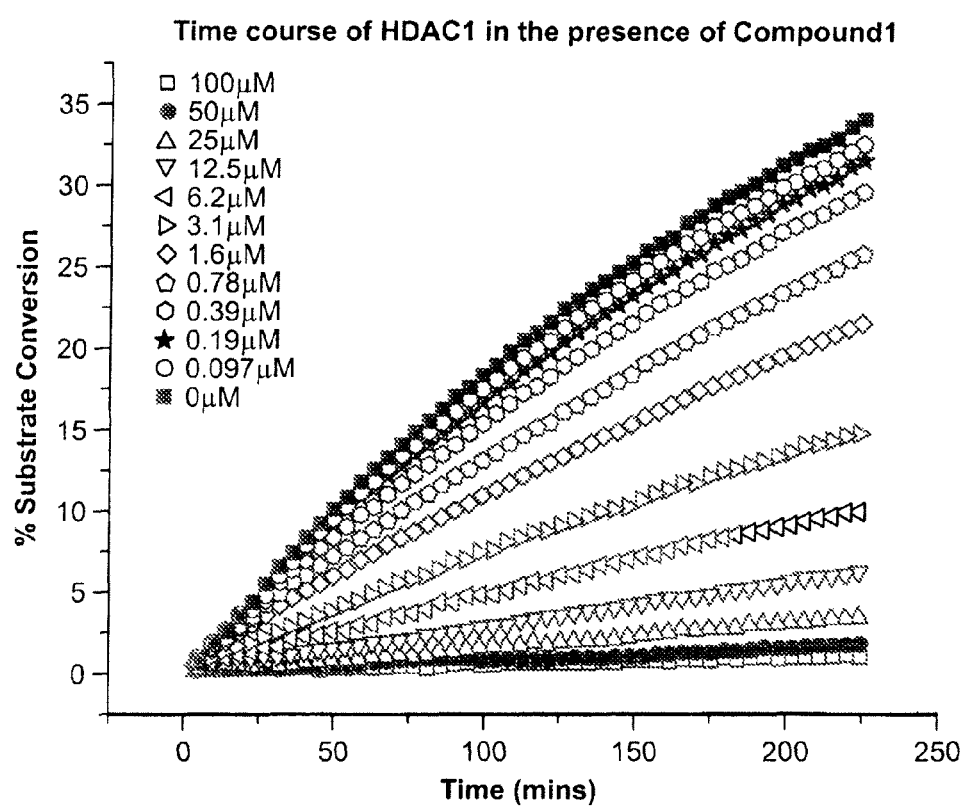
FIG. 2a is a graph which shows % substrate conversion over time for HDAC1 with compound 1 (Example 3).
Figure 2B:
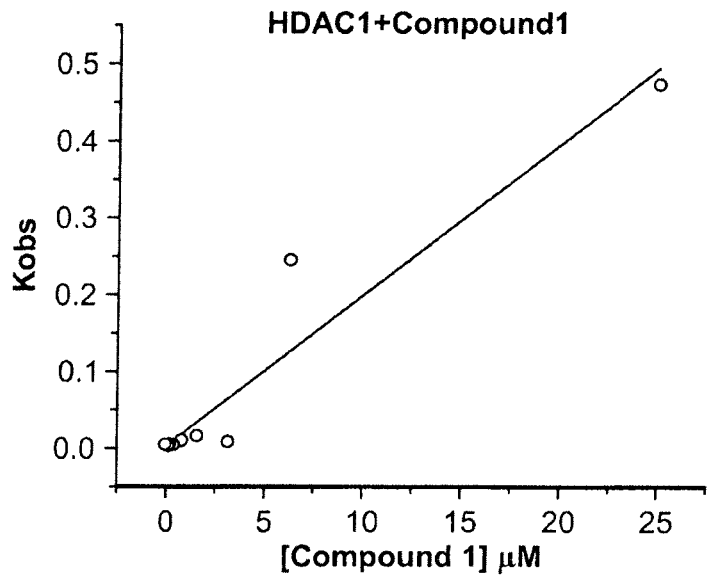
FIG. 2b is a graph which shows concentration of compound 1 vs. Kobserved for HDAC1 (Example 3).
Figure 2C:
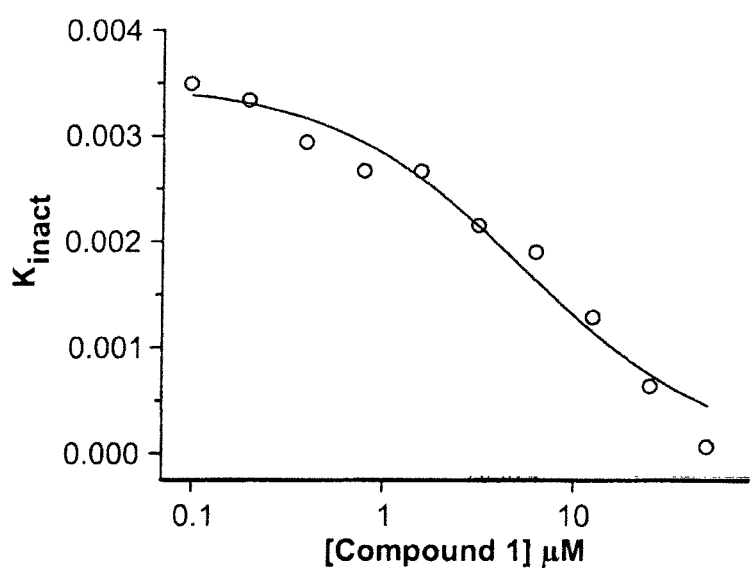
FIG. 2c is a graph which shows concentration of compound 1 vs. Kinactivation for HDAC1 (Example 3).
Figure 2D:
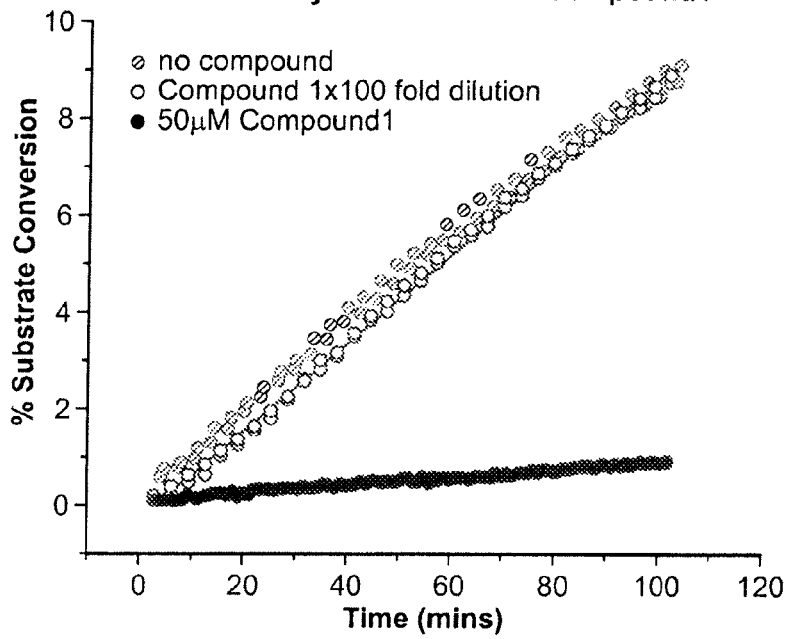
FIG. 2d is a graph which shows % substrate conversion over time in a reversibility assay for HDAC1 with compound 1 after 100-fold dilution (Example 3). The circles labeled "Compound 1×100 fold dilution" represent compound dilution.

The kinetics of the inhibition of HDAC1 by compound 1 were measured according to methods known in the art (See e.g., WO 2013/067391 entitled "Fluorescent Substrates for Determining Lysine Modifying Enzyme Activity"). Compound 1 was determined to be a fast off inhibitor for HDAC1. The binding constant of compound 1 to HDAC1 was also determined by monitoring the effect of inhibitor binding on inactivation kinetics (Na, Y R. & Park, C., (2009) Protein Science, 18, 268-276). HDAC1 deacetylation progression curve is approximately linear for two hours and there was a slight loss in linearity for longer incubation times. HDAC1 inactivation kinetic constant was determined by curve-fitting of the plot to a first-order rate equation. The determined Kinactivation values were inversely proportional to compound 1 concentration (FIG. 2c). The $K_d$ of HDAC1-Compound 1 complex was determined to be 5.1 µM, which is consistent with Ki values determined by inhibition kinetics (~14 uM). The results of this study are shown in FIGS. 2a, 2b, 2c, and 2d and the table below shows a summary of the kinetic parameters for compound 1 and HDAC1.

| Compound 1 | HDAC1 |
|---|---|
| Kon(min$^{-1}$, uM–1) | ~0.020 |
| Koff(min$^{-1}$) | ~0.27 |
| T$_{1/2}$(min) | ~2.5 |
| K$_i$ (uM) | 14 |

Example 4

Kinetics of the Inhibition of HDAC2

Figure 3A:
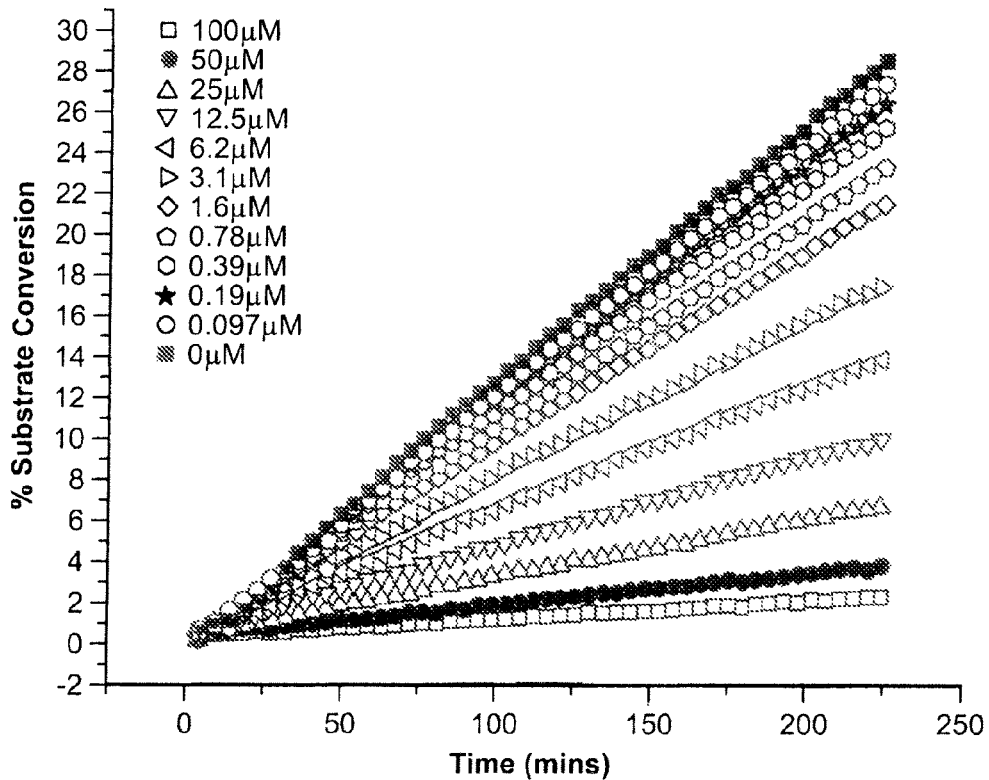
FIG. 3a is a graph which shows % substrate conversion over time for HDAC2 with compound 1 (Example 4).
Figure 3B:
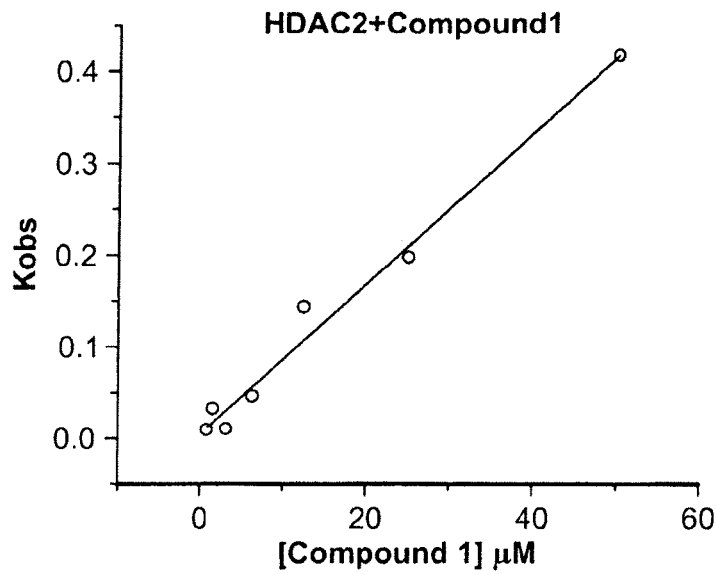
FIG. 3b is a graph which shows concentration of compound 1 vs. Kobserved for HDAC2 (Example 4).
Figure 3C:
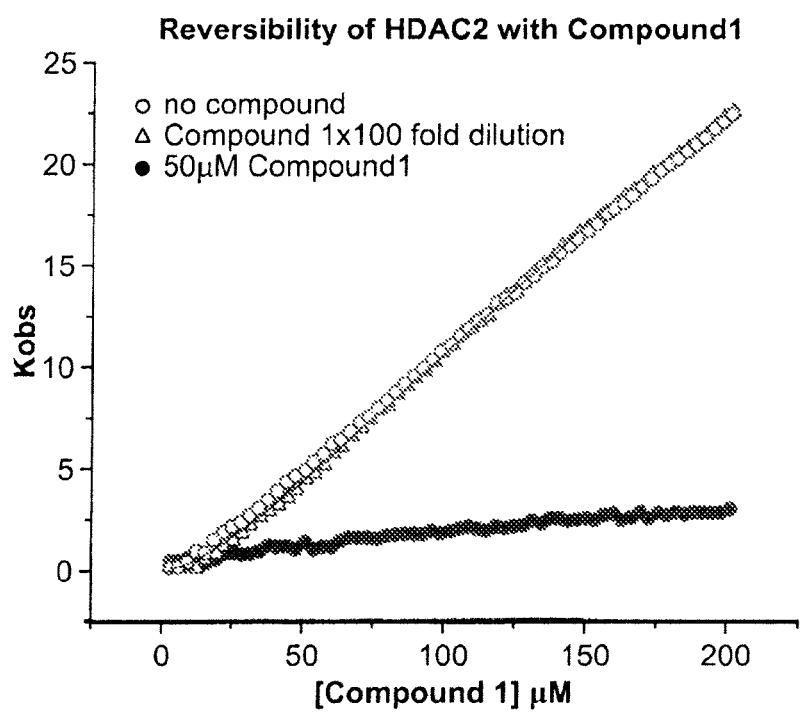
FIG. 3c is a graph which shows % substrate conversion over time in a reversibility assay for HDAC2 with compound 1 after 100-fold dilution (Example 4). The triangles labeled "Compound 1×100 fold dilution" represent compound dilution.

The kinetics of the inhibition of HDAC2 by compound 1 were measured according to methods known in the art (See e.g., WO 2013/067391 entitled "Fluorescent Substrates for Determining Lysine Modifying Enzyme Activity"). Compound 1 was determined to be a fast off inhibitor for HDAC2. The results of this study are shown in FIGS. 3a, 3b, and 3c and the table below shows a summary of the kinetic parameters for compound 1 and HDAC2.

| Compound 1 | HDAC2 |
|---|---|
| Kon(min$^{-1}$, uM$^{-1}$) | 0.0082 |
| Koff(min$^{-1}$) | 0.052 |
| T$_{1/2}$(min) | 13 |
| K$_i$ (uM) | 6.3 |

Example 5

Kinetics of the Inhibition of HDAC3

Figure 4A:
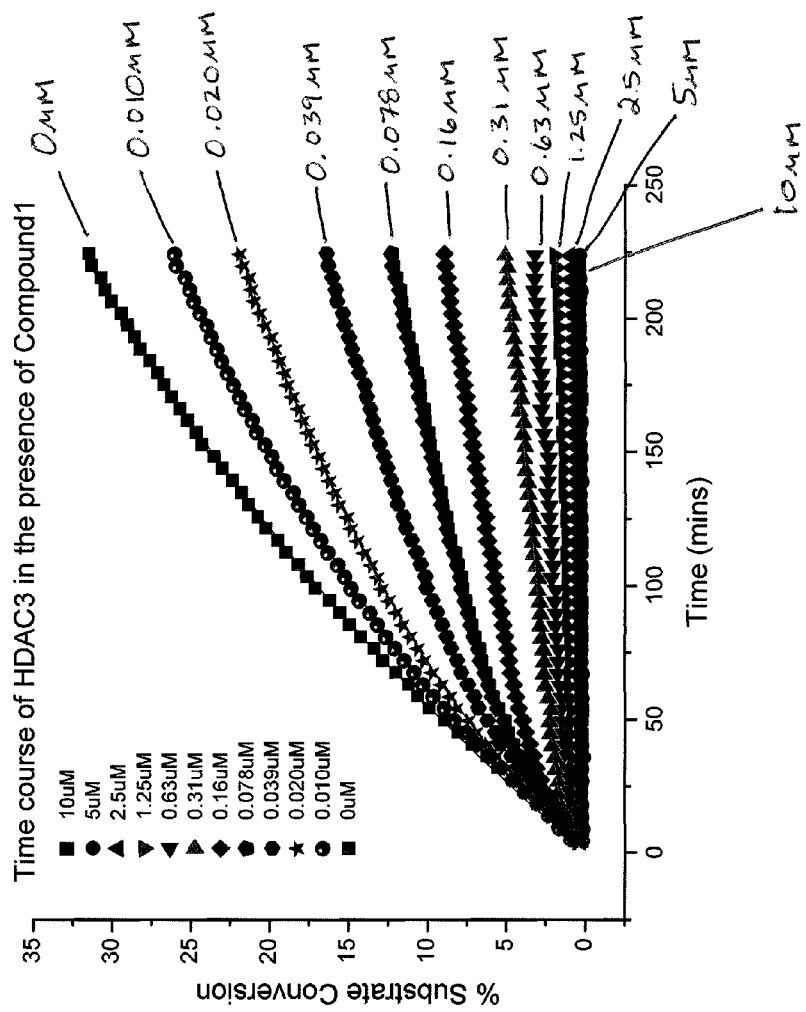
FIG. 4a is a graph which shows % substrate conversion over time for HDAC3 with compound 1 (Example 5).
Figure 4B:
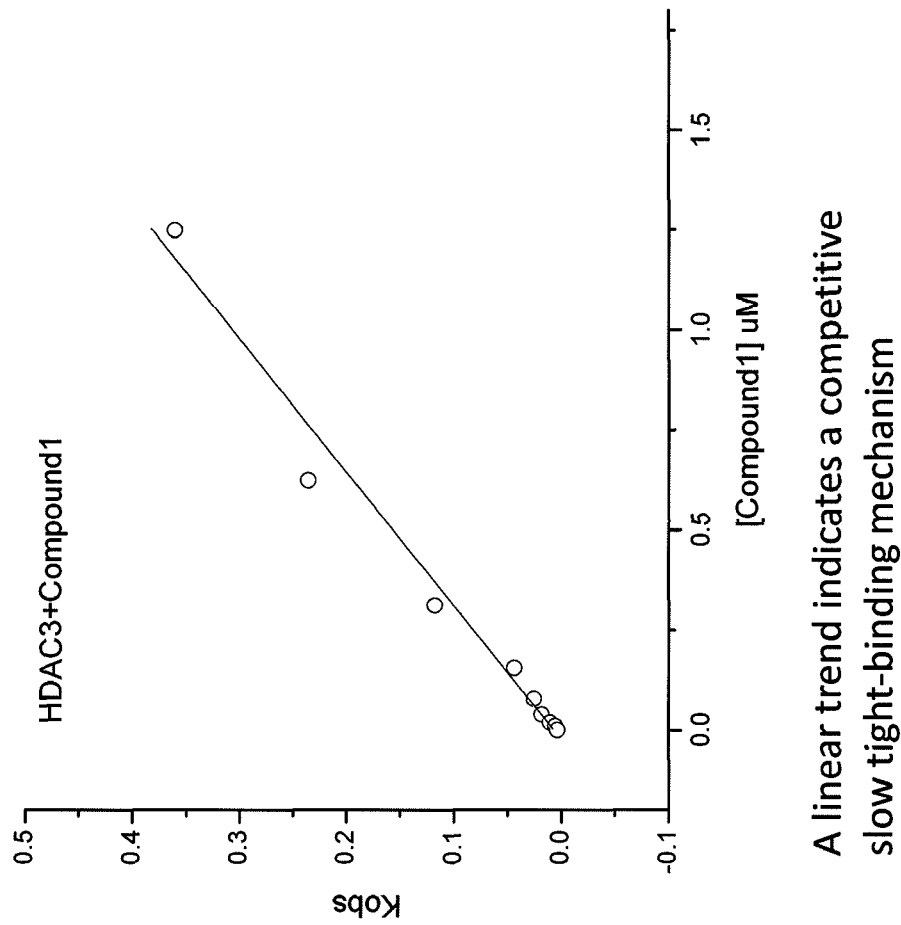
FIG. 4b is a graph which shows concentration of compound 1 vs. Kobserved for HDAC3 (Example 5).
Figure 4C:
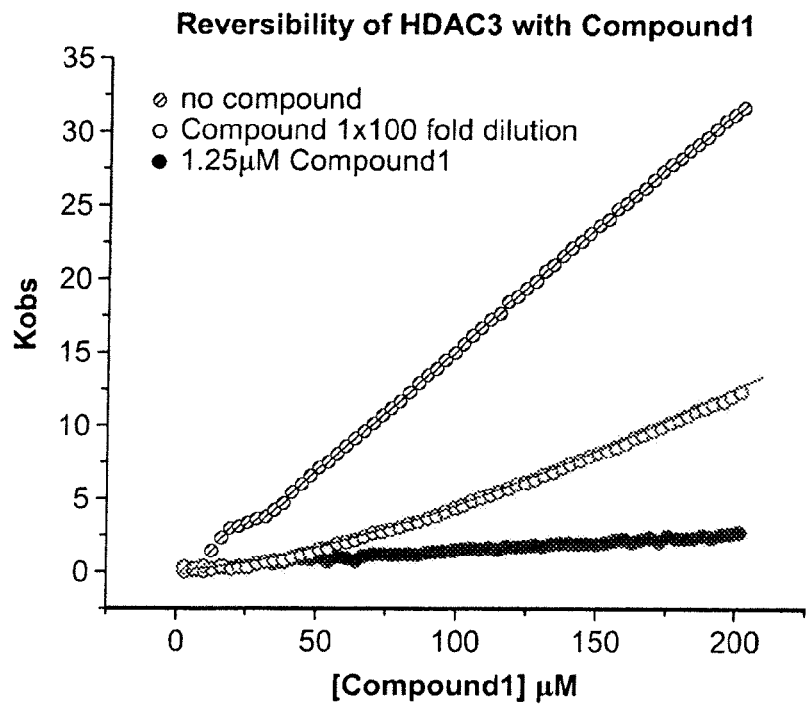
FIG. 4c is a graph which shows % substrate conversion over time in a reversibility assay for HDAC3 with compound 1 after 100-fold dilution (Example 5). The circles labeled "Compound 1×100 fold dilution" represent compound dilution.

The kinetics of the inhibition of HDAC3 by compound 1 were measured according to methods known in the art (See e.g., US patent Application 4143.3003 WO entitled "Fluorescent Substrates for Determining Lysine Modifying Enzyme Activity"). Compound 1 was determined to be a slow, tight-binding inhibitor for HDAC3. The results of this study are shown in FIGS. 4a, 4b, and 4c and the table below shows a summary of the kinetic parameters for compound 1 and HDAC3.

| Compound 1 | HDAC3 |
|---|---|
| Kon(min$^{-1}$, uM$^{-1}$) | 0.30 |
| Koff(min$^{-1}$) | 0.0088 |
| T$_{1/2}$(min) | 79 |
| K$_i$ (nM) | 29 |

A comparison summary of the thermodynamic and kinetic binding parameters for CI-994, compound 1, SAHA, MS-275, and compound 1A is shown in the table below. Compound 1A is a C-4 fluorinated derivative on the aniline ring of MS-275 representing a similar substitution pattern relationship as in CI-994 and Compound 1.

| | | Kinetic Parameters Summary | | | | |
|---|---|---|---|---|---|---|
| | | CI994 | Compound 1 | SAHA | MS-275 | Compound 1A |
| HDAC1 | Kon(min$^{-1}$, uM$^{-1}$) | 0.25 | ~0.020 | | 0.530 | 1.000 |
| | Koff(min$^{-1}$) | 0.0094 | ~0.27 | >0.2 | 0.0065 | >0.2 |
| | T$_{(1/2)}$ min | 74 | ~2.5 | <4 | 106 | <4 |
| | K$_i$(nM) | 37 | 5,100* | 1.9* | 12 | *160 |
| | IC$_{50}$(nM) @3 hr | 39 | 1,250 | 5 | 14 | 120 |
| HDAC2 | Kon(min$^{-1}$, uM$^{-1}$) | 0.016 | ~0.0082 | | 0.043 | 0.24 |
| | Koff(min$^{-1}$) | 0.0036 | 0.052 | >0.2 | 0.011 | 0.038 |
| | T$_{(1/2)}$ min | 190 | 13 | <4 | 63 | 17 |
| | K$_i$(nM) | 223 | ~6,300 | ~15 | 250 | 160 |
| | IC$_{50}$(nM) @3 hr | 110 | 1,420 | 16 | 41 | 157 |
| | Tm shift (° C.) | 8.8 | 2.7 | 9.9 | | |
| HDAC3 | Kon(min$^{-1}$, uM$^{-1}$) | 0.18 | 0.3 | | 0.110 | 0.093 |
| | Koff(min$^{-1}$) | 0.0044 | 0.0088 | >0.2 | 0.0013 | 0.0088 |
| | T$_{(1/2)}$ min | 160 | 79 | <4 | 530 | 79 |
| | K$_i$(nM) | 24 | 29 | 1.7 | 12 | 93 |
| | IC$_{50}$(nM) @3 hr | 38 | 68 | 4 | 34 | 36 |

(*binding constant derived from HDAC1 inactivation kinetics)

The results in the tables above show that substitution of a fluorine atom at the C-4 position of the aniline ring in CI-994 producing compound 1 imparts a unique and significant thermodynamic (Ki) and kinetic (on-off rates, $T_{1/2}$) binding selectivity for HDAC3 versus HDACs 1 and 2. Thermodynamically (Ki), compound 1 demonstrates 175-fold and 217-fold binding selectivity for HDAC3 versus HDAC1 and HDAC2 respectively. Kinetically (on-off rates, $T_{1/2}$) compound 1 demonstrates a unique fast on/slow off binding for HDAC3 in contrast to the slow on/fast off rates for HDAC1 and 2. These kinetic binding properties result in an extended residence time on HDAC3 ($T_{1/2}$=79 mins) compared to HDAC1 ($T_{1/2}$=2.5 mins) and HDAC2 ($T_{1/2}$=13 mins). Long residence times on a target are desirable and beneficial, particularly with respect to efficacy and toxicity. In addition, compound 1 retains potency for HDAC3 compared to the hydrogen C-4 derivative CI-994 (Ki=29 vs 24 nM).

A similar comparison between MS-275 and compound 1A (see Table 2A for structures) demonstrates that a similar fluorine substitution does not produce the same effects on binding to HDACs 1,2 and 3. Thermodynamically (Ki), compound 1A demonstrates a marginal 1.7 fold binding selectivity for HDAC3 versus HDAC1 and 2 respectively (100 fold less selective than compound 1). Kinetically (on-off rates, $T_{1/2}$) compound 1A retains relatively fast on binding rates for HDAC1,2 as compared to the hydrogen substituted MS-275. This is in contrast to the differential on rates displayed by compound 1 relative to CI-994 for HDACs 1 and 2 resulting in an increased selectivity in residence time of compound 1 for HDAC3 relative to compound 1A. In addition, compound 1A displays an 8 fold loss in potency for HDAC3 (Ki=12 vs 93 nM) compared to MS-275. A comparison of the results obtained by substituting a C-4 fluorine atom into the aniline ring of two known HDAC inhibitors demonstrates that a similar substitution pattern onto structurally distinct compounds does not produce the same effects on the kinetic and thermodynamic binding properties of the compounds to HDACs 1,2 and 3.

Example 6

Inhibition of Histone Deacetylase Enzymatic Activity

The following non-trypsin coupled in-vitro HDAC enzymatic endpoint assay was used to assay the compounds of the invention. Below is a standardized protocol for running HDAC selectivity panel on Caliper LabChip EZ-Reader Instrument.

The Caliper HDAC Assay Buffer (acronym HAB, 1 liter) was prepared as follows:

| Components: | Final Concentration: | Catalog #s: |
|---|---|---|
| 100 mL 1M KCL | 100 mM | Sigma #9541-500G |
| 50 mL 1M HEPES, pH 7.4 | 50 mM | Sigma #H3375-1KG |
| 1 mL 10% BSA | 0.01% | SeraCare #AP-4510-80-100G |
| 20 uL 50% Tween-20 | 0.001% | Zymed #00-3005-20mL |

The components were added to 1 liter Milli-Q water and store at 4° C.

The substrate (stock conc.) was prepared as follows: Substrate A was prepared as 2 mM in DMSO. Its final concentration in the assay for HDACs 1,2,3,6 is 2 µM. Substrate B was prepared as 2 mM in 100% DMSO. Its final concentration in the assay for HDACs 4,5,7,8,9 is 2 µM.

LBH was used as quench inhibitor to stop the reaction at the end point. The instrument buffer was ProfilerPro Separation Buffer (e.g., Caliper #760367). The instrument chip was LabChip EZ Reader II 12-Sipper Off-Chip Mobility Shift Chip (e.g., Caliper #760404).

Substrate A and B structures are shown below and prepared according to the synthetic procedure described in WO 2013/06739, entitled "Fluorescent Substrates for Determining Lysine Deacetylase Activity".

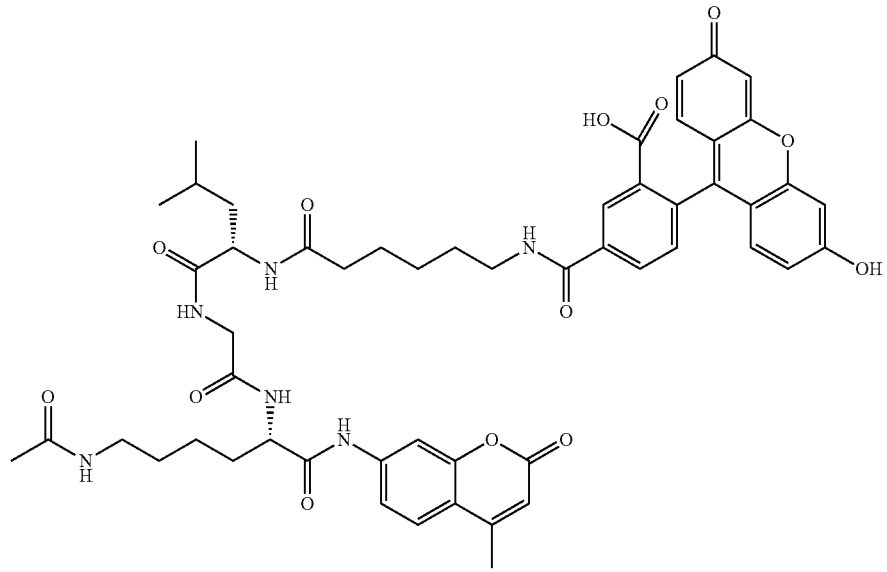

Substrate A

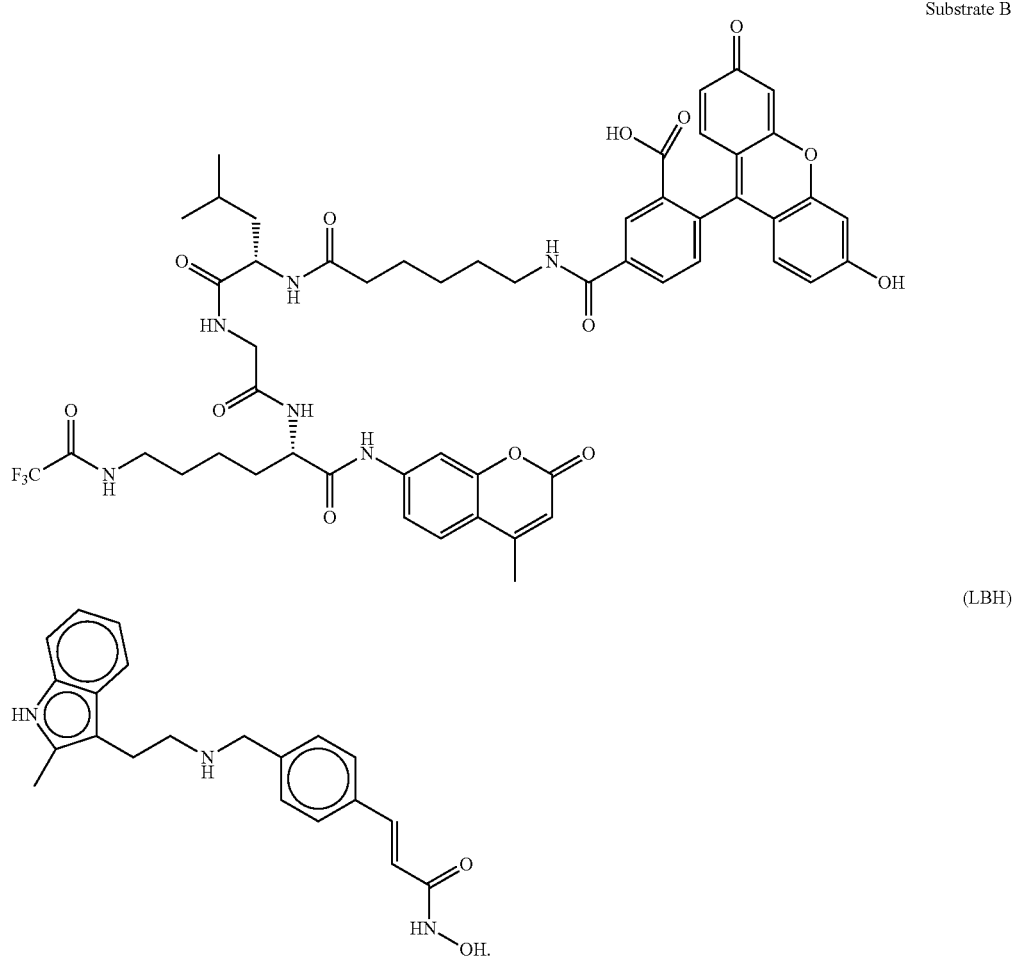

(LBH)

The protocol was carried out as follows:
1. Caliper LabChip and 1 µM Marker (peptide substrate in separation buffer) were prepared for instrument run.
2. Warm up Caliper HAB buffer to room temperature
3. Pin 100 nl compd. into 20 µl 1.5× solution HDACs and preincubate 3 hrs at room temperature
4. Add 10 µl 3× solution acetylated substrate to initiate the reaction for 50 minutes.
5. Stop reaction with 5 µL of 10 µM LBH solution (~1.4 uM final)
6. Mix plate
7. Read plate on EZ Reader instrument. Separate substrate and product peaks by capillary electrophoresis and read fluorescence from both substrate and product.
8. Run parameters were as follows:

| | Pressure | Upstream votage | Downstream votage | Post sample buffer sip time | Final delay | Peak order |
|---|---|---|---|---|---|---|
| Substrate A | −1.3 | −500 | −1500 | 35 | 90 | Product first |
| Substrate B | −1.3 | −500 | −1700 | 35 | 90 | Product first |

Below is the HDAC and Substrate concentration used in this assay.

| HDAC | BPS Cat. # | Substrate | Substrate Conc. (µM) | Stock enz. (µM) | Final enz. (nM) | Conversion % @1 hr |
|---|---|---|---|---|---|---|
| 1 | 50051 | Substrate A | 2 | 4.82 | 5 | 27% |
| 2 | 50002 | Substrate A | 2 | 44 | 3 | 20% |
| 3 | 50003 | Substrate A | 2 | 7.67 | 5 | 30% |
| 4 | 50004 | Substrate B | 2 | 26.6 | 0.5 | 38% |
| 5 | 50045 | Substrate B | 2 | 0.567 | 1 | 17% |
| 6 | 50006 | Substrate A | 2 | 5.66 | 2 | 29% |
| 7 | 50007 | Substrate B | 2 | 8.97 | 0.5 | 45% |
| 8 | 50008 | Substrate B | 2 | 12.93 | 0.5 | 22% |
| 9 | 50009 | Substrate B | 2 | 57.99 | 3 | 25% |

Preparation of Substrates A and B:
Scheme 1X
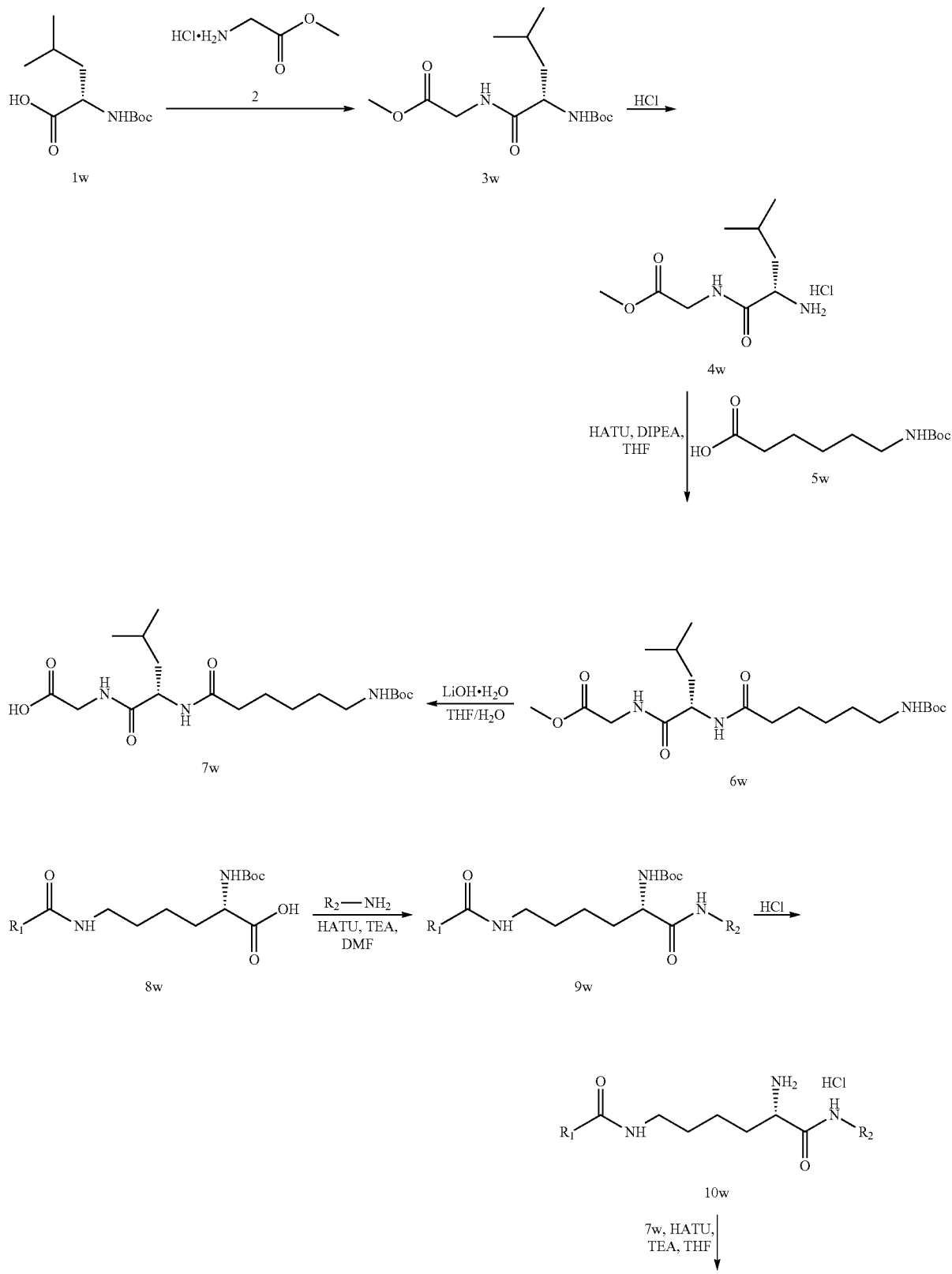

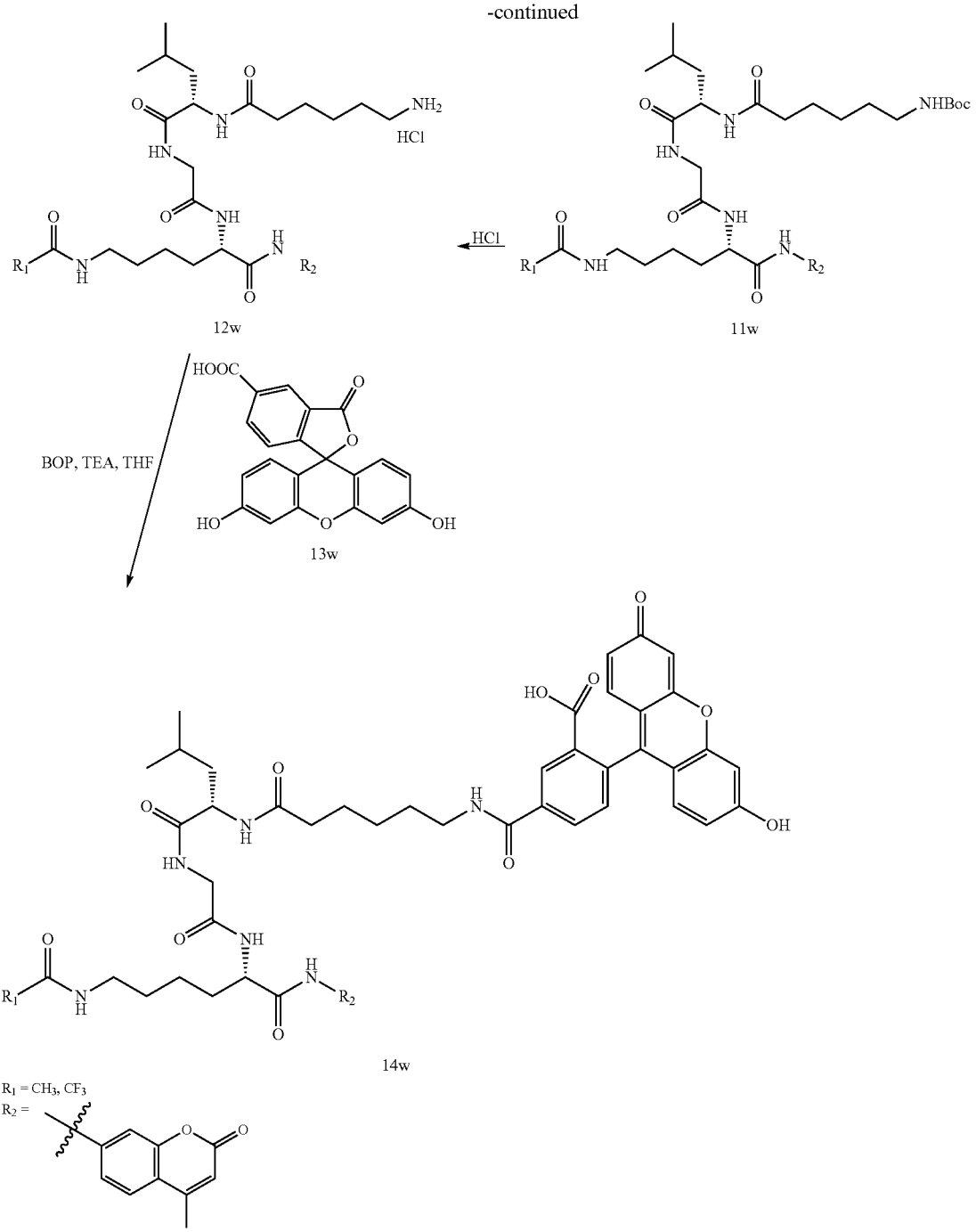

In one aspect, substrates A and B were prepared as follows. To a solution of (S)-2-((tert-butoxycarbonyl)amino)-4-methylpentanoic acid (1w) in THF was added methyl 2-aminoacetate hydrochloride (2w), Et$_3$N and HATU. The mixture was stirred at room temperature for 16 h. The reaction was filtered through Celite. The reaction filtrate was diluted with 100 mL of water and stirred for 15 min. The suspension was filtered off, rinsed with water and dried to afford (S)-methyl 2-(2-((tert-butoxycarbonyl)amino)-4-methylpentanamido)acetate (3w).

To a solution of (S)-methyl 2-(2-((tert-butoxycarbonyl)amino)-4-methylpentanamido) acetate (3w) in 1,4-dioxane was added a 5M solution of HCl in 1,4-dioxane at room temperature. The reaction was stirred at room temperature for 16 h. The reaction mixture was filtered to afford (S)-methyl 2-(2-amino-4-methylpentanamido)acetate hydrochloride (4w) as the filtered solid.

To a solution of (S)-methyl 2-(2-amino-4-methylpentanamido)acetate hydrochloride (4w) in THF was added 6-((tert-butoxycarbonyl)amino) hexanoic acid, HATU and DIPEA. The reaction was stirred at room temperature for 18 h. The mixture was then filtered through Celite. The filtrate was concentrated under reduced pressure and the crude residue was purified by column chromatography (silica gel, CH$_2$Cl$_2$/

MeOH=50/1) to give (S)-methyl 13-isobutyl-2,2-dimethyl-4,11,14-trioxo-3-oxa-5,12,15-triazaheptadecan-17-oate (6w) as a white solid.

To a solution of (S)-methyl 13-isobutyl-2,2-dimethyl-4,11,14-trioxo-3-oxa-5,12,15-triazaheptadecan-17-oate (6w) in THF was added a solution of LiOH.H$_2$O in water at room temperature. After 3 h, the reaction mixture was concentrated, diluted with water and acidified with a 1N aqueous solution of HCl to about pH 4-5. The mixture was stirred for 15 min and the white precipitate formed was filtered off, rinsed with water, and dried to afford (S)-13-isobutyl-2,2-dimethyl-4,11,14-trioxo-3-oxa-5,12,15-triazaheptadecan-17-oic acid (7w).

To a solution of 8w in DMF at room temperature was added 7-amino-4-methyl-2H-chromen-2-one, HATU and triethylamine. The reaction was stirred at room temperature for 2 h. A saturated solution of sodium bicarbonate was added. The product was extracted with ethyl acetate. The combined organic layers were washed with water, dried over sodium sulfate, filtered and concentrated under reduced pressure. The crude residue was purified by prep-HPLC to afford 9w.

To a solution of 9w in 1,4-dioxane was added a 5M solution of HCl in 1,4-dioxane. The reaction was stirred at room temperature for 3 h. The mixture was concentrated under reduced pressure to afford 10w.

To a solution of 10w in THF was added 7, HATU and triethylamine. The reaction was stirred at room temperature for 3 h. A saturated solution of sodium bicarbonate was added. The product was extracted with ethyl acetate. The combined organic layers were washed with water, dried over sodium sulfate, filtered and concentrated under reduced pressure. The crude material was purified by silica gel column (prep-HPLC) to afford 11w.

To a solution of 11w in 1,4-dioxane and was added a 5M solution of HCl in 1,4-dioxane. The reaction was stirred at room temperature for 3 h. The reaction was then concentrated and dried under reduced pressure to afford 12w.

To a solution of 12w in THF at room temperature was added 13w, BOP and triethylamine. The reaction was stirred at room temperature for 22 h. The mixture was then filtered through Celite. The filtrate was concentrated under reduced pressure. The crude residue was purified by prep-HPLC to give 14w.

The compounds of the invention were assayed for histone deacetylase inhibitory activity as described above. The data is presented in the tables below. IC50 values are in micromolar.

TABLE 2

| Compound Number | | Caliper Assay | | |
| --- | --- | --- | --- | --- |
| | | HDAC1 IC50 3 h Prein | HDAC2 IC50 3 h Prein | HDAC3 IC50 3 h Prein |
| 13 (CI-994) | [structure] | 0.039 | 0.11 | 0.038 |
| 1 | [structure] | 1.25 | 1.42 | 0.068 |
| 3 | [structure] | 2.18 | 4.93 | 0.551 |

TABLE 2-continued

| | HDAC Inhibition | | |
|---|---|---|---|
| | | Caliper Assay | | |
| Compound Number | | HDAC1 IC50 3 h Prein | HDAC2 IC50 3 h Prein | HDAC3 IC50 3 h Prein |
| 4 | *[structure: 4-acetamido-N-(2-amino-3-fluorophenyl)benzamide]* | 2.12 | 4.44 | 0.376 |
| 11 | *[structure: 4-acetamido-N-(2-amino-5-fluorophenyl)benzamide]* | 0.153 | 0.479 | 0.106 |
| 6 | *[structure: 4-acetamido-N-(2-amino-4-fluorophenyl)-2-fluorobenzamide]* | 1.38 | 3.12 | 0.080 |
| 7 | *[structure: N-(2-amino-4-fluorophenyl)benzamide]* | 7.95 | 12.7 | 0.418 |
| 8 | *[structure: N-(2-amino-4-fluorophenyl)-4-fluorobenzamide]* | 8.26 | 11.7 | 0.436 |

TABLE 2-continued

HDAC Inhibition

| Compound Number | Structure | Caliper Assay HDAC1 IC50 3 h Prein | HDAC2 IC50 3 h Prein | HDAC3 IC50 3 h Prein |
|---|---|---|---|---|
| 10 | 4-acetamido-N-(2-amino-4-(trifluoromethyl)phenyl)benzamide | >33 | >33 | >33 |
| 12 | 4-acetamido-N-(2-aminophenyl)-2-fluorobenzamide | 0.09 | 0.304 | 0.084 |
| 5 | 4-acetamido-N-(2-amino-5-bromophenyl)benzamide | 1.73 | 3.54 | 0.299 |
| 2 | 4-acetamido-N-(2-amino-4-chlorophenyl)benzamide | 4.56 | 24.4 | 2.05 |
| 9 | 4-acetamido-N-(2-amino-4-methylphenyl)benzamide | >33 | >33 | >33 |

The data presented above in Table 2 shows the unexpected effect that fluorination of the aniline ring of CI-994 has on HDAC isoform selectivity and potency. CI-994 is not selective for one particular isoform of HDAC1, HDAC2, or HDAC3. The results in Table 2 show that fluorination of the aniline ring produces an HDAC3 selective compound relative to HDACs 1 and 2 (see, for example Compounds 1, 3, 4, 6, 7 and 8). The addition of a fluorine atom to the aniline ring produces a more selective and more potent compound than the addition of other halogens or groups at the same position. For example, compare compound 1 to compound 2, 9, or 10. Table 2 also shows that the position of the fluorine atom on the aniline ring has an effect on the isoform selectivity of a compound. For example, compound 1 (4-fluorine) is unexpectedly more selective than compound 3 (6-fluorine), compound 4 (3-fluorine), and compound 11 (5-fluorine). Compound 1 is a 5-10 times more potent inhibitor of HDAC3 than the other fluorinated HDAC3 selective compounds e.g., compounds 3 and 4. This increased selectivity and potency of compound 1 for HDAC3 is unexpected. For example, there are reports in the literature which show that other fluorinated HDAC inhibitors do not possess significant HDAC3 selectively over their non-fluorinated counterparts (see, Rai, M., PLos ONE, vol. 5, January 2010, e8825).

Table 2 in combination with Tables 2B and 2C (shown below) shows the inhibitory activity of compound 1, CI-994, compound 9, SAHA, and BRD2492 versus HDACs 1,2,3, 4,5,6,7,8, and 9. The data confirms that compound 1 is an HDAC3 selective compound.

The effect of enhancing HDAC3 isoform selectivity by adding a fluorine atom is not generally applicable to other compounds having HDAC activity. Table 2A is a comparison of several different HDAC inhibitors and fluorinated versions thereof. The data in Table 2A shows that the substitution of a fluorine atom to the C-4 position of the aniline ring does not necessarily confer any or the same magnitude of HDAC3 isoform selectivity. For example, compare MS-275 (Entinostat), a known HDAC1,2,3 inhibitor, to its fluorinated derivative, compound 1A; compare MGCD-0103 (Mocetinostat), a known HDAC1,2,3 inhibitor, to its fluorinated derivative compound 2A. These data show that the fluorination of the known HDAC inhibitor does not necessarily produce an HDAC3 selective compound. The compound HUYA is a known HDAC1,2,3 inhibitor which contains a fluorine atom at the C-4 position. The HUYA compound is not HDAC3 selective and the data presented in Table 2A shows that the HUYA compound has a selectivity profile similar to its non-fluorinated derivative, Compound 3A.

TABLE 2A

| Name | Structure | HDAC1 IC50 ($\mu$M) 3 h Preinc | HDAC2 IC50 ($\mu$M) 3 h Preinc | HDAC3 IC50 ($\mu$M) 3 h Preinc |
|---|---|---|---|---|
| CI-994 | 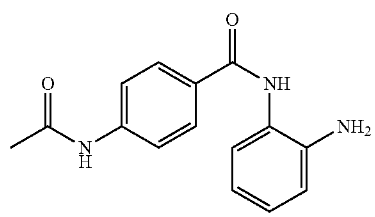 [SMILES: CC(=O)Nc1ccc(C(=O)Nc2ccccc2N)cc1] | 0.039 | 0.110 | 0.038 |
| Cmpd 1 | 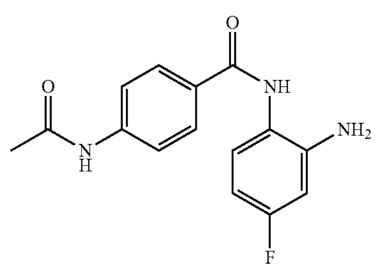 [SMILES: CC(=O)Nc1ccc(C(=O)Nc2ccc(F)cc2N)cc1] | 1.25 | 1.42 | 0.068 |
| MS-275 | 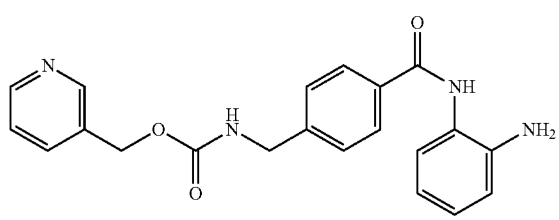 [SMILES: Nc1ccccc1NC(=O)c1ccc(CNC(=O)OCc2cccnc2)cc1] | 0.014 | 0.041 | 0.034 |
| Cmpd 1A | 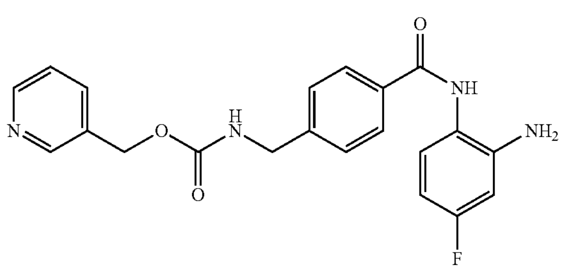 [SMILES: Nc1cc(F)ccc1NC(=O)c1ccc(CNC(=O)OCc2cccnc2)cc1] | 0.120 | 0.157 | 0.036 |

TABLE 2A-continued

| Name | Structure | HDAC1 IC50 (μM) 3 h Preinc | HDAC2 IC50 (μM) 3 h Preinc | HDAC3 IC50 (μM) 3 h Preinc |
|---|---|---|---|---|
| MGCD-0103 | 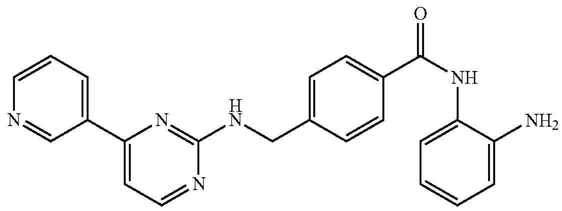 [SMILES: Nc1ccccc1NC(=O)c1ccc(CNc2nccc(-c3cccnc3)n2)cc1] | 0.006 | 0.026 | 0.023 |
| Cmpd 2A | 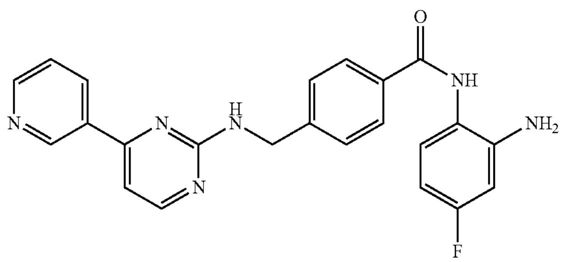 [SMILES: Nc1cc(F)ccc1NC(=O)c1ccc(CNc2nccc(-c3cccnc3)n2)cc1] | 0.012 | 0.018 | 0.017 |
| Cmpd 3A | 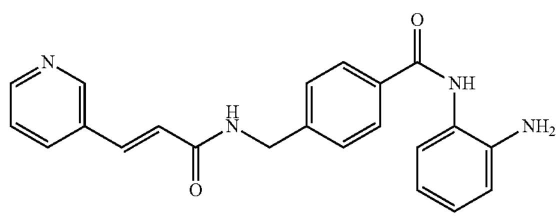 [SMILES: Nc1ccccc1NC(=O)c1ccc(CNC(=O)/C=C/c2cccnc2)cc1] | 0.004 | 0.023 | 0.022 |
| HUYA | 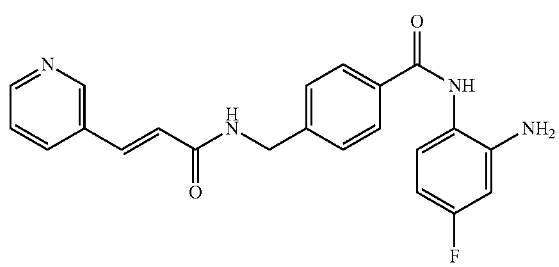 [SMILES: Nc1cc(F)ccc1NC(=O)c1ccc(CNC(=O)/C=C/c2cccnc2)cc1] | 0.009 | 0.049 | 0.022 |

TABLE 2B

| | Selectivity Profile | HDAC1 IC50 (μM) after 3 hr preincubation | HDAC2 IC50 (μM) after 3 hr preincubation | HDAC3 IC50 (μM) after 3 hr preincubation |
|---|---|---|---|---|
| SAHA | 1, 2, 3, 6 | 0.005 | 0.016 | 0.004 |
| BRD2492 | 1, 2 | 0.002 | 0.019 | 2.08 |

TABLE 2C

| | HDAC4 IC50 (μM) after 0 hr preincubation | HDAC5 IC50 (μM) after 0 hr preincubation | HDAC6 IC50 (μM) after 0 hr preincubation | HDAC7 IC50 (μM) after 0 hr preincubation | HDAC8 IC50 (μM) after 0 hr preincubation | HDAC9 IC50 (μM) after 0 hr preincubation |
|---|---|---|---|---|---|---|
| compound 1 | >33 | >33 | >33 | >33 | >33 | >33 |
| CI-994 | >33 | >33 | >33 | >33 | >33 | >33 |
| compound 9 | >33 | >33 | >33 | >33 | >33 | >33 |
| SAHA | >33 | 8.75 | 0.002 | >33 | 1.02 | >33 |
| BRD2492 | >33 | >33 | >33 | >33 | >33 | >33 |

Example 7

Compounds of the invention were evaluated for their ability to influence dopaminerigic signaling according to the following procedure. Mice were dosed once daily with 10 mg/kg of compound 1. Data collected 18-24 h after the 7th dose. Amphetamine-induced hyperactivity (AIH) was examined in eight identical open-field chambers (16.5"×16"×12"; AccuScan Instruments, Columbus, Ohio). Activity was detected by infrared beam breaks and recorded automatically by VersaMax software (AccuScan). Daily sessions were automatically binned in 5 minute intervals (VersaDat; AccuSacn) for statistical analysis. AIH was run over three consecutive days as follows:

Day 1: Habituation: Mice were placed into the open-field for 20 minutes and then removed for a saline injection. Mice were placed back into the open-field for an additional 30 minutes, at which point the mice were returned to their home cage.

Day 2: Baseline Motor Activity: This phase was run identically to Day 1, with the exception that the second day lasted for one hour (20 minutes pre-injection; 40 minutes post-injection).

Day 3: Amphetamine Challenge: Mice were placed in the open-field. After 20 minutes, mice were removed and challenged with amphetamine, and placed back in the open-field for 80 minutes.

Note: All HDAC inhibitor treatments occurred 18-25 hours prior to behavioral testing. Thus, all behavioral data are collected without the potential for confounding effects of the compound itself. FIGS. 5 and 6 show the results of this study.

Example 8

Compounds of the invention were evaluated for their ability to suppress cytokine-induced beta-cell apoptosis and palmitate and/or glucose-induced beta-cell apoptosis by inhibition of HDAC3. Assay protocols were as follows: Cell culture and reagents. INS-1E cells (provided by Claes Wollheim and Pierre Maechler, University of Geneva, Switzerland) were maintained in culture medium (RPMI 1640 containing 11 mM glucose, 10% fetal bovine serum, 10 mM HEPES, 50 μM 2-mercaptoethanol, 1 mM sodium pyruvate) and cultivated at 37 C with 5% $CO_2$ in a humidified atmosphere. Recombinant IL-1β, IFN-γ, and TNF-α were purchased from R&D Systems. Palmitate, D-glucose and fatty acids-free low endotoxin BSA were purchased from Sigma. Palmitate was solubilized in 90% ethanol, heated to 60° C. and used 1:100 dilution in media. Caspase-Glo 3/7 was from Promega and 3-(4,5-dimethylthiazol-2-yl)-2,5-diphenyltetrazolium bromide (MTT) was from Calbiochem. Antibodies for HDAC1, HDAC2, HDAC3, pJNK, JNK cleaved caspase-9 and secondary horseradish-peroxidase conjugated goat anti-mouse and anti-rabbit antibodies were from Cell Signaling. Antibody for beta-actin was from Sigma and antibody against CHOP (GADD153) from Abcam. HDAC inhibitors were purchased from Selleck Chemicals or synthesized in-house. Primers were from Integrated DNA Technologies, High Capacity cDNA RT kit and SYBR green master mix were purchased from Applied Biosystems.

Rat islets. Primary neonatal rat islets were isolated from outbred 3 to 6 days old Wistar rats (Taconic) and cultured in RPMI 1640 with 20 mmol/l HEPES buffer, 2 mmol/l L-glutamine, 0.038%, $NaHCO_3$, 100 U/ml penicillin and 100 g/ml streptomycin supplemented with 1% FBS.

Human islets. Human islets were provided by the Integrated Islet Distribution Program administered by the City of Hope Hospital (IIDP:http://iidp.coh.org/). The average reported purity was 85%±5.2 and viability was 94%+0.6 (age 50±5 years, body mass index 31±2.7 kg/m2). Causes of death were head trauma (n=3), stroke and anoxia. Islets were dissociated and seeded (30,000 cells/well) into black optical 96-well plates (Corning Life Sciences) that coated with HTB-9 extracellular matrix as previously described. (Walpita, D., et al. (2012) J. Biomol. Screen. 17, 509-518.) The dissociated islet cell cultures were allowed to attach and grow in CMRL media in 10% FBS for 3 days before exposure to palmitate (0.5 mM) and high glucose (25 mM) in medium with 1% BSA and without FBS for 72 hours.

Caspase-3 activity assay. INS-1E cells were seeded at 5,000 cells/well using a Multidrop Combi (Thermo Labsystems) in white optical 384-well plates (Corning Life Sciences). After overnight incubation, medium was removed and 50 μL RPMI containing the treated compound, 1% FBS and either a combination of cytokines (10 ng/mL IL-1β, 50 ng/mL IFN-γ, 25 ng/mL TNF-α) or 0.5 mM sodium palmitate was added to every well. After two-day treatment, medium was removed and 20 μL Caspase-Glo 3/7 reagent was added. Luminescence was measured after a two-hour incubation using an Envision plate reader (PerkinElmer).

Cell death detection by ELISA. Rat islets (50 islets/well) were cultured in 48-well plates (NUNC) and exposed to palmitate (0.5 mM) and glucose (25 mM) in medium supplemented with 1% FBS and 1% BSA for 60 hours. Cell death was determined in biological duplicates using a cell death ELISA assay (Roche).

Cell viability. INS-1E cells (10,000 cells/well) were seeded in white optical 384-well with 50 uL complete medium. After overnight incubation medium was removed, and cells were exposed to 50 uL medium/well with the indicated concentrations of palmitate, glucose, HDAC inhibitors and/or vehicle. After 48 hours, medium was removed and the proportion of metabolically active cells determined using the MTT assay. Each condition was assayed in 6-14 biological replicates.

Real-time PCR. INS-1E cells (one million/well) were seeded in 6-well plates in 2 mL complete medium. After two days, medium was removed and cells were exposed to 2 mL medium/well with the indicated concentrations of palmitate, glucose, HDAC inhibitors and/or vehicle. RNA was purified (Qiagen) and cDNA synthesis performed done according to manufacturers' guidelines (Applied Biosystems) and real-time PCR performed using the SYBR green method (Applied Biosystems). Each cDNA sample in triplicate was subjected to two individual PCR amplifications either for the gene of interest or the reference gene β-actin. See table below for primer sequences.

| Target | Forward | Reverse |
|---|---|---|
| β-actin | CACCCGCGAGTACAACCTTC (SEQ ID No. 1) | CCCATACCCACCATCACACC (SEQ ID No. 10) |
| Chop | CAGCGACAGAGCCAAAATAAC (SEQ ID No. 2) | TGTGGTGGTGTATGAAGATGC (SEQ ID No. 11) |
| Atf3 | GGAGTCAGTCACCATCAACAA (SEQ ID No. 3) | CGCCTCCTTTTTCTCTCATCT (SEQ ID No. 12) |
| Bip | CGTATTTGGGAAAGAAGGTCA (SEQ ID No. 4) | CTTCTCTCCCTCTCTCTTATCCA (SEQ ID No. 13) |
| Ins1 | GTCCTCTGGGAGCCCAAG (SEQ ID No. 5) | ACAGAGCCTCCACCAGG (SEQ ID No. 14) |
| Ins2 | ATCCTCTGGGAGCCCCGC (SEQ ID No. 6) | AGAGAGCTTCCACCAAG (SEQ ID No. 15) |
| ATtf4 | GTTGGTCAGTGCCTCAGACA (SEQ ID No. 7) | CATTCGAAACAGAGCATCGA (SEQ ID No. 16) |

-continued

| Target | Forward | Reverse |
|---|---|---|
| Xbp1s | GAGTCCGCAGCAGGTG (SEQ ID No. 8) | GCGTCAGAATCCATGGGA (SEQ ID No. 17) |
| IκBα | TCCTCAACTTCCAGAACAACC (SEQ ID No. 9) | GCAAGATGGAGAGGGGTATTT (SEQ ID No. 18) |

Immunoblotting. INS-1E cells (one million/well) were seeded in 6-well plates in 2 mL complete medium. After two days, medium was removed and cells were exposed to 2 mL medium/well with the indicated concentrations of palmitate, glucose, test compounds and/or vehicle. Cells were lysed using Passive Lysis Buffer (Promega) containing protease inhibitors (Roche). Lysates were adjusted for protein concentration (Bradford) and protein separated by SDS-PAGE and transferred to PVDF membranes. Blots were developed using a chemiluminescence detection system (SuperSignal, Thermo Fisher Scientific), and light emission was captured using an Imaging Station 4000MM (Carestream).

Insulin assay. INS-1E cells (20,000 cells/well) were seeded in 96-well plates in 100 uL complete medium. After overnight incubation media was removed and cells were exposed to 100 uL medium/well with the indicated concentrations of palmitate, glucose, HDAC inhibitors and/or vehicle. After 48 hours, medium was removed and cells were incubated for 2 hours in KRBH buffer (135 mM NaCl, 3.6 mM KCl, 5 mM NaHCO$_3$, 0.5 mM NaH$_2$PO$_4$, 0.5 mM MgCl$_2$, 1.5 mM CaCl$_2$, 10 mM HEPES [pH 7.4], and 0.1% BSA) lacking glucose. Cells were subsequently incubated with KRBH buffer containing 2 mM or 16 mM glucose for 1 hour. Supernatants were collected for measurement of insulin. For measuring insulin content, cells were washed in PBS and lysed using Passive Lysis Buffer. Insulin was measured with a rat insulin ELISA kit (Alpco). Total insulin content was normalized to total protein (Bradford assay). Each condition was assayed in biological duplicates.

ROS formation. INS-1E cells (50,000 cells/well) were seeded in 96-well plates in 100 uL complete medium. Two days after incubation, medium was removed and cells exposed to 100 uL medium/well with the indicated concentrations of palmitate, glucose, test compounds and/or vehicle. After 24 hours, cells were aspirated and incubated for 45 min in phenol redfree RPMI (Invitrogen) containing 10 μM CM-H2DCFDA probe (Molecular Probes). Wells were subsequently washed twice with phenol red-free RMPI, incubated for 3 min with Hoechst 33342 (10 ug/mL) in phenol red-free media, followed by a final washing step. Fluorescence was captured by an IX Micro automated fluorescence microscope (Molecular Devices) and quantification of ROS per cell was analyzed using MetaXpress software (Molecular Devices). Each condition was assayed in five biological replicates.

RNA interference. Small-interfering RNAs against HDAC1, HDAC2 and HDAC3 were from Dhamarcon (Thermo Scientific). siRNAs (final concentration of 25 nM) were transfected into INS-1E cells (5.000/well for caspase-3 activity, 1*106/well for immunoblotting) for 8 hours using DharmaFECT reagent (Thermo Scientific). Transfected cultures were cultured for 48 hours before assayed.

Figure 7:
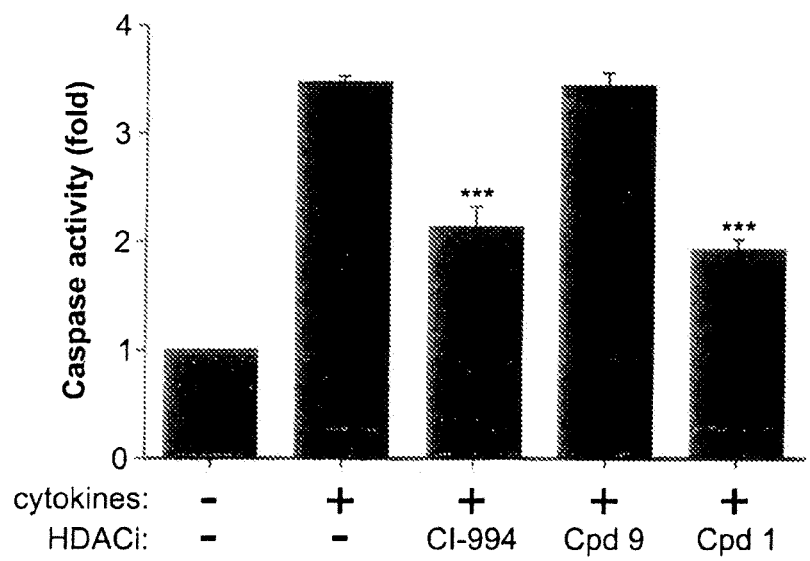
FIG. 7 is a bar graph which shows the suppression of cytokine-induced beta-cell apoptosis by inhibition of HDAC3 with compound 1 and CI-994 compared to a negative control compound 9 as determined by changes in caspase activity (Example 8).

FIG. 7 shows the suppression of cytokine-induced beta-cell apoptosis by inhibition of HDAC3 by compound 1 as determined by changes in caspase activity. The rat INS-1E cell line was simultaneously treated for 48 hours with a combination of pro-inflammatory cytokines IL-1β, IFN-γ, and TNF-α, and the indicated test compounds.

The concentration of test compound used was 5 μM. FIG. 7 show that compound 1, a selective HDAC3 inhibitor, is as effective at suppressing cyctokine-induced beta-cell apoptosis as CI-994, a HDAC1,2,3 inhibitor. Compound 9, a negative control, had no effect. These results show that HDAC3 inhibition is important and sufficient to provide equal efficacy at repressing cytokine-induced beta-cell apoptosis. These results also show that inhibition of HDAC1,2 is not necessary and does not increase efficacy at repressing cytokine-induced beta-cell apoptosis. FIGS. 9C and 9D show a dose-response analysis of HDAC inhibition in suppression of cytokine-induced beta-cell apoptosis. These results show that a selective HDAC3 inhibitor is still efficacious at higher doses while a HDAC1,2,3 inhibitor show signs of toxicity at higher concentrations (see e.g., Example 10). This could translate to a larger therapeutic window.

Figure 17:
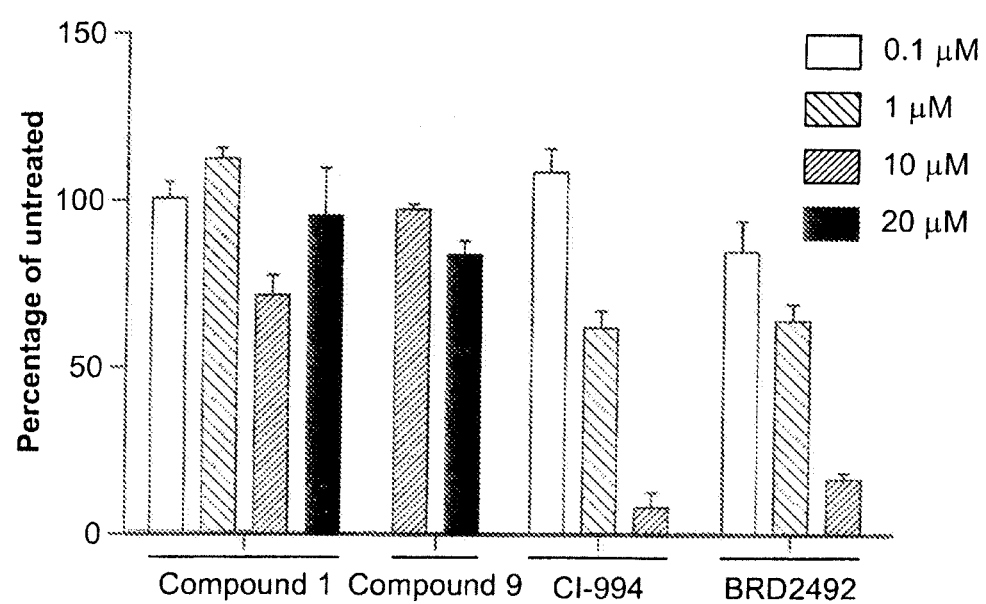
FIG. 17 is a bar graph, which shows the effect of increasing concentrations of compound 1 (an HDAC3 selective inhibitor), compound 9 (negative control), CI-994 (an HDAC1,2,3 inhibitor) and BRD2492 (an HDAC1,2 inhibitor) on the growth and viability of human megkaryocyte progenitor cells relative to DMSO treated cells (% untreated). The results with respect to compound 1 and compound 9 are desirable. Specifically, the compounds have no significant effect on growth and viability relative to DMSO treated cells.
Figure 18:
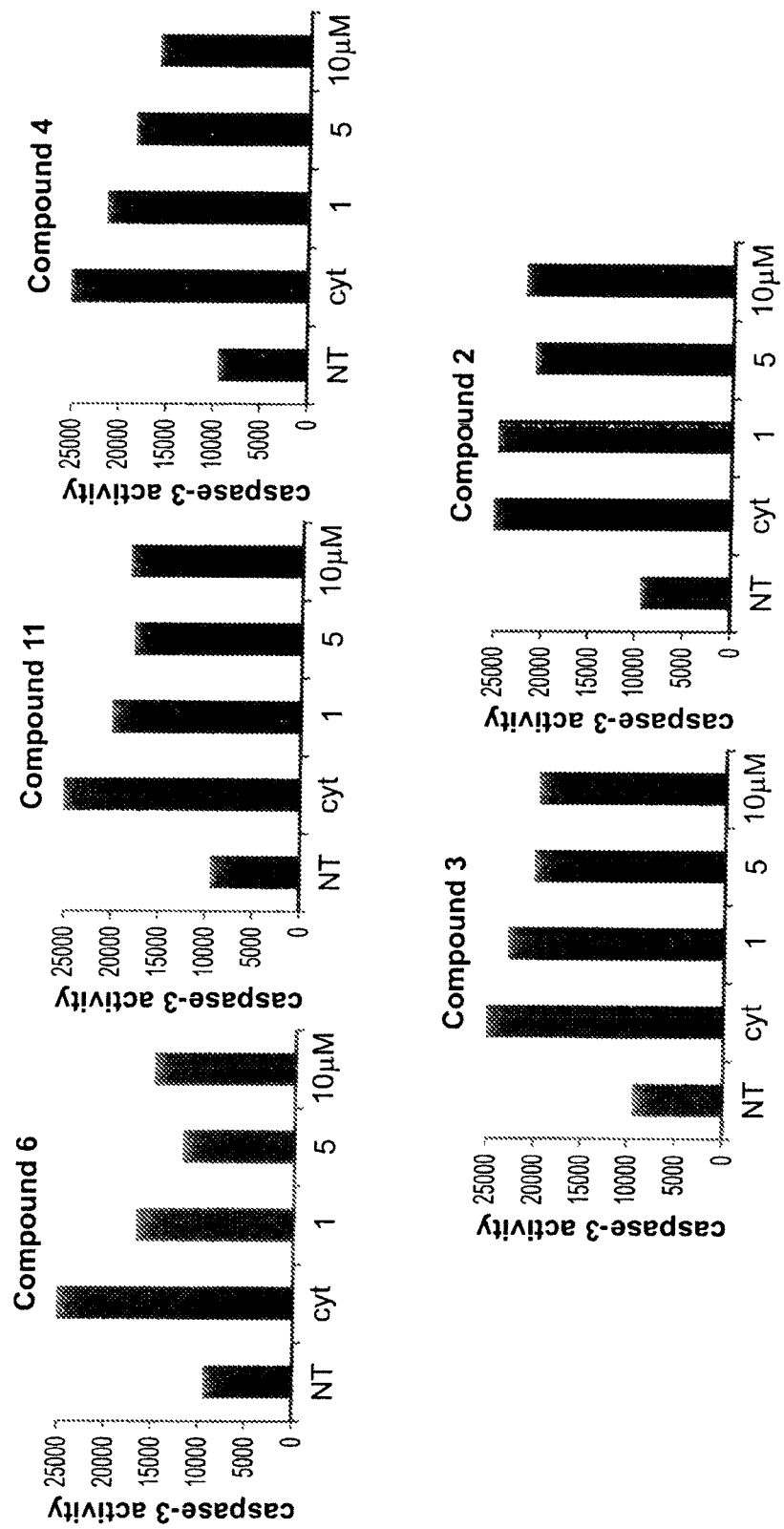
FIG. 18 is a series of bar graphs, which show the effect of different compounds of the invention in suppression of cytokine-induced beta-cell apoptosis in INS-1E cells as measured by effects on caspase activity.

FIGS. 17-18 show the effect of different compounds on the suppression of caspase-3 activity in cells. Specifically, the figures show the superior effect of compound 1 on suppressing caspase-3 activity in a dose dependent manner in comparison to other fluorinated and chlorinated derivatives (compounds 6, 11, 4, 2 and 2). The results show that the compound 1, which contains a C-4 substituted fluorine atom on the aniline ring, is more effective at suppressing caspase-3 activity than compounds containing a fluorine atom at other positions on the aniline ring and a compound containing a different halogen atom at the C-4 position. FIG. 17 shows the effect of CI-994 and compound 1 in suppressing caspase-3 activity in cells. The cells are treated with 0.1 μM, 1 μM, 5 μM and 10 μM of compound. FIG. 18 shows the effect of Compounds 6, 11, 4, 3, and 2 on suppressing caspase-3 activity. The cells are treated with 1 μM, 5 μM and 10 μM of compound. Weaker HDAC3 inhibitors are not as effective at suppressing caspase-3 activity.

Figure 8:
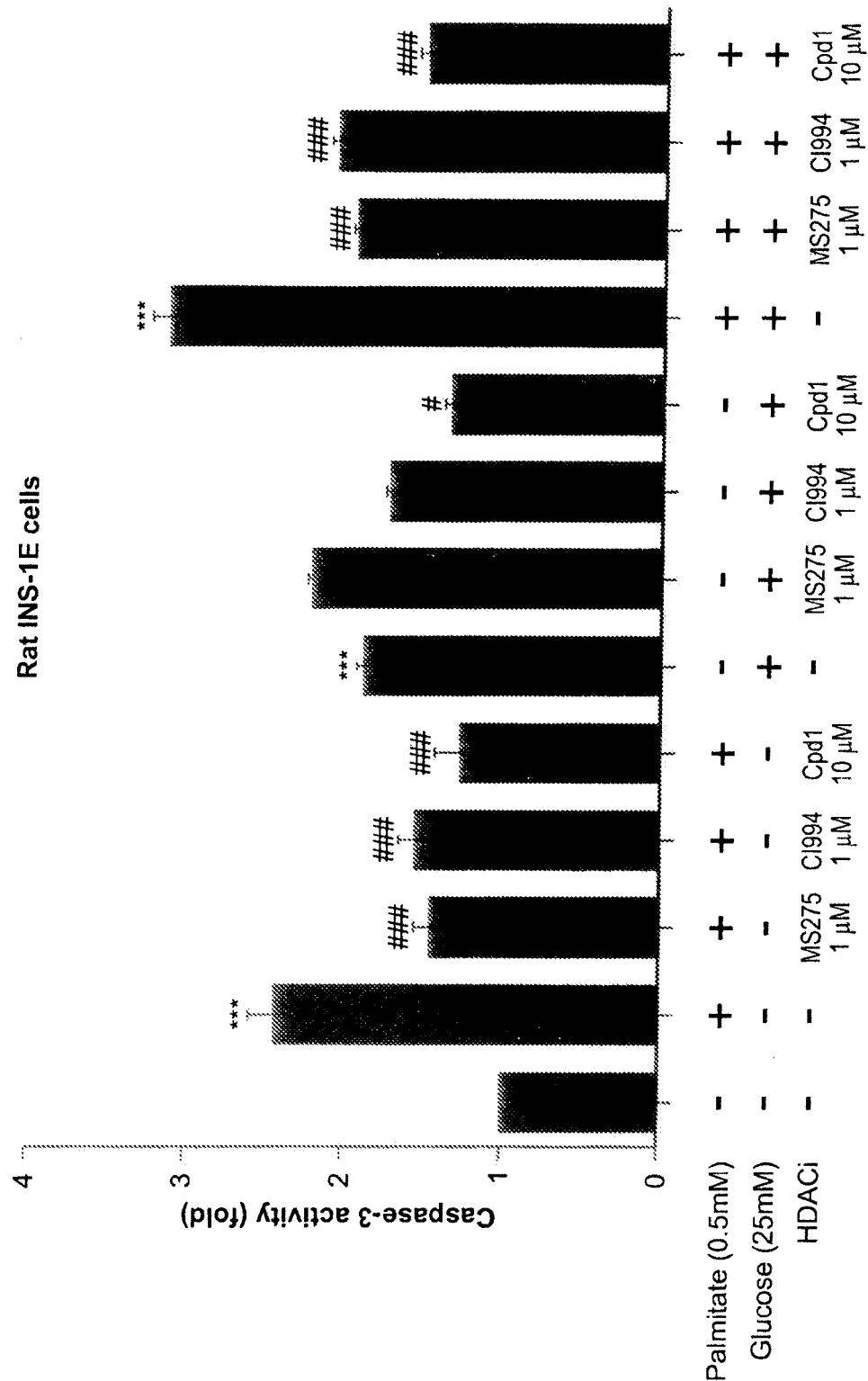
FIG. 8 is a bar graph which shows the suppression of palmitate/glucose-induced beta-cell apoptosis by inhibition of HDAC3 with compound 1, MS-275 and CI-994 as determined by changes in caspase activity.

FIG. 8 shows the suppression of palmitate and/or glucose-induced beta-cell apoptosis by inhibition of HDAC3 by compound 1 as determined by changes in caspase activity. The rat INS-1E cell line was simultaneously treated for 48 hours with a 0.5 mM palmitate, 25 nM glucose, or a combination of 0.5 mM palmitate and 25 mM glucose and the indicated test compounds. Apoptosis was measured by caspase-3/7 activation using a commercially available kit. FIG. 8 shows that compound 1, a selective HDAC3 inhibitor, is as effective at suppressing palmitate and/or glucose-induced beta-cell apoptosis as CI-994, a HDAC1,2,3 inhibitor and MS-275, HDAC1,2,3 inhibitor. These results show that HDAC3 inhibition is important and sufficient to provide equal efficacy at repressing palmitate and/or glucose-induced beta-cell apoptosis. These results also show that inhibition of HDAC1,2 is not necessary and does not increase efficacy at repressing palmitate and/or glucose-induced beta-cell apoptosis. FIGS. 9A and 9B show a dose-response analysis of HDAC inhibition in suppression of palmitate-induced beta-cell apoptosis. These results show that a selective HDAC3 inhibitor is still efficacious at higher doses while HDAC1,2,3 inhibitors show signs of toxicity at higher concentrations (see, e.g., Example 10). This could translate to a larger therapeutic window.

Figure 10A:
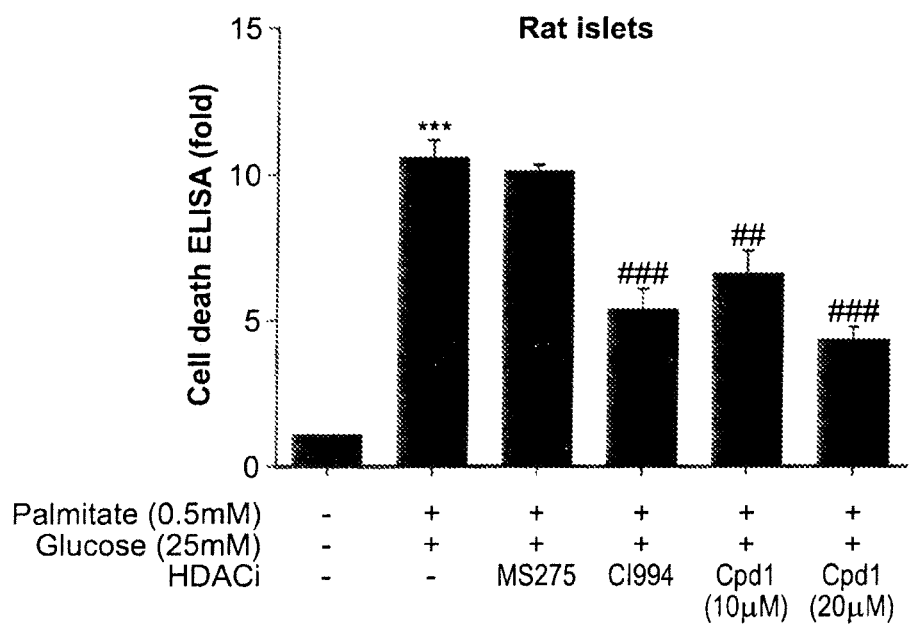
FIG. 10A shows that compound 1 decreases glucolipotoxicity-induced apoptosis in rat islets.
Figure 10B:
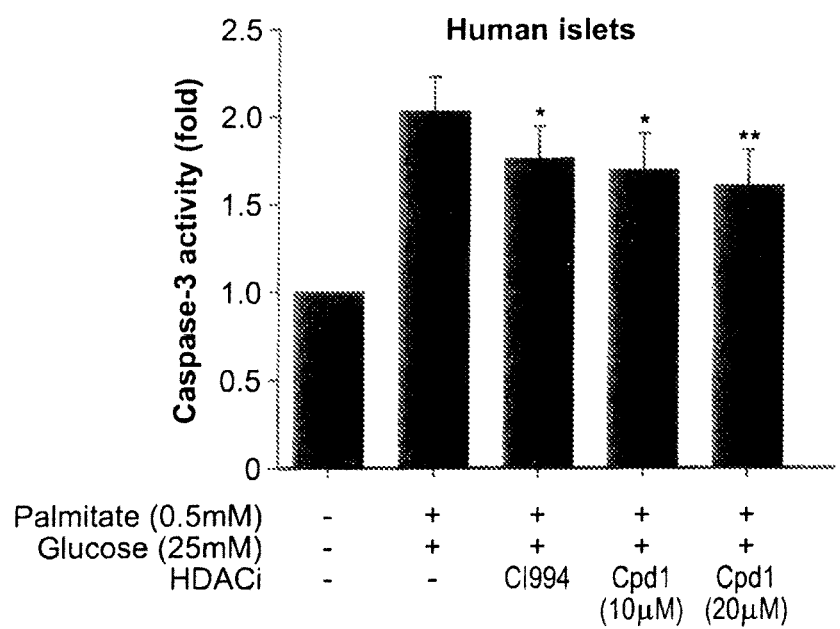
FIG. 10B shows that compound 1 decreases glucolipotoxicity-induced apoptosis in human islets.

Compounds of the invention protect against combined palmitate and high glucose induced apoptosis in INS-1E cells. For example, FIG. 10 shows that compound 1, a HDAC3 selective inhibitor, can protect against combined palmitate and high glucose induced apoptosis in INS-1E cells. FIG. 10A shows that 10 μM compound 1 decreases glucolipotoxicity-induced apoptosis in rat islets. FIG. 10B shows 10 µM compound 1 decreases glucolipotoxicity-induced apoptosis in human islets. Rat islets were exposed to 0.5 mM palmitate and 25 mM glucose or vehicle and treated with either MS275 (1 µM), CI-994 (1 µM), compound 1 (10 and 20 uM) or vehicle for 60 h after which apoptosis was measured by cell death (ELISA). Dispersed human islets were exposed to 0.5 mM palmitate and 25 mM glucose or vehicle and treated with either CI-994 (1 µM), compound 1 (10 and 20 µM) or vehicle for 72 h. Apoptosis was measured by caspase-3 activity assay.

Figure 11:
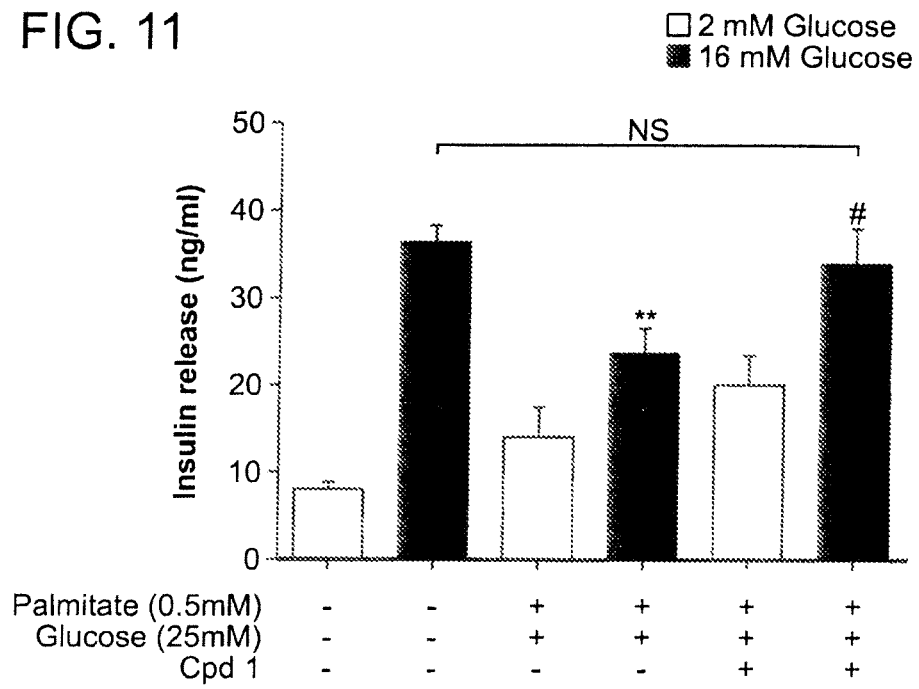
FIG. 11 is a bar graph which shows 10 μM compound 1 decreases glucolipotoxicity-induced dysfunction by restoring insulin release (glucose-stimulated) in INS-1E cells.
Figure 12:
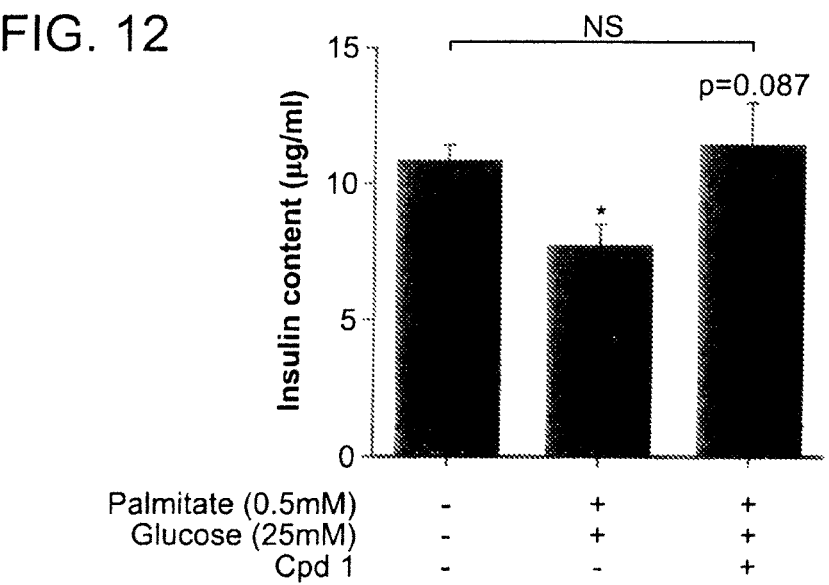
FIG. 12 is a bar graph which shows 10 μM compound 1 decreases glucolipotoxicity-induced dysfunction by restoring insulin content in INS-1E cells.

Specifically, HDAC3 inhibition is shown to preserve the glucose-induced insulin secretory function. For example, FIG. 11 shows that 10 µM compound 1 decreases glucolipotoxicity-induced dysfunction by restoring insulin release (glucose-stimulated) in INS-1E cells. FIG. 12 is a bar graph which shows that 10 µM compound 1 decreases glucolipotoxicity-induced dysfunction by restoring insulin content in INS-1E cells. FIG. 13 is a series of bar graphs.

Figure 13A:
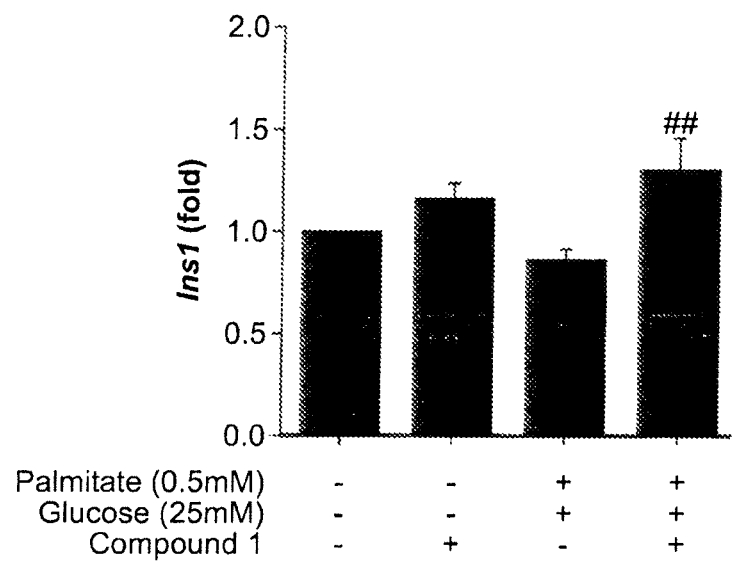
FIG. 13A shows that 10 μM compound 1 decreases glucolipotoxicity-induced dysfunction by partially restoring insulin gene Ins1 expression in INS-1E cells.
Figure 13B:
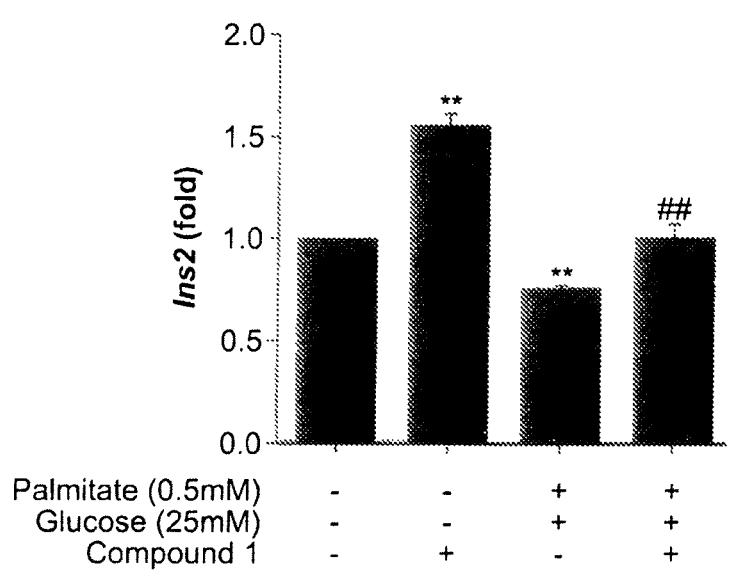
FIG. 13B shows that 10 μM compound 1 decreases glucolipotoxicity-induced dysfunction by partially restoring insulin gene Ins2 expression in INS-1E cells.

Compounds of the invention counteract glucolipotoxic reductions in insulin gene Ins1 and Ins2 expression. For example, FIG. 13A shows that 10 µM compound 1 decreases glucolipotoxicity-induced dysfunction by partially restoring insulin gene Ins1 expression in INS-1E cells. FIG. 13B shows 10 µM compound 1 reduces glucolipotoxicity-induced dysfunction by partially restoring insulin gene Ins2 expression in INS-1E cells. The gene expression in FIGS. 13A and 13B were analyzed by qPCR.

In FIGS. 11, 12, 13A, and 13B, INS-1E cells were exposed to 0.5 mM and 25 mM glucose or vehicle and treated with compound 1 (10 µM) or vehicle for 24 h. Glucose-stimulated insulin secretion and total insulin content were assessed by ELISA. Data are presented as fold to CTRL+SEM, n=3-5, ns=not significant, * p<0.05,  p<0.01, * p<0.001 vs. CTRL, #p<0.05, ##p<0.01, ###p<0.001 vs. respective treatment. ANOVA with Tukey- or Dunnet-corrected test, or Student's t-test (insulin content).

Figure 14A:
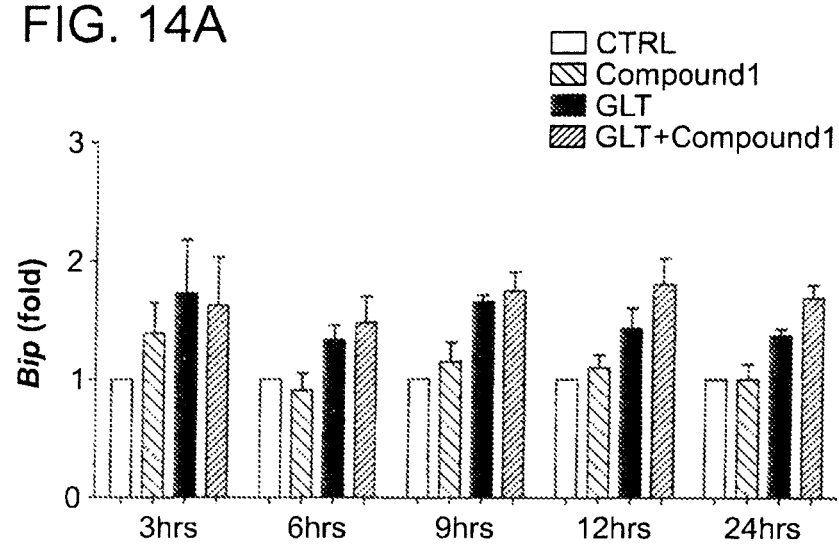
FIG. 14A shows the gene Bip expression.
Figure 14B:
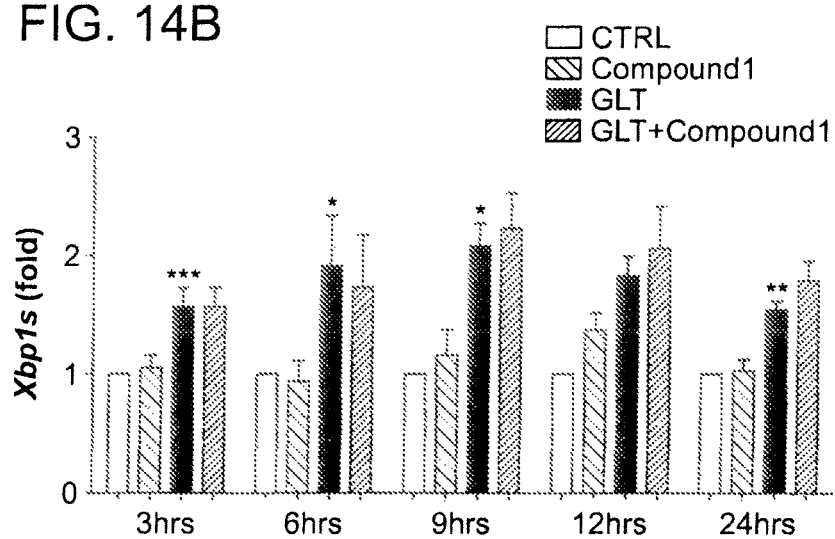
FIG. 14B shows the gene Xbp1s expression.
Figure 14C:
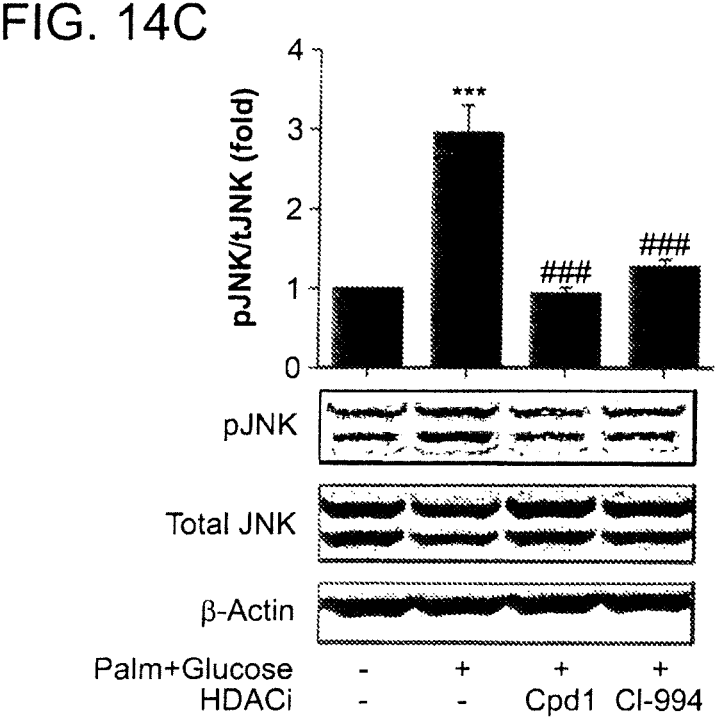
FIG. 14C shows the protein pJNK/tJNK level.
Figure 14D:
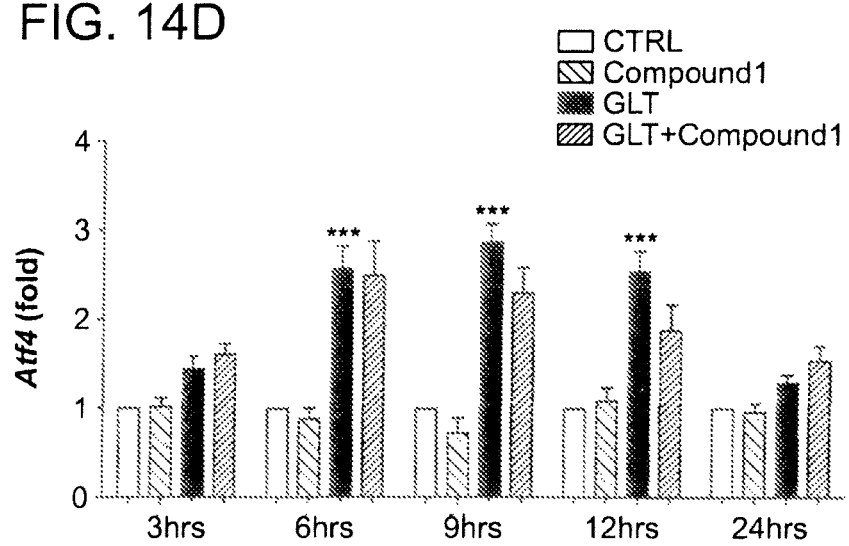
FIG. 14D shows the gene Atf4 expression.
Figure 14E:
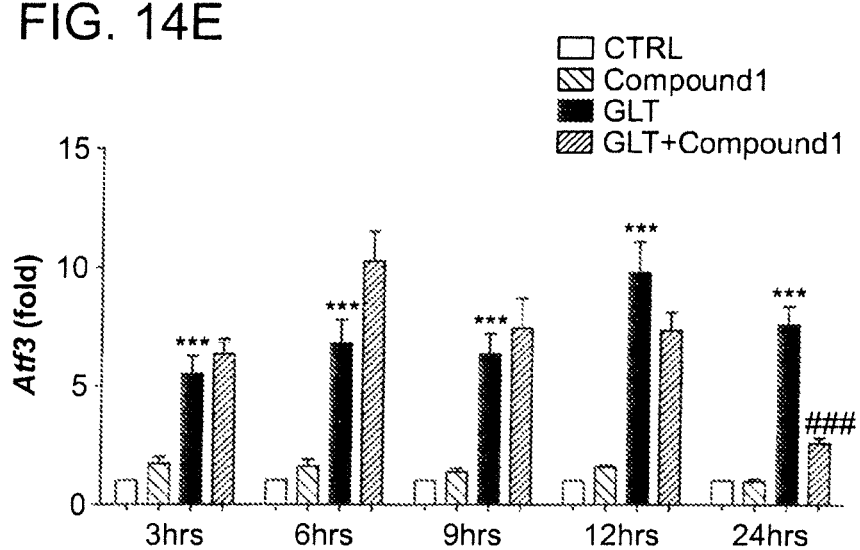
FIG. 14E shows the gene Atf3 expression.
Figure 14F:
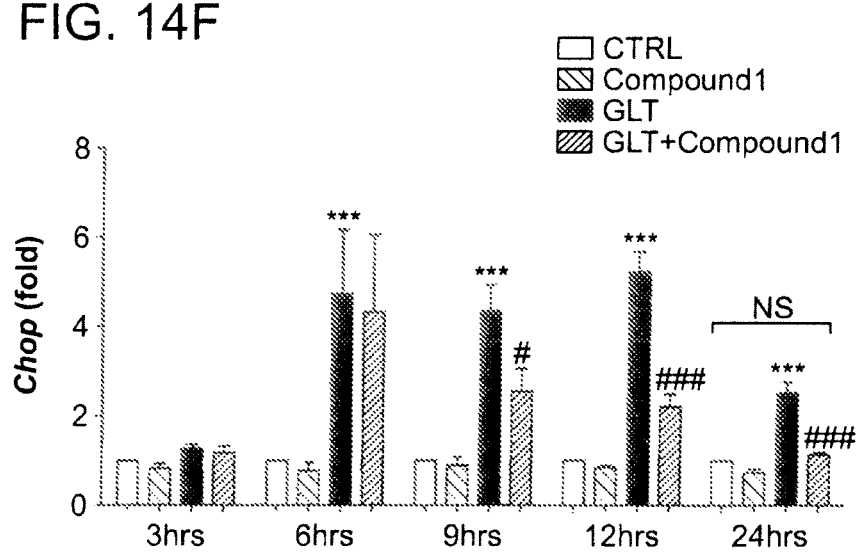
FIG. 14F shows the gene Chop expression.
Figure 14G:
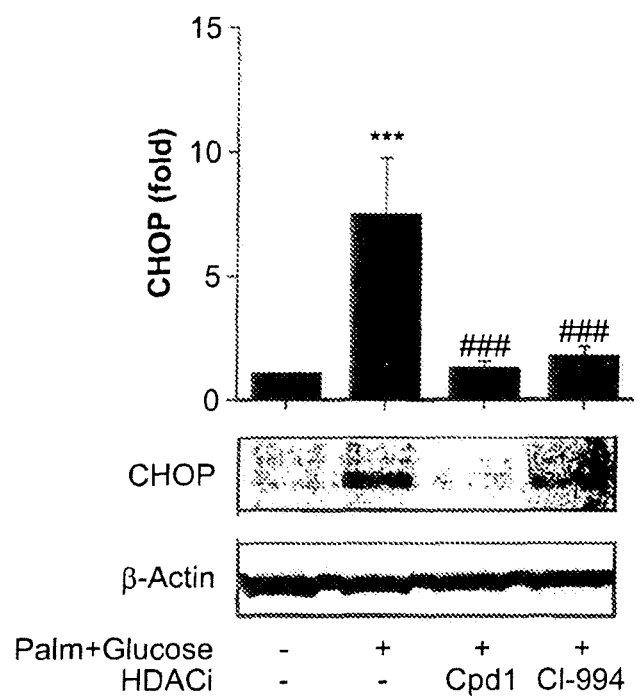
FIG. 14G shows the protein CHOP expression.

Compounds of the invention inhibit HDAC3 and reduce ER stress. The effect of a compound of the invention on glucolipotoxicity-induced changes in the three main pathways of the UPR; the IRE-pathway (Xbp1s, JNK), the PERK-pathway (Atf4, Atf3, and CHOP and the ATF6-pathway (Bip) was examined. Specifically, FIG. 14 shows that 10 µM compound 1 reduces endoplasmic reticulum (ER) stress by reducing CHOP expression and JNK phosphorylation. Compound 1 did not change the levels of the ER chaperone Bip mRNA (FIG. 14A), suggesting that the protective effect of HDAC3 inhibition is independent of the ATF6-Bip pathway. Compound 1 did not affect splicing of the transcription factor Xbp1 to Xbp1 s (FIG. 14B), but inhibited phosphorylation of JNK after 24 hrs (FIG. 14C), consistent with a decrease in ROS levels (FIG. 15B, see below). Compound 1 did not affect Atf4 transcription factor induction (FIG. 14D), but decreased the ATF4-mediated induction of the transcription factors Atf3 (FIG. 14E) and Chop (FIG. 14F) after 24 hrs and 9 hrs, respectively. CHOP mRNA and protein induction was completely reversed by compound after 24 hrs (FIG. 14G). HDAC inhibition also reduced tunicamycin-induced ER stress dependent apoptosis, demonstrating a more general protective action of HDAC inhibition on ER stress (results not shown).

INS-1E cells were exposed to 0.5 mM palmitate and 25 mM glucose (GLT) or vehicle and treated with CI-994 (1 µM), compound 1 (10 uM) or vehicle for 3, 6, 9, 12, 24 or 48 h. Gene expressions (vehicle=open bars, compound 1=light grey bars, GLT=black bars, GLT and compound 1=dark grey bars) were analyzed by qPCR (FIGS. 14A, 14B, 14D, 14E, and 14F) and protein levels (FIGS. 14C and 14G) (24 h) by immunoblotting. Representative blots are shown. Data are presented as fold to CTRL+SEM n=3-4, ns=not significant, *p<0.05, p<0.01, *p<0.001 vs unexposed cells; #p<0.05, ##p<0.01, ###p<0.001 vs. GLT treated cells, ANOVA with Tukey corrected test.

Figure 15:
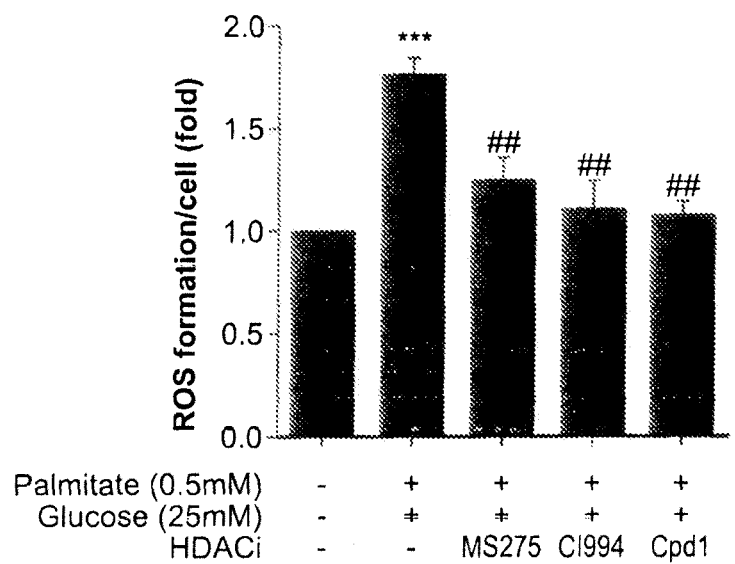
FIG. 15 is a bar graph which shows 10 μM compound 1 reduces glucolipotoxicity-induced ROS formation.

Glucolipotoxicity causes oxidative stress in β cells via increased ROS formation from mitochondria. (Lenzen, S. (2008) Biochem. Soc. Trans. 36, 343-347.) HDAC3 inhibition can decrease glucolipotoxicity-induced loss of mitochondrial activity and this may be correlated with a decrease in ROS generation. For example, FIG. 15 shows that 10 µM compound 1 reduces glucolipotoxicity-induced ROS formation. INS-1E cells were exposed to 0.5 mM palmitate and 25 mM glucose (GLT) or vehicle and treated with MS275 (1 µM), CI-994 (1 µM), compound 1 (10 uM) or vehicle for 24 or 48 h. ROS formation per cell (48 hrs) was measured using the CM-H2DCFDA probe and Hoechst staining. Data are presented as fold to CTRL+SEM n=3-4, ns=not significant, p<0.01, *p<0.001 vs unexposed cells; #p<0.05, ##p<0.01, vs. GLT treated cells, ANOVA with Tukey corrected test.

In summary, compound 1 is shown to be effective at rescuing INS-1E cells from lipotoxicity. Compound 1 is shown to protect against combined palmitate and high glucose induced apoptosis in INS-1E cells. Compound 1 is shown to counteract glucolipotoxic reduction in insulin gene Ins1 and Ins2 expression, glucose-stimulated insulin release, and insulin content. Thus, HDAC3 inhibition protects against fatty-acid and glucose induced apoptosis and preserves the glucose-induced insulin secretory function.

Example 9

Figure 16A:
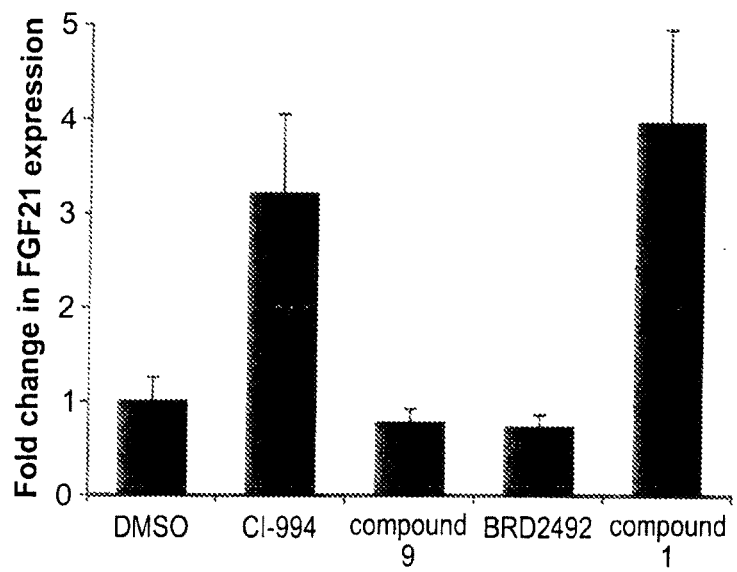
FIG. 16A shows the fold change in FGF21 expression in HepG2 cells after 2 hours following treatment with CI-994, compound 9 (negative control), BRD2492 (an HDAC1,2 selective inhibitor) and compound 1 (an HDAC3 selective inhibitor. Compound 1 upregulates FGF21 mRNA expression in HepG2 cells after 2 hours.
Figure 16B:
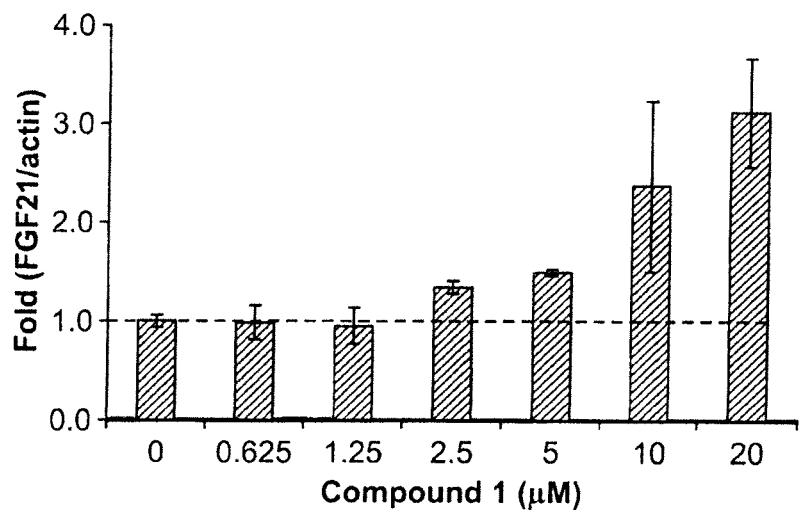
FIG. 16B shows compound 1 dose response increases in FGF21 expression (FGF21/actin) in HepG2 cells.

Compounds of the invention were evaluated for their ability to upregulate FgF21 mRNA expression in HepG2 cells. FgF21 (Fibroblast growth factor 21) is a potent insulin sensitizer and stimulatory signal for fat oxidation. (Li, H. et al. Diabetes, 61, 797, 2012; Kliewe, S. A., The American Journal of Clinical Nutrition, 91, 254S, 2010). The assay protocol was as follows. HepG2 cells were cultured in DMEM and 10% FBS. For measurement of FGF21 mRNA, we seeded 250,000 cells/well in 24-well plates, and serum-starved cells overnight in DMEM with 0.25% bovine serum albumin (BSA). We treated cells with the indicated compounds for two hours, and lysed and extracted mRNA using the Rneasy kit (Qiagen). Compound concentration was 20 µM. Quantitative PCR was performed using Taqman probes specific for human FGF21 and human actin. The results are presented in FIGS. 16A and 16B. The results show that compound 1 upregulates FGF21 mRNA expression in HepG2 cells.

Example 10

Compounds of the invention were evaluated for their effect on the growth of human megakaryocyte progenitors (surrogate assay for platelet depletion). Human CD34+ cells were grown in a collagen-based gel (Megacult-C, Stemcell Technologies). The cells were treated with compound 1, compound 9, CI-994, and BRD2492 at 0.1 µM, 1 µM, 10 µM, and 20 µM. The results are presented in FIG. 17. The vertical axis in FIG. 17 shows the viability of cells treated with drug as a percentage to the to cells treated with DMSO only. 100% indicates no difference in cell viability relative to the DMSO treated cells. The results show the effect that HDAC inhibition can have on cell growth. Specifically, FIG.

17 shows that compound 1, an HDAC3 selective inhibitor, does not significantly inhibit cell growth. This is the desired effect. In contrast, the non-selective HDAC inhibitors such as CI-994 (an HDAC1,2,3 inhibitor) and BRD2492 (an HDAC1,2 inhibitor) are shown to be highly toxic, particularly at higher concentrations such as 10 μM and 20 μM. CI-994 shows a significant toxic effect on cell growth even at a concentration of 1 μM. These results highlight the important advantages that may be gained when a subject is treated with a selective HDAC3 compound. Administration of an HDAC3 selective compound may result in lower toxicity in comparison to a non-selective inhibitor and may provide a larger therapeutic window because the selective compound is able to be safely administered at a higher dose due to its low toxicity.

We claim:
1. A compound of formula I:

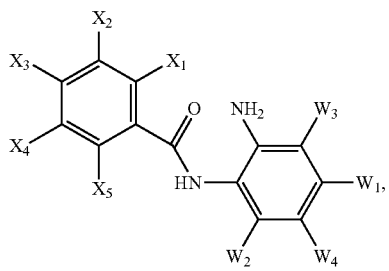

(I)

or a pharmaceutically acceptable salt, hydrate, solvate, or prodrug thereof, wherein:
- $X_3$ is NR1C(O)R2, wherein R2 is unsubstituted C1-C8 alkyl, CF3, CH2F, or CF2H;
- $W_1$, $W_2$, $W_3$, and $W_4$ are each independently selected from hydrogen, fluorine, chlorine, bromine, $CF_3$, $CH_3$, and deuterium, provided that at least one of $W_1$, $W_2$, $W_3$, and $W_4$ is not hydrogen;
- $X_1$ and $X_5$ are each independently selected from hydrogen, halogen, and $C_1$-$C_3$ alkyl;
- $X_2$ and $X_4$ are each independently selected from hydrogen, halogen, $OR^5$, $C(O)R^6$, $OS(O)_pR^7$, $NR^3R^4$, $NR^1C(O)R^2$, $NR^1S(O)_pR^7$, $S(O)_qR^{10}$, $C(O)OR^{11}$, $C(O)NR^{12}R^{13}$, $OC(O)OR^{14}$, $OC(O)NR^{15}R^{16}$, $NR^{17}C(O)OR^{18}$, $NR^{19}C(O)NR^{20}R^{21}$, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^a$, provided that one or two of $X_2$ and $X_4$ is hydrogen;
- $R^a$ is selected from halogen, $OR^{25}$, $C_1$-$C_8$ alkyl, $CF_3$, $CHF_2$, $CH_2F$, $NR^{26}C(O)R^{27}$, and $NR^{28}R^{29}$; or
- $R^1$ and $R^{26}$ are each independently selected from hydrogen and $C_1$-$C_8$ alkyl;
- $R^2$ is selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkynyl, cycloalkyl, cycloalkenyl, aromatic ring, heteroaromatic ring, and heterocyclic ring are unsubstituted or substituted with one or more $R^b$;
- $R^{27}$ is selected from hydrogen, $C_1$-$C_8$ alkyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkynyl, cycloalkyl, cycloalkenyl, aromatic ring, heteroaromatic ring, and heterocyclic ring are unsubstituted or substituted with one or more $R^b$;
- $R^b$ is selected from halogen, $C_1$-$C_8$ alkyl, $CF_3$, $CHF_2$, $CH_2F$, $OR^{25}$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^{b1}$;
- $R^{b1}$ is selected from halogen, $C_1$-$C_3$ alkyl, $CF_3$, $CHF_2$, $CH_2F$, OH, $OCH_3$, $S(O)CH_3$, $S(O)_2CH_3$, $NH_2$, $NHCH_3$, and $N(CH_3)_2$;
- $R^3$ and $R^4$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^g$;
- $R^{28}$ and $R^{29}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloakenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^g$;
- $R^g$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^h$;
- $R^h$ is selected from halogen, $C_1$-$C_3$ alkyl, $CF_3$, $CHF_2$, $CH_2F$, OH, $OCH_3$, $S(O)CH_3$, $S(O)_2CH_3$, $NH_2$, $NHCH_3$, and $N(CH_3)_2$;
- $R^5$ and $R^{25}$ are each independently selected from hydrogen, $C(O)R^6$, $C_1$-$C_8$ alkyl, $CF_3$, $CHF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^c$;
- $R^c$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^d$;

$R^d$ is selected from halogen, $C_1$-$C_3$ alkyl, $CF_3$, $CHF_2$, $CH_2F$, OH, $OCH_3$, $S(O)CH_3$, $S(O)_2CH_3$, $NH_2$, $NHCH_3$, and $N(CH_3)_2$;

$R^6$ is selected from hydrogen, $OR^{25}$, $C_1$-$C_8$ alkyl, $CF_3$, $CHF_2$, $CH_2F$, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring; wherein said alkyl, alkenyl, alkynyl, cycloalkyl, cycloalkenyl, aromatic ring, heteroaromatic ring, and heterocyclic ring are unsubstituted or substituted with one or more $R^e$;

$R^e$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^f$;

$R^f$ is selected from halogen, $C_1$-$C_3$ alkyl, $CF_3$, $CHF_2$, $CH_2F$, OH, $OCH_3$, $S(O)CH_3$, $S(O)_2CH_3$, $NH_2$, $NHCH_3$, and $N(CH_3)_2$;

$R^7$ is selected from $C_1$-$C_8$ alkyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring; wherein said alkyl, cycloalkyl, cycloalkenyl, aromatic ring, heteroaromatic ring, and heterocyclic ring are unsubstituted or substituted with one or more $R^i$;

$R^i$ is selected from halogen, $C_1$-$C_3$ alkyl, $CF_3$, $CHF_2$, $CH_2F$, OH, $OCH_3$, $NH_2$, $NHCH_3$, and $N(CH_3)_2$;

$R^{10}$ is selected from $C_1$-$C_8$ alkyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring; wherein said alkyl, cycloalkyl, cycloalkenyl, aromatic ring, heteroaromatic ring, and heterocyclic ring are unsubstituted or substituted with one or more $R^j$;

$R^j$ is selected from halogen, $C_1$-$C_3$ alkyl, $CF_3$, $CHF_2$, $CH_2F$, OH, $OCH_3$, $NH_2$, $NHCH_3$, and $N(CH_3)_2$;

$R^{11}$ is selected from hydrogen, $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring; wherein said alkyl, alkenyl, alkynyl, cycloalkyl, cycloalkenyl, aromatic ring, heteroaromatic ring, and heterocyclic ring are unsubstituted or substituted with one or more $R^k$;

$R^k$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^{k1}$;

$R^{k1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{12}$ and $R^{13}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^l$;

$R^l$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^m$;

$R^m$ is selected from halogen, $C_1$-$C_3$ alkyl, $CF_3$, $CHF_2$, $CH_2F$, OH, $OCH_3$, $S(O)CH_3$, $S(O)_2CH_3$, $NH_2$, $NHCH_3$, and $N(CH_3)_2$;

$R^{14}$ is selected from $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, and aromatic ring; wherein said alkyl, alkenyl, alkynyl, cycloalkyl, cycloalkenyl, and aromatic ring are unsubstituted or substituted with one or more $R^n$;

$R^n$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^{n1}$;

$R^{n1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{15}$ and $R^{16}$ are each independently selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^o$;

$R^o$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^p$;

$R^p$ is selected from halogen, $C_1$-$C_3$ alkyl, $CF_3$, $CHF_2$, $CH_2F$, OH, $OCH_3$, $S(O)CH_3$, $S(O)_2CH_3$, $NH_2$, $NHCH_3$, and $N(CH_3)_2$;

$R^{17}$ and $R^{19}$ are each independently selected from hydrogen and $C_1$-$C_8$ alkyl;

$R^{18}$ is selected from $C_1$-$C_8$ alkyl, $C_2$-$C_8$ alkenyl, $C_2$-$C_8$ alkynyl, $C_3$-$C_8$ cycloalkyl, $C_4$-$C_8$ cycloalkenyl, aromatic ring, 3-8 membered heteroaromatic ring, and 3-8 membered saturated heterocyclic ring; wherein said alkyl, alkenyl, alkynyl, cycloalkyl, cycloalkenyl, heteroaromatic ring, heterocyclic ring, and aromatic ring are unsubstituted or substituted with one or more $R^q$;

$R^q$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^{q1}$;

$R^{q1}$ is selected from halogen, $C_1$-$C_3$ alkyl, $CF_3$, $CHF_2$, $CH_2F$, OH, $OCH_3$, $SO_2CH_3$, $NH_2$, $NHCH_3$, and $N(CH_3)_2$;

$R^{20}$ and $R^{21}$ are each independently selected from selected from hydrogen, $C_1$-$C_8$ alkyl, $C_2$-$C_8$ alkenyl, $C_3$-$C_8$ alkynyl, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said alkyl, alkenyl, alkynyl, cycloalkyl, cycloalkenyl, aromatic ring, heteroaromatic ring, and heterocyclic ring are unsubstituted or substituted with one or more $R^r$;

$R^r$ is selected from halogen, $C_1$-$C_3$ alkyl, $CF_3$, $CHF_2$, $CH_2F$, OH, $OCH_3$, $NH_2$, $NHCH_3$, $N(CH_3)_2$, $C_3$-$C_8$ cycloalkyl, $C_4$-$C_8$ cycloalkenyl, aromatic ring, 3-8 membered heteroaromatic ring, and 3-8 membered, saturated or partially saturated, heterocyclic ring, wherein said cycloalkyl, cycloalkenyl, aromatic ring, heteroaromatic ring, and heterocyclic ring are unsubstituted or substituted with one or more $R^s$;

$R^s$ is selected from halogen, $C_1$-$C_3$ alkyl, $CF_3$, $CHF_2$, $CH_2F$, OH, $OCH_3$, $S(O)CH_3$, $SO_2CH_3$, $NH_2$, $NHCH_3$, and $N(CH_3)_2$; and p and q are each independently selected from 0, 1, and 2.

2. The compound of claim 1, or a pharmaceutically acceptable salt, hydrate, solvate, or prodrug thereof, wherein $X_1$, $X_2$, $X_4$, and $X_5$ are all hydrogen.

3. The compound of claim 1, or a pharmaceutically acceptable salt, hydrate, solvent, or prodrug thereof, wherein one of $X_1$, $X_2$, $X_4$, and $X_5$ is halogen.

4. A kit containing one or more compounds of claim 1, or a pharmaceutically acceptable salt, hydrate, solvate, or prodrug thereof.

5. The compound of claim 1, wherein the compound is of Formula (I), or a pharmaceutically acceptable salt thereof.

6. The compound of claim 1, wherein the compound is of the formula:

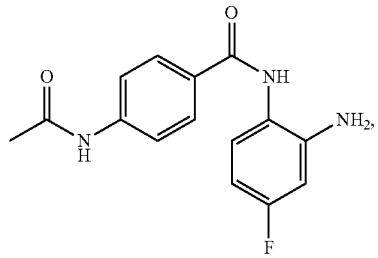

(II)

or a pharmaceutically acceptable salt, hydrate, solvate, or prodrug thereof.

7. The compound of claim 1, wherein the compound is of the formula:

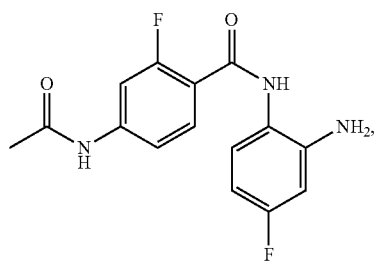

(III)

or pharmaceutically acceptable salt, hydrate, solvate, or prodrug thereof.

8. The compound of claim 1, wherein $X_3$ is $NHC(O)CH_3$.

9. The compound of claim 1, wherein the compound is of the formula:

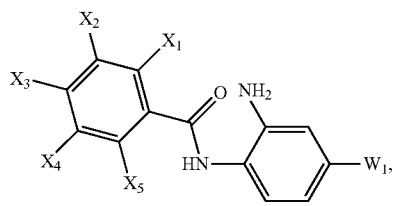

1 or a pharmaceutically acceptable salt, hydrate, solvate, or prodrug thereof.

10. The compound of claim 1, wherein the compound is of the formula:

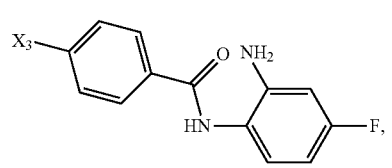

6 or a pharmaceutically acceptable salt, hydrate, solvate, or prodrug thereof.

11. A pharmaceutical composition comprising an effective amount of a compound of claim 1, or pharmaceutically acceptable salt, hydrate, solvate, or prodrug thereof, and a pharmaceutical carrier, diluent, or excipient.

12. A method of treating or alleviating an HDAC3 mediated disease in a subject comprising administering to a subject in need thereof an effective amount of a compound of claim 1, or a pharmaceutically acceptable salt, hydrate, solvate, or prodrug thereof, wherein the HDAC3 mediated disease is cognitive function disorder, extinction learning disorder, memory loss or impairment, diabetes, obesity, Gaucher disease, Niemann-Pick type C disease, liver disease, post-traumatic stress disorder (PTSD), phobias, drugg addiction, anxiety disorder, obsessive compulsive disorder, bipolar disorder, major depressive disorder, schizophrenia, Alzheimer's disease, Parkinson's disease, Huntington'disease, leukemia, lymphoma, melanoma, liver cancer, or lung cancer.

13. The method of claim 12, wherein the HDAC3 mediated disease is lymphoma.

14. The method of claim 13, wherein the lymphoma is cutaneous T-cell lymphoma (CTCL), noncutaneous peripheral T-cell lymphoma, lymphoma associated with human T-cell lymphotrophic virus (HTLV), adult T-cell leukemia/lymphoma (ATLL), Hodgkin's disease, non-Hodgkin's lymphoma, large-cell lymphoma, diffuse large B-cell lymphoma (DLBCL), Burkitt's lymphoma, or primary central nervous system (CNS) lymphoma.

15. The method of claim 12, wherein the HDAC3 mediated disease is melanoma.

16. The method of claim 12, wherein the HDAC3 mediated disease is lung cancer.

17. The method of claim 12, wherein the HDAC3 mediated disease is post-traumatic stress disorder (PTSD), phobias, or drug addiction.

18. The method of claim 12, wherein the HDAC3 mediated disease is Alzheimer's disease, Parkinson's disease, or Huntington's disease.

19. The method of claim 12, wherein the compound is of the formula:

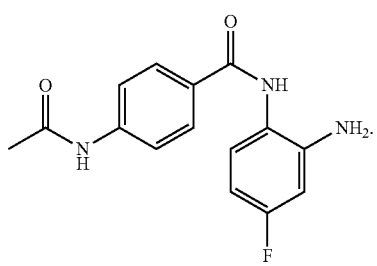

20. A method of treating or alleviating an HDAC3 mediated disease in a subject comprising administering to a subject in need thereof an effective amount of: a compound of claim 1, or a pharmaceutically acceptable salt, hydrate, solvate, or prodrug thereof, and an anti-cancer or chemotherapeutic agent, in combination or seperately, wherein the HDAC3 mediated disease is breast cancer.

21. The method of claim 20, wherein the compound is of the formula:

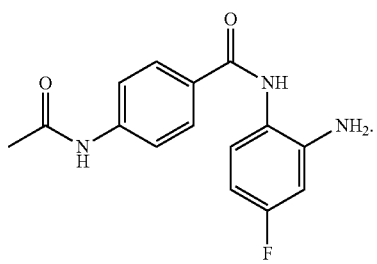

22. A compund of the formula:

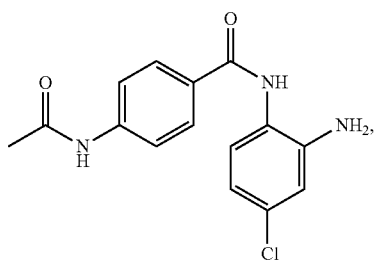

-continued

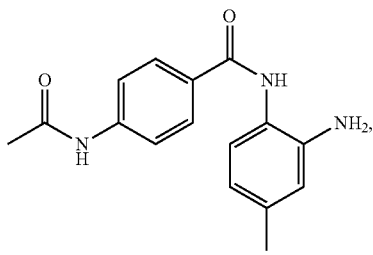

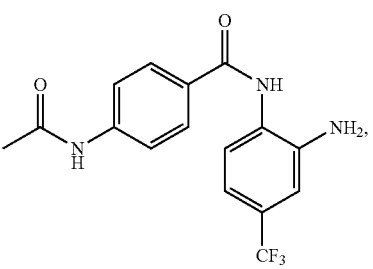

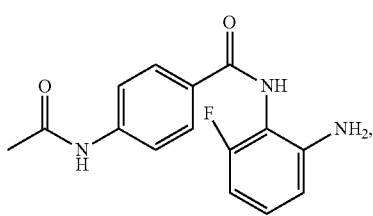

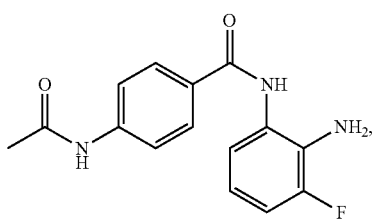

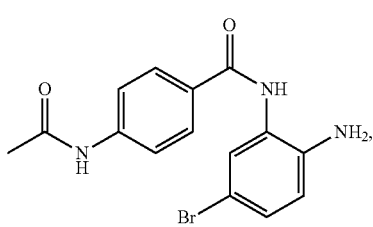

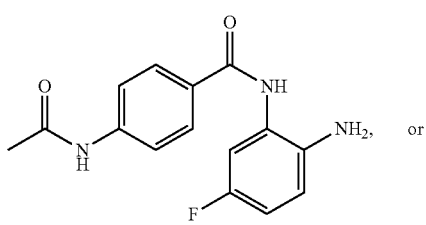

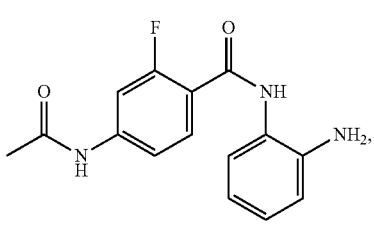

or a pharmaceutically acceptable salt, hydrate, solvate, or prodrug thereof.

23. A pharmaceutical composition comprising an effective amount of a compound of claim 22, or pharmaceutically acceptable salt, hydrate, solvate, or prodrug thereof, and a pharmaceutical carrier, diluent, or excipient.

24. A method of treating or alleviating an HDAC3 mediated disease in a subject comprising administering to a subject in need thereof an effective amount of a compound of claim 22, or a pharmaceutically acceptable salt, hydrate, solvate, or prodrug thereof, wherein the HDAC3 mediated disease is cognitive function disorder, extinction learning disorder, memory loss or impairment, diabetes, obesity, Gaucher disease, Niemann-Pick type C disease, liver disease, post-traumatic stress disorder (PTSD), phobias, drug addiction, anxiety disorder, obsessive compulsive disorder, bipolar disorder, major depressive disorder, schizophrenia, ALzheimer's disease, Parkinson's disease, Huntington's disease, leukemia, lymphoma, melanoma, liver cancer, or lung cancer.

25. A method of treating or alleviating an HDAC3 mediated disease in a subject comprising administering to a subject in need thereof an effective amount of: a compound of claim 22, or a pharmaceutically acceptable salt, hydrate, solvate, or prodrug thereof, and an anti-cancer or chemotherapeutic agent, in combination or separately, wherein the HDAC3 mediated disease is breast cancer.

\* \* \* \* \*

UNITED STATES PATENT AND TRADEMARK OFFICE
CERTIFICATE OF CORRECTION

| | | |
|---|---|---|
| PATENT NO. | : 9,790,184 B2 | Page 1 of 1 |
| APPLICATION NO. | : 14/417477 | |
| DATED | : October 17, 2017 | |
| INVENTOR(S) | : Edward Holson et al. | |

It is certified that error appears in the above-identified patent and that said Letters Patent is hereby corrected as shown below:

In Claim 1, at Column 97, Lines 39-40, the text: "provided that at least one of $W_1$, $W_2$, $W_3$, and $W_4$ is not hydrogen" should be replaced with: --provided that at least one of $W_1$, $W_2$, $W_3$, and $W_4$ is not hydrogen or deuterium--.

In Claim 1, at Column 97, Lines 63-64, the text: "3-8 membered, saturated or partially saturated, heterocyclic ring, wherein said alkyl, alkynyl, cycloalkyl," should be replaced with: --3-8 membered, saturated or partially saturated, heterocyclic ring, wherein said alkyl, alkenyl, alkynyl, cycloalkyl,--.

In Claim 7, at Column 101, Line 65, the text: "or pharmaceutically acceptable salt, hydrate, solvate, or" should be replaced with: --or a pharmaceutically acceptable salt, hydrate, solvate, or--.

In Claim 12, at Column 102, Lines 50-51, the text: "Post-Traumatic stress disorder (PTSD), phobias, drugg addiction" should be replaced with: --Post-Traumatic stress disorder (PTSD), phobias, drug addiction--.

In Claim 12, at Column 102, Line 54, the text: "Huntington'disease" should be replaced with: --Huntington's disease--.

In Claim 22, at Column 103, Line 54, the text: "A compund of the formula:" should be replaced with: --A compound of the formula:--.

In Claim 24, at Column 106, Line 9, the text: "ALzheimer's disease" should be replaced with: --Alzheimer's disease--.

Signed and Sealed this
Twenty-second Day of May, 2018

Andrei Iancu
*Director of the United States Patent and Trademark Office*